(12) United States Patent
Alonso-de Diego et al.

(10) Patent No.: US 10,512,646 B2
(45) Date of Patent: *Dec. 24, 2019

(54) SUBSTITUTED 6,7-DIHYDROPYRAZOLO[1,5-A]PYRAZINES AS NEGATIVE ALLOSTERIC MODULATORS OF MGLUR2 RECEPTORS

(71) Applicant: Janssen Pharmaceutica NV, New Brunswick, NJ (US)

(72) Inventors: Sergio-Alvar Alonso-de Diego, Toledo (ES); Michiel Luc Maria Van Gool, Madrid (ES); Óscar Delgado-González, Madrid (ES); José Ignacio Andrés-Gil, Toledo (ES); Andrés Avelino Trabanco-Suárez, Toledo (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/976,037

(22) Filed: May 10, 2018

(65) Prior Publication Data

US 2018/0256569 A1 Sep. 13, 2018

Related U.S. Application Data

(63) Continuation of application No. 15/500,600, filed as application No. PCT/EP2015/067530 on Jul. 30, 2015, now Pat. No. 10,005,786.

(30) Foreign Application Priority Data

Aug. 1, 2014 (EP) ..................................... 14179598
Aug. 1, 2014 (EP) ..................................... 14179598

(51) Int. Cl.
| A61K 31/4985 | (2006.01) |
| A61P 25/24 | (2006.01) |
| C07D 487/04 | (2006.01) |
| A61K 31/506 | (2006.01) |

(52) U.S. Cl.
CPC ........ *A61K 31/4985* (2013.01); *A61K 31/506* (2013.01); *A61P 25/24* (2018.01); *C07D 487/04* (2013.01)

(58) Field of Classification Search
CPC ............................. A61K 31/4985; A61P 25/24
See application file for complete search history.

(56) References Cited

U.S. PATENT DOCUMENTS

| 10,005,786 B2 * | 6/2018 | Alonso-de Diego ........................ C07D 487/04 |
| 2001/0011087 A1 | 8/2001 | Wehner et al. |
| 2003/0027807 A1 | 2/2003 | Wehner et al. |
| 2005/0107412 A1 | 5/2005 | Maw et al. |
| 2013/0310555 A1 | 11/2013 | Chong |

FOREIGN PATENT DOCUMENTS

| EP | 0756200 B1 | 1/1997 |
| EP | 2327704 A1 | 6/2011 |
| EP | 2666775 A1 | 11/2013 |
| WO | 2002096873 A1 | 12/2002 |
| WO | 2005002552 A2 | 1/2005 |
| WO | 2005061507 A1 | 7/2005 |
| WO | 2005/123738 A1 | 12/2005 |
| WO | 2006030847 A1 | 3/2006 |
| WO | 2006050803 A1 | 5/2006 |
| WO | 2006/084634 A1 | 8/2006 |
| WO | 2006/099972 A1 | 9/2006 |
| WO | 2007084314 A2 | 7/2007 |
| WO | 2008001115 A2 | 1/2008 |
| WO | 2008141239 A1 | 11/2008 |
| WO | 2009095872 A2 | 8/2009 |
| WO | 2009118292 A1 | 10/2009 |
| WO | 2010130423 A1 | 11/2010 |

(Continued)

OTHER PUBLICATIONS

Alfonso R Gennaro, 18th edition Remington's—Pharmaceutical Sciences, 18th edition Remington's—Pharmaceutical Sciences, 1990, Part 8_ Pharmaceutical preparations and their Manufacture. pp. 1435-1714, Part 8.

Alper R. et al, Agonist-Stimulated [35S]GTBgS Binding, Current Protocols in Pharmacology, 1998, suppl.2.

Celia Goeldner, Cognitive impairment in major depression and the mGlu2 receptor as a therapeutic target, Neuropharmacology, Aug. 3, 2013, pp. 337-346, 64.

Cid Jose Maria et al, Discovery of 3-Cyclopropylmethyl-7-(4-phenylpiperidin-1-yl)-8-trifluoromethyl[1,2,4]triazolo [4,3-a]pyridine (JNJ-42153605): A Positive Allosteric Modulator of the Metabotropic Glutamate 2 Receptor, Journal of Medicinal Chemistry, Oct. 16, 2012, pp. 8770-8789, 55.

(Continued)

*Primary Examiner* — Theodore R. West

(57) ABSTRACT

The present invention relates to novel 6,7-dihydropyrazolo[1,5-a]pyrazin-4(5H)-one derivatives of Formula (I)

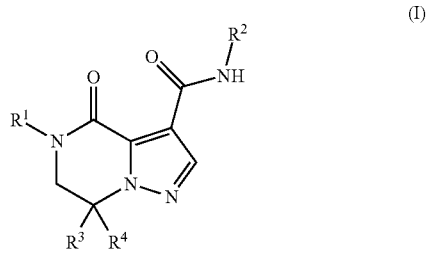

as negative allosteric modulators (NAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which the mGluR2 subtype of metabotropic receptors is involved.

9 Claims, No Drawings

(56) References Cited

FOREIGN PATENT DOCUMENTS

| WO | 2010130424 | | 11/2010 |
|---|---|---|---|
| WO | 2012035078 | A1 | 3/2012 |
| WO | 2012062752 | A1 | 5/2012 |
| WO | 2012083224 | A1 | 6/2012 |
| WO | 2012143726 | A1 | 10/2012 |
| WO | 2012/172093 | A1 | 12/2012 |
| WO | 2013012915 | A1 | 1/2013 |
| WO | 2013012918 | A1 | 1/2013 |
| WO | 2013/077059 | A1 | 5/2013 |
| WO | 2013066736 | A1 | 5/2013 |
| WO | 2013154878 | A1 | 10/2013 |
| WO | 2013156869 | A1 | 10/2013 |
| WO | 2013174822 | | 11/2013 |
| WO | 2013192343 | A1 | 12/2013 |
| WO | 2013192347 | A1 | 12/2013 |
| WO | 2013192350 | A1 | 12/2013 |
| WO | 2014/063549 | A1 | 5/2014 |
| WO | 2014064028 | A1 | 5/2014 |
| WO | 2014195311 | A1 | 12/2014 |
| WO | 016380 | | 2/2016 |
| WO | 016395 | A1 | 2/2016 |
| WO | 2016016381 | A1 | 2/2016 |
| WO | 2016016382 | A1 | 2/2016 |
| WO | 2016016383 | A1 | 2/2016 |
| WO | 2016087487 | A1 | 6/2016 |
| WO | 2016087489 | A1 | 6/2016 |
| WO | 2017103179 | A1 | 6/2017 |
| WO | 2017103182 | A1 | 6/2017 |

OTHER PUBLICATIONS

Dinklo Theo et al, Characterization of 2-[[4-Fluoro-3-(trifluoromethyl)phenyl]amino]-4-(4-pyridinyl)-5-thiazolemethanol (JNJ-1930942), a Novel Positive Allosteric Modulator of the 7 Nicotinic Acetylcholine Receptor☐S, The Journal of Pharmacology and Experimental Therapeutics, 2011, pp. 560-574, vol. 336 No. 2.

Embrechts S. et al, Longitudinal characterisation of the TauPS2APP mouse model of Alzheimer's disease in a two trial discrimination task of visuo-spatial recognition memory, 45th European Brain and Behaviour Society Meeting Sep. 3-9, 2013 Munich, Sep. 6, 2009, p. 202, not applicable.

Ferraguti, et al, Metabotropic glutamate receptors, Cell & Tissue Research, Jul. 18, 2006, pp. 483-504, 326.

Guy A. Higgins et al., Pharmacological manipulation of mGlu2 receptors influences, Neuropharmacology, 2004, pp. 907-917, vol. 46.

Hackam, et al, "Translation of Research Evidence From animals to Humans", JAMA, vol. 296 (14): pp. 1731-1732 (2006).

Hickinbottom, English translation of the relevent from reaction of organic complonents, Reactions of organic compounds, 1939, pp. 360-362, Page Number.

Hiroyuki Koike et al, Role of BDNF/TrkB signaling in antidepressant-like effects of a group II metabotropic glutamate receptor antagonist in animal models of depression, Behavioural Brain Research, Oct. 23, 2012, pp. 48-52, 238.

Kelmendi et al, The role of the Glutamatergic system in the pathophysiology and treatment of mood disorders, Primary Psychiatry, Oct. 2006, pp. 80-86, vol. 13 No. 10.

Li Jingjie et al, Palladium-Catalyzed Oxidative Rearrangement of Tertiary Allylic Alcohols to Enones with Oxygen in Aqueous Solvent, Organic Letters, Oct. 3, 2014, pp. 5370-5373, No. 16.

Lynne Gilfillian et al, Synthesis and biological evaluation of novel 2,3-dihydro-1H-1,5-benzodiazepin-2-ones; potential imaging agents of the metabotropic glutamate 2 receptor, Med. Chem. Commun., May 29, 2013, pp. 1118-1123, vol. 4 Issue 7.

NCT01457677, View of NCT01457677 on Feb. 18, 2014, ClinicalTrials.gov Archive, Feb. 18, 2014, pp. 1-3, not applicable.

Niswender Colleen M. et al, Metabotropic Glutamate Receptors: Physiology, Pharmacology, and Disease, Annu.Rev.Pharmacol.Toxicol., 2010, pp. 295-322, 50.

Schaffhauser et al, Pharmacological Characterization and Identification of Amino Acids Involved in the Positive Modulation of Metabotropic Glutamate Receptor Subtype 2, Molecular Pharmacology, Jun. 13, 2003, pp. 798-810, vol. 64, No. 4.

Serena Bigotti et al, Synthesis of C[CH(RF)NH]Gly-peptides: the dramatic effect of a single fluorine atom on thz diastereocontrol of the key aza-Michael reaction, Journal of Fluorine Chemistry, Jun. 27, 2008, pp. 767-774, 129.

Shigemoto, et al., Differential Presynaptic Localization of Metabotropic Glutamate Receptor Subtypes in the Rat Hippocampus, The Journal of Neuroscience, Oct. 1, 1997, pp. 7503-7522, vol. 17 Issue 19, Society for Neuroscience.

V. Craig Jordan, "Tamoxifen: A Most Unlikely Pioneering Medicine", Nature Reviews Drug Discovery, 2003, pp. 205-213, vol. 2.

Vippagunta et al, Crystalline solids, Advanced Drug Delivery Reviews, May 16, 2001, pp. 3-26, vol. 48 No. 1.

International Search Report for PCT/EP2015/067533 dated Oct. 19, 2015.

International Search Report for PCT/EP2015/067572 dated Sep. 9, 2015.

International Search Report for PCT/EP2015/067534 dated Sep. 10, 2015.

International Search Report for PCT/EP2015/067538 dated Sep. 9, 2015.

International Search Report for PCT/US2015/067530, dated Nov. 2, 2015.

Sheffler, et al., Recent Progress in the Synthesis and Characterization of Group II Metabotropic Glutamate Receptor Allosteric Modulators, ACS Chemical Neuroscience, Apr. 12, 2011, pp. 382-393, vol. 2, American Chemical Society.

* cited by examiner

SUBSTITUTED 6,7-DIHYDROPYRAZOLO[1,5-A]PYRAZINES AS NEGATIVE ALLOSTERIC MODULATORS OF MGLUR2 RECEPTORS

This application is a continuation application of U.S. patent application Ser. No. 15/500,600 filed Jan. 31, 2017, which is a 371 National Stage Application of PCT/EP2015/067530 with an international filing date of Jul. 30, 2015, and claims the benefit of EP 14179598.9 filed Aug. 1, 2014, the entire disclosures of each of which are hereby incorporated in their entirety.

FIELD OF THE INVENTION

The present invention relates to novel 6,7-dihydropyrazolo[1,5-a]pyrazin-4(5H)-one derivatives as negative allosteric modulators (NAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which the mGluR2 subtype of metabotropic receptors is involved.

BACKGROUND OF THE INVENTION

The glutamatergic system in the CNS is one of the neurotransmitter systems that play a key role in several brain functions. Metabotropic glutamate receptors (mGluR) belong to the G-protein-coupled family, and eight different subtypes have been identified to date, which are distributed to various brain regions (Ferraguti & Shigemoto, Cell & Tissue Research, 326:483-504, 2006). mGluRs participate in the modulation of synaptic transmission and neuronal excitability in the CNS by the binding of glutamate. This activates the receptor to engage intracellular signaling partners, leading to cellular events (Niswender & Conn, Annual Review of Pharmacology & Toxicology 50:295-322, 2010).

mGluRs are further divided into three subgroups based on their pharmacological and structural properties: group-I (mGluR1 and mGluR5), group-II (mGluR2 and mGluR3) and group-III (mGluR4, mGluR6, mGluR7 and mGluR8). Group-II ligands, both orthosteric and allosteric modulating, are considered to be potentially useful in the treatment of various neurological disorders, including psychosis, mood disorders, Alzheimer disease and cognitive or memory deficiencies. This is consistent with their primary localisation in brain areas such as the cortex, hippocampus and the striatum (Ferraguti & Shigemoto, Cell & Tissue Research 326:483-504, 2006). Particularly antagonists and negative allosteric modulators are reported to hold potential for the treatment of mood disorders and cognitive or memory dysfunction. This is based on findings with group-II receptor antagonists and negative allosteric modulators tested in laboratory animals subjected to a range of experimental conditions deemed relevant to these clinical syndromes (Goeldner et al, Neuropharmacology 64:337-346, 2013). Clinical trials are, for example, underway with mGluR2/3 antagonist decoglurant RO4995819 (F. Hoffmann-La Roche Ltd.) in adjunctive therapy in patients with Major Depressive Disorder having inadequate response to ongoing antidepressant treatment (ClinicalTrials.gov Identifier NCT01457677, retrieved 19 Feb. 2014). WO 2013066736 (Merck Sharp & Dohme Corp.) describes quinoline carboxamide and quinoline carbonitrile compounds as mGluR2 NAMs. WO2013174822 (Domain Therapeutics) describes 4H-pyrazolo[1,5-a]quinazolin-5-ones and 4H-pyrrolo [1,2-a]quinazolin-5-ones and in vitro mGluR2 NAM activity thereof. WO 2014064028 (F. Hoffman-La Roche AG) discloses a selection of mGlu2/3 negative allosteric modulators and their potential use in the treatment of Autistic Spectrum Disorders (ASD).

The group-II receptors are mainly located on presynaptic nerve terminals where they exert a negative feedback loop to the release of glutamate into the synapse (Kelmendi et al, Primary Psychiatry 13:80-86, 2006). Functional inhibition of these receptors by antagonists or negative allosteric modulators therefore lifts the brake on glutamate release, resulting in enhanced glutamatergic signaling. This effect is believed to underlie the antidepressant-like and procognitive effects observed in preclinical species with inhibitors of the Group-II receptor. In addition, treatment of mice with group-II orthosteric antagonists has been shown to enhance signaling by growth factors such as brain derived neurotrophic factor (BDNF) (Koike et al, Behavioural Brain Research 238:48-52, 2013). Since BDNF and other growth factors have been shown to be critically involved in mediating synaptic plasticity, this mechanism is likely to contribute to both antidepressant and procognitive properties of these compounds. Inhibition of mGluRs of the group-II receptor family is therefore considered to represent a potential therapeutic mechanism for neurological disorders, including depression and cognitive or memory dysfunction.

DESCRIPTION OF THE INVENTION

The present invention is directed to 6,7-dihydropyrazolo [1,5-a]pyrazin-4(5H)-one derivatives of Formula (I)

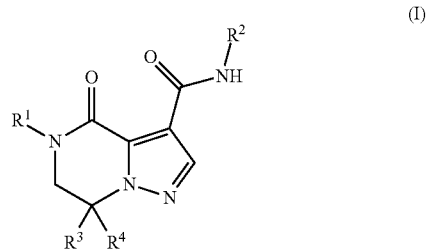

and stereoisomeric forms thereof, wherein $R^1$ is phenyl or 2-pyridinyl, each optionally substituted with one or more substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, $C_{3-7}$cycloalkyl, —O—$C_{1-4}$alkyl, monohalo-$C_{1-4}$alkyloxy, polyhalo-$C_{1-4}$alkyloxy, $SF_5$, $C_{1-4}$alkylthio, monohalo-$C_{1-4}$alkylthio and polyhalo-$C_{1-4}$alkylthio;

$R^2$ is selected from the group consisting of hydrogen; $C_{1-4}$alkyl; $C_{3-7}$cycloalkyl; Het$^1$; Aryl; —C(O)$R^5$; —C(O)Het$^2$; Het$^2$; and $C_{1-4}$alkyl substituted with one or more substituents each independently selected from the group consisting of halo, $C_{3-7}$cycloalkyl, Aryl, Het$^1$ and Het$^2$; wherein $R^5$ is selected from the group consisting of hydrogen, $C_{1-4}$alkyl and $C_{3-7}$cycloalkyl;

Aryl is phenyl optionally substituted with one or more substituents each independently selected from the group consisting of halo, $C_{1-4}$alkyl, —$C_{1-4}$alkyl-OH, monohalo-$C_{1-4}$alkyl, polyhalo-$C_{1-4}$alkyl, —CN, —O—$C_{1-4}$alkyl, —OH, —C$_{1-4}$alkyl-O—C$_{1-4}$alkyl, —NR'R", —NHC(O)C$_{1-4}$ alkyl, —C(O)NR'R", —C(O)NH[C(O)C$_{1-4}$alkyl], —S(O)$_2$ NR'R", —S(O)$_2$NH[C(O)C$_{1-4}$alkyl] and —SO$_2$—C$_{1-4}$alkyl;

Het$^1$ is selected from the group consisting of oxetanyl, tetrahydrofuranyl and tetrahydropyranyl;

Het$^2$ is (a) a 6-membered aromatic heterocyclyl substituent selected from the group consisting of pyridinyl, pyrimidinyl, pyrazinyl and pyridazinyl, each of which may be optionally substituted with one or more substituents each independently selected from the group consisting of halo, C$_{1-4}$alkyl, —C$_{1-4}$alkyl-OH monohalo-C$_{1-4}$alkyl, polyhalo-C$_{1-4}$alkyl, —CN, —O—C$_{1-4}$alkyl, —OH, —C$_{1-4}$alkyl-O—C$_{1-4}$alkyl, —NR'R", —NHC(O)C$_{1-4}$alkyl, —C(O)NR'R", —C(O)NH[C(O)C$_{1-4}$alkyl], —S(O)$_2$NR'R", —S(O)$_2$NH[C(O)C$_{1-4}$alkyl] and —SO$_2$—C$_{1-4}$alkyl; or (b) a 5-membered aromatic heterocyclyl selected from the group consisting of thiazolyl, oxazolyl, 1H-pyrazolyl and 1H-imidazolyl, each of which may be optionally substituted with one or more substituents each independently selected from the group consisting of halo, C$_{1-4}$alkyl, —C$_{1-4}$alkyl-OH, monohalo-C$_{1-4}$alkyl, polyhalo-C$_{1-4}$alkyl, —CN, —O—C$_{1-4}$alkyl, —OH, —C$_{1-4}$alkyl-O—C$_{1-4}$alkyl, —NR'R", —NHC(O)C$_{1-4}$alkyl, —C(O)NR'R", —C(O)NH[C(O)C$_{1-4}$alkyl], —S(O)$_2$NR'R", —S(O)$_2$NH[C(O)C$_{1-4}$alkyl] and —SO$_2$—C$_{1-4}$alkyl;

R' and R" are each independently selected from hydrogen and C$_{1-4}$alkyl; and

R$^3$ is selected from hydrogen and C$_{1-4}$alkyl;

R$^4$ is selected from the group consisting of hydrogen, C$_{1-4}$alkyl, monohalo-C$_{1-4}$alkyl, polyhalo-C$_{1-4}$alkyl, —C$_{1-4}$alkyl-O—C$_{1-4}$alkyl and —C$_{1-4}$alkyl-OH;

and the N-oxides and the pharmaceutically acceptable salts and the solvates thereof.

The present invention also relates to a pharmaceutical composition comprising a therapeutically effective amount of a compound of Formula (I) and a pharmaceutically acceptable carrier or excipient.

Additionally, the invention relates to a compound of Formula (I) for use as a medicament, and to a compound of Formula (I) for use in the treatment or in the prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

The invention also relates to the use of a compound of Formula (I) in combination with an additional pharmaceutical agent for use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

Furthermore, the invention relates to a process for preparing a pharmaceutical composition according to the invention, characterized in that a pharmaceutically acceptable carrier is intimately mixed with a therapeutically effective amount of a compound of Formula (I).

The invention also relates to a method of treating or preventing a central nervous system disorder selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder, comprising administering to a subject in need thereof, a therapeutically effective amount of a compound of Formula (I) or a therapeutically effective amount of a pharmaceutical composition according to the invention.

The invention also relates to a product comprising a compound of Formula (I) and an additional pharmaceutical agent, as a combined preparation for simultaneous, separate or sequential use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

The invention also relates to 6,7-dihydropyrazolo[1,5-a]pyrazine-4(5H)-one derivatives designed to bind irreversibly to the mGluR2 receptor.

DETAILED DESCRIPTION OF THE INVENTION

The present invention relates in particular to compounds of Formula (I) as defined hereinabove, and stereoisomeric forms thereof, wherein R$^1$ is phenyl or 2-pyridinyl, each optionally substituted with one or more substituents each independently selected from the group consisting of halo, C$_{1-4}$alkyl, monohalo-C$_{1-4}$alkyl, polyhalo-C$_{1-4}$alkyl, —C$_{1-4}$alkyl-OH, —CN, —C$_{1-4}$alkyl-O—C$_{1-4}$alkyl, C$_{3-7}$cycloalkyl, —O—C$_{1-4}$alkyl, monohalo-C$_{1-4}$alkyloxy, polyhalo-C$_{1-4}$alkyloxy, SF$_5$, C$_{1-4}$alkylthio, monohalo-C$_{1-4}$alkylthio and polyhalo-C$_{1-4}$alkylthio;

R$^2$ is selected from the group consisting of hydrogen; C$_{1-4}$alkyl; C$_{3-7}$cycloalkyl; Het$^1$; Aryl; —C(O)R$^5$; —C(O)Het$^2$; Het$^2$; and C$_{1-4}$alkyl substituted with one or more substituents each independently selected from the group consisting of C$_{3-7}$cycloalkyl, Aryl, Het$^1$ and Het$^2$; wherein R$^5$ is selected from the group consisting of hydrogen, C$_{1-4}$alkyl and C$_{3-7}$cycloalkyl;

Aryl is phenyl optionally substituted with one or more substituents each independently selected from the group consisting of halo, C$_{1-4}$alkyl, —O—C$_{1-4}$alkyl, —C$_{1-4}$alkyl-O—C$_{1-4}$alkyl and —SO$_2$—C$_{1-4}$alkyl;

Het$^1$ is selected from the group consisting of oxetanyl, tetrahydrofuranyl and tetrahydropyranyl;

Het$^2$ is (a) a 6-membered aromatic heterocyclyl substituent selected from the group consisting of pyridinyl, pyrimidinyl, pyrazinyl and pyridazinyl, each of which may be optionally substituted with one or more substituents each independently selected from the group consisting of halo, C$_{1-4}$alkyl, —CN, —OH, —O—C$_{1-4}$alkyl, —C(O)NR'R" and —NR'R"; or (b) a 5-membered aromatic heterocyclyl selected from the group consisting of thiazolyl, oxazolyl, 1H-pyrazolyl and 1H-imidazolyl, each of which may be optionally substituted with one or more substituents each independently selected from the group consisting of halo, C$_{1-4}$alkyl, —CN, —OH, —O—C$_{1-4}$alkyl, —C(O)NR'R" and —NR'R";

R' and R" are each independently selected from hydrogen and C$_{1-4}$alkyl; and

R$^3$ is selected from hydrogen and C$_{1-4}$alkyl;

R$^4$ is selected from the group consisting of hydrogen, C$_{1-4}$alkyl, monohalo-C$_{1-4}$alkyl, polyhalo-C$_{1-4}$alkyl, —C$_{1-4}$alkyl-O—C$_{1-4}$alkyl and —C$_{1-4}$alkyl-OH;

and the N-oxides and the pharmaceutically acceptable salts and the solvates thereof.

In an additional embodiment, the present invention relates to compounds of Formula (I) as defined hereinabove and stereoisomeric forms thereof, wherein $R^1$ is phenyl or 2-pyridinyl, each optionally substituted with one or two substituents each independently selected from the group consisting of halo, $C_{1-4}$alkyl, monohalo-$C_{1-4}$alkyl, polyhalo-$C_{1-4}$alkyl, —CN, —$C_{1-4}$alkyl-O—$C_{1-4}$alkyl, —O—$C_{1-4}$alkyl and monohalo-$C_{1-4}$alkyloxy and polyhalo-$C_{1-4}$alkyloxy;

$R^2$ is selected from the group consisting of hydrogen; $C_{1-4}$alkyl; $C_{3-7}$cycloalkyl;

Aryl; —C(O)$R^5$; —C(O)Het²; Het²; and $C_{1-4}$alkyl substituted with one or more substituents each independently selected from the group consisting of $C_{3-7}$cycloalkyl, Aryl, Het¹ and Het²; wherein $R^5$ is selected from the group consisting of hydrogen, $C_{1-4}$alkyl and $C_{3-7}$cycloalkyl;

Aryl is phenyl optionally substituted with a substituent selected from the group consisting of halo, $C_{1-4}$alkyl, —O—$C_{1-4}$alkyl and —SO₂—$C_{1-4}$alkyl;

Het¹ is selected from the group consisting of oxetanyl, tetrahydrofuranyl and tetrahydropyranyl;

Het² is (a) a 6-membered aromatic heterocyclyl substituent selected from the group consisting of pyridinyl, pyrimidinyl and pyrazinyl, each of which may be optionally substituted with one or two substituents each independently selected from the group consisting of halo, $C_{1-4}$alkyl, —O—$C_{1-4}$alkyl and —NR'R"; or (b) a 5-membered aromatic heterocyclyl selected from the group consisting of thiazolyl, oxazolyl and 1H-imidazolyl, each of which may be optionally substituted with a $C_{1-4}$alkyl substituent;

R' and R" are each independently selected from hydrogen and $C_{1-4}$alkyl; and $R^3$ is hydrogen;

$R^4$ is selected from the group consisting of hydrogen, $C_{1-4}$alkyl and —$C_{1-4}$alkyl-O—$C_{1-4}$alkyl;

and the N-oxides and the pharmaceutically acceptable salts and the solvates thereof.

In a further embodiment, the present invention relates to compounds of Formula (I) as defined hereinabove and stereoisomeric forms thereof, wherein $R^1$ is phenyl or 2-pyridinyl, each optionally substituted with one or two substituents each independently selected from the group consisting of halo, $C_{1-4}$alkyl, polyhalo-$C_{1-4}$alkyl, —$C_{1-4}$alkyl-O—$C_{1-4}$alkyl, —O—$C_{1-4}$alkyl and polyhalo-$C_{1-4}$alkyloxy;

$R^2$ is selected from the group consisting of Aryl; and Het²; wherein

Aryl is phenyl optionally substituted with a halo substituent;

Het¹ is selected from the group consisting of oxetanyl, tetrahydrofuranyl and tetrahydropyranyl;

Het² is (a) a 6-membered aromatic heterocyclyl substituent selected from the group consisting of pyridinyl, pyrimidinyl and pyrazinyl, each of which may be optionally substituted with one or two substituents each independently selected from the group consisting of halo, $C_{1-4}$alkyl, —O—$C_{1-4}$alkyl and NR'R"; or (b) a 5-membered aromatic heterocyclyl selected from the group consisting of thiazolyl, 1,2-oxazolyl, 1,3-oxazolyl and 1H-imidazolyl, each of which may be optionally substituted with a $C_{1-4}$alkyl substituent;

R' and R" are each hydrogen; and $R^3$ is hydrogen;

$R^4$ is selected from the group consisting of hydrogen, $C_{1-4}$alkyl and —$C_{1-4}$alkyl-O—$C_{1-4}$alkyl;

and the N-oxides and the pharmaceutically acceptable salts and the solvates thereof.

In a further embodiment, the present invention relates to compounds of Formula (I) as defined hereinabove and stereoisomeric forms thereof, wherein $R^1$ is phenyl or 2-pyridinyl, each optionally substituted with one or two substituents each independently selected from the group consisting of halo, $C_{1-4}$alkyl, polyhalo-$C_{1-4}$alkyl, —O—$C_{1-4}$alkyl and polyhalo-$C_{1-4}$alkyloxy;

$R^2$ is selected from the group consisting of Aryl; and Het²; wherein

Aryl is phenyl optionally substituted with a halo substituent;

Het¹ is selected from the group consisting of oxetanyl, tetrahydrofuranyl and tetrahydropyranyl;

Het² is (a) pyridinyl or pyrazinyl, each of which may be optionally substituted with one or two substituents each independently selected from the group consisting of halo, $C_{1-4}$alkyl, —O—$C_{1-4}$alkyl and NR'R"; or (b) a thiazolyl;

R' and R" are each hydrogen; and

>$CR^3R^4$ is selected from >CH(CH₃) and >CH(CH₂OCH₃);

and the N-oxides and the pharmaceutically acceptable salts and the solvates thereof.

In a further embodiment, the present invention relates to compounds of Formula (I) as defined hereinabove and stereoisomeric forms thereof, wherein $R^1$ is phenyl substituted with one or two substituents each independently selected from the group consisting of halo, $C_{1-4}$alkyl, polyhalo-$C_{1-4}$alkyl and —O—$C_{1-4}$alkyl;

$R^2$ is Het²; wherein

Het² is pyridinyl or pyrazinyl, each of which may be optionally substituted with one or two substituents each independently selected from the group consisting of halo, $C_{1-4}$alkyl, —O—$C_{1-4}$alkyl and NH₂;

>$CR^3R^4$ is >CH(CH₃);

and the N-oxides and the pharmaceutically acceptable salts and the solvates thereof.

In a further embodiment, the present invention relates to compounds of Formula (I) as defined herein wherein $R^3$ is hydrogen and $R^4$ is a substituent different from hydrogen having a configuration as depicted in the Formula (I') below, wherein the 6,7-dihydropyrazolo[1,5-a]pyrazin-4(5H)-one core, $R^1$ and $R^2$ are in the plane of the drawing and $R^4$ is projected above the plane of the drawing (bond shown with a bold wedge) and the rest of variables are as defined in Formula (I) herein

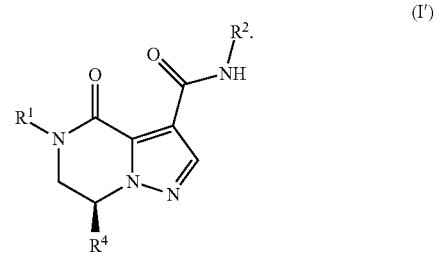

(I')

In a yet further embodiment, the present invention relates to compounds of Formula (I) as defined herein wherein $R^4$ is hydrogen and $R^3$ is a substituent different from hydrogen, for example a $C_{1-4}$alkyl substituent having a configuration as depicted in the Formula (I") below, wherein the 6,7-dihydropyrazolo[1,5-a]pyrazin-4(5H)-one core, $R^1$ and $R^2$ are in the plane of the drawing and R³ is projected above the plane of the drawing (bond shown with a bold wedge), and the rest of variables are as defined in Formula (I) herein

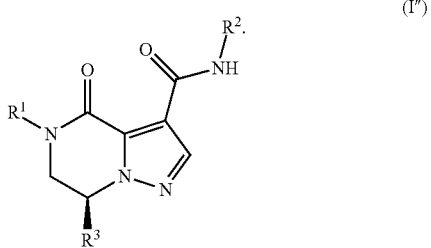

(I″)

Specific compounds according to the invention include:
(7S)-7-methyl-4-oxo-5-[4-(trifluoromethyl)phenyl]-6,7-dihydropyrazolo[1,5-a]pyrazine-3-carboxamide;
(7S)—N-(6-fluoro-3-pyridyl)-7-methyl-4-oxo-5-[4-(trifluoromethyl)phenyl]-6,7-dihydropyrazolo[1,5-a]pyrazine-3-carboxamide;
(7S)—N-(6-amino-3-pyridyl)-7-methyl-4-oxo-5-[4-(trifluoromethyl)phenyl]-6,7-dihydropyrazolo[1,5-a]pyrazine-3-carboxamide;
(7S)—N-formyl-7-methyl-4-oxo-5-[4-(trifluoromethyl)phenyl]-6,7-dihydropyrazolo[1,5-a]pyrazine-3-carboxamide;
(7S)-7-methyl-N-(2-methyl-4-pyridyl)-4-oxo-5-[4-(trifluoromethyl)phenyl]-6,7-dihydropyrazolo[1,5-a]pyrazine-3-carboxamide;
(7S)-7-methyl-N-(2-methylpyridine-4-carbonyl)-4-oxo-5-[4-(trifluoromethyl)phenyl]-6,7-dihydropyrazolo[1,5-a]pyrazine-3-carboxamide;
(7S)—N,7-dimethyl-4-oxo-5-[4-(trifluoromethyl)phenyl]-6,7-dihydropyrazolo[1,5-a]pyrazine-3-carboxamide;
(7S)-7-methyl-4-oxo-N-tetrahydropyran-4-yl-5-[4-(trifluoromethyl)phenyl]-6,7-dihydropyrazolo[1,5-a]pyrazine-3-carboxamide;
(7S)-7-methyl-4-oxo-N-phenyl-5-[4-(trifluoromethyl)phenyl]-6,7-dihydropyrazolo[1,5-a]pyrazine-3-carboxamide;
(7S)—N-tert-butyl-7-methyl-4-oxo-5-[4-(trifluoromethyl)phenyl]-6,7-dihydropyrazolo[1,5-a]pyrazine-3-carboxamide;
(7S)—N-cyclohexyl-7-methyl-4-oxo-5-[4-(trifluoromethyl)phenyl]-6,7-dihydropyrazolo[1,5-a]pyrazine-3-carboxamide;
(7S)—N-benzyl-7-methyl-4-oxo-5-[4-(trifluoromethyl)phenyl]-6,7-dihydropyrazolo[1,5-a]pyrazine-3-carboxamide;
(7S)—N-[(6-amino-3-pyridyl)methyl]-7-methyl-4-oxo-5-[4-(trifluoromethyl)phenyl]-6,7-dihydropyrazolo[1,5-a]pyrazine-3-carboxamide;
(7S)—N-(4-fluorophenyl)-7-methyl-4-oxo-5-[4-(trifluoromethyl)phenyl]-6,7-dihydropyrazolo[1,5-a]pyrazine-3-carboxamide;
(7S)—N-(cyclopentylmethyl)-7-methyl-4-oxo-5-[4-(trifluoromethyl)phenyl]-6,7-dihydropyrazolo[1,5-a]pyrazine-3-carboxamide;
(7S)-7-methyl-4-oxo-N-(2-pyridyl)-5-[4-(trifluoromethyl)phenyl]-6,7-dihydropyrazolo[1,5-a]pyrazine-3-carboxamide;
(7S)-7-methyl-N-(2-methylpyrimidin-5-yl)-4-oxo-5-[4-(trifluoromethyl)phenyl]-6,7-dihydropyrazolo[1,5-a]pyrazine-3-carboxamide;
(7S)-7-methyl-N-[(2-methyl-4-pyridyl)methyl]-4-oxo-5-[4-(trifluoromethyl)phenyl]-6,7-dihydropyrazolo[1,5-a]pyrazine-3-carboxamide;
(7S)—N-(cyclopropylmethyl)-7-methyl-4-oxo-5-[4-(trifluoromethyl)phenyl]-6,7-dihydropyrazolo[1,5-a]pyrazine-3-carboxamide;
(7S)-5-(3,4-dichlorophenyl)-N-(6-fluoro-3-pyridyl)-7-methyl-4-oxo-6,7-dihydropyrazolo[1,5-a]pyrazine-3-carboxamide;
(7S)-7-methyl-N-(3-methylsulfonylphenyl)-4-oxo-5-[4-(trifluoromethyl)phenyl]-6,7-dihydropyrazolo[1,5-a]pyrazine-3-carboxamide;
(7S)-7-methyl-N-(4-methylsulfonylphenyl)-4-oxo-5-[4-(trifluoromethyl)phenyl]-6,7-dihydropyrazolo[1,5-a]pyrazine-3-carboxamide;
(7*S)—N-(1-cyclopropylethyl)-7-methyl-4-oxo-5-[4-(trifluoromethyl)phenyl]-6,7-dihydropyrazolo[1,5-a]pyrazine-3-carboxamide;
(7S)-5-(3,4-dichlorophenyl)-7-methyl-N-(2-methyl-4-pyridyl)-4-oxo-6,7-dihydropyrazolo[1,5-a]pyrazine-3-carboxamide;
(7S)-5-(4-chlorophenyl)-7-methyl-N-(2-methyl-4-pyridyl)-4-oxo-6,7-dihydropyrazolo[1,5-a]pyrazine-3-carboxamide;
(7S)-7-methyl-N-(2-methyl-4-pyridyl)-5-[3-methyl-4-(trifluoromethyl)phenyl]-4-oxo-6,7-dihydropyrazolo[1,5-a]pyrazine-3-carboxamide;
(7S)-5-[3-cyano-4-(trifluoromethyl)phenyl]-7-methyl-N-(2-methyl-4-pyridyl)-4-oxo-6,7-dihydropyrazolo[1,5-a]pyrazine-3-carboxamide;
(7S)-5-[3-methoxy-4-(trifluoromethyl)phenyl]-7-methyl-N-(2-methyl-4-pyridyl)-4-oxo-6,7-dihydropyrazolo[1,5-a]pyrazine-3-carboxamide;
(7S)-7-methyl-N-(2-methyl-4-pyridyl)-4-oxo-5-[5-(trifluoromethyl)-2-pyridyl]-6,7-dihydropyrazolo[1,5-a]pyrazine-3-carboxamide;
(7S)-5-[3-fluoro-4-(trifluoromethyl)phenyl]-7-methyl-N-(2-methyl-4-pyridyl)-4-oxo-6,7-dihydropyrazolo[1,5-a]pyrazine-3-carboxamide;
(7S)—N-(cyclobutylmethyl)-7-methyl-4-oxo-5-[4-(trifluoromethyl)phenyl]-6,7-dihydropyrazolo[1,5-a]pyrazine-3-carboxamide;
(7S)-7-methyl-4-oxo-N-(tetrahydrofuran-2-ylmethyl)-5-[4-(trifluoromethyl)phenyl]-6,7-dihydropyrazolo[1,5-a]pyrazine-3-carboxamide;
(7S)-7-methyl-4-oxo-N-(tetrahydropyran-4-ylmethyl)-5-[4-(trifluoromethyl)phenyl]-6,7-dihydropyrazolo[1,5-a]pyrazine-3-carboxamide;
(7S)—N-(2-methoxyphenyl)-5-[6-methoxy-5-(trifluoromethyl)-2-pyridyl]-7-methyl-4-oxo-6,7-dihydropyrazolo[1,5-a]pyrazine-3-carboxamide;
(7S)-5-(5-chloro-6-methoxy-2-pyridyl)-7-methyl-4-oxo-N-phenyl-6,7-dihydropyrazolo[1,5-a]pyrazine-3-carboxamide;
(7S)—N-(3-methoxyphenyl)-5-[6-methoxy-5-(trifluoromethyl)-2-pyridyl]-7-methyl-4-oxo-6,7-dihydropyrazolo[1,5-a]pyrazine-3-carboxamide;
(7S)-5-[6-methoxy-5-(trifluoromethyl)-2-pyridyl]-7-methyl-4-oxo-N-phenyl-6,7-dihydropyrazolo[1,5-a]pyrazine-3-carboxamide;
(7S)—N-(4-methoxyphenyl)-5-[6-methoxy-5-(trifluoromethyl)-2-pyridyl]-7-methyl-4-oxo-6,7-dihydropyrazolo[1,5-a]pyrazine-3-carboxamide;
(7S)-7-methyl-4-oxo-N-(tetrahydrofuran-3-ylmethyl)-5-[4-(trifluoromethyl)phenyl]-6,7-dihydropyrazolo[1,5-a]pyrazine-3-carboxamide;
(7S)-7-methyl-4-oxo-N-(4-pyridyl)-5-[4-(trifluoromethyl)phenyl]-6,7-dihydropyrazolo[1,5-a]pyrazine-3-carboxamide;

(7S)—N-(5-methoxy-3-pyridyl)-7-methyl-4-oxo-5-[4-(trifluoromethyl)phenyl]-6,7-dihydropyrazolo[1,5-a]pyrazine-3-carboxamide;

(7S)-7-methyl-4-oxo-N-(3-pyridyl)-5-[4-(trifluoromethyl)phenyl]-6,7-dihydropyrazolo[1,5-a]pyrazine-3-carboxamide;

(7S)-7-methyl-N-(2-methyl-3-pyridyl)-4-oxo-5-[4-(trifluoromethyl)phenyl]-6,7-dihydropyrazolo[1,5-a]pyrazine-3-carboxamide;

(7S)—N-(3-fluoro-4-pyridyl)-7-methyl-4-oxo-5-[4-(trifluoromethyl)phenyl]-6,7-dihydropyrazolo[1,5-a]pyrazine-3-carboxamide;

(7S)-7-methyl-N-(5-methyl-3-pyridyl)-4-oxo-5-[4-(trifluoromethyl)phenyl]-6,7-dihydropyrazolo[1,5-a]pyrazine-3-carboxamide;

(7S)-7-methyl-N-(4-methyl-3-pyridyl)-4-oxo-5-[4-(trifluoromethyl)phenyl]-6,7-dihydropyrazolo[1,5-a]pyrazine-3-carboxamide;

(7S)-5-[3-(methoxymethyl)-4-(trifluoromethyl)phenyl]-7-methyl-N-(2-methyl-4-pyridyl)-4-oxo-6,7-dihydropyrazolo[1,5-a]pyrazine-3-carboxamide;

(7S)—N-(5-fluoro-3-pyridyl)-7-methyl-4-oxo-5-[4-(trifluoromethyl)phenyl]-6,7-dihydropyrazolo[1,5-a]pyrazine-3-carboxamide;

(7S)-5-[3-chloro-4-(difluoromethyl)phenyl]-7-methyl-N-(2-methyl-4-pyridyl)-4-oxo-6,7-dihydropyrazolo[1,5-a]pyrazine-3-carboxamide;

(7S)—N-(6-methoxy-2-pyridyl)-7-methyl-4-oxo-5-[4-(trifluoromethyl)phenyl]-6,7-dihydropyrazolo[1,5-a]pyrazine-3-carboxamide;

(7S)—N-(cyclobutanecarbonyl)-7-methyl-4-oxo-5-[4-(trifluoromethyl)phenyl]-6,7-dihydropyrazolo[1,5-a]pyrazine-3-carboxamide;

(7S)—N-(5-fluoro-2-pyridyl)-7-methyl-4-oxo-5-[4-(trifluoromethyl)phenyl]-6,7-dihydropyrazolo[1,5-a]pyrazine-3-carboxamide;

(7S)-7-methyl-4-oxo-N-pyrimidin-2-yl-5-[4-(trifluoromethyl)phenyl]-6,7-dihydropyrazolo[1,5-a]pyrazine-3-carboxamide;

(7S)—N-(5-methoxy-2-pyridyl)-7-methyl-4-oxo-5-[4-(trifluoromethyl)phenyl]-6,7-dihydropyrazolo[1,5-a]pyrazine-3-carboxamide;

(7S)-5-[3-(methoxymethyl)-4-(trifluoromethyl)phenyl]-7-methyl-4-oxo-N-(2-pyridyl)-6,7-dihydropyrazolo[1,5-a]pyrazine-3-carboxamide;

7-(methoxymethyl)-N-(2-methyl-4-pyridyl)-4-oxo-5-[4-(trifluoromethyl)phenyl]-6,7-dihydropyrazolo[1,5-a]pyrazine-3-carboxamide;

(7S)—N-(3-fluoro-2-pyridyl)-7-methyl-4-oxo-5-[4-(trifluoromethyl)phenyl]-6,7-dihydropyrazolo[1,5-a]pyrazine-3-carboxamide;

(7S)—N-(3-methoxy-2-pyridyl)-7-methyl-4-oxo-5-[4-(trifluoromethyl)phenyl]-6,7-dihydropyrazolo[1,5-a]pyrazine-3-carboxamide;

(7S)-5-(3,4-dichlorophenyl)-7-methyl-4-oxo-N-(2-pyridyl)-6,7-dihydropyrazolo[1,5-a]pyrazine-3-carboxamide;

(7S)-7-methyl-5-[3-methyl-4-(trifluoromethyl)phenyl]-4-oxo-N-(2-pyridyl)-6,7-dihydropyrazolo[1,5-a]pyrazine-3-carboxamide;

(7S)-7-methyl-N-(oxetan-3-yl)-4-oxo-5-[4-(trifluoromethyl)phenyl]-6,7-dihydropyrazolo[1,5-a]pyrazine-3-carboxamide;

(7S)—N-cyclobutyl-7-methyl-4-oxo-5-[4-(trifluoromethyl)phenyl]-6,7-dihydropyrazolo[1,5-a]pyrazine-3-carboxamide;

(7*R)-7-(methoxymethyl)-N-(2-methyl-4-pyridyl)-4-oxo-5-[4-(trifluoromethyl)phenyl]-6,7-dihydropyrazolo[1,5-a]pyrazine-3-carboxamide;

(7*S)-7-(methoxymethyl)-N-(2-methyl-4-pyridyl)-4-oxo-5-[4-(trifluoromethyl)phenyl]-6,7-dihydropyrazolo[1,5-a]pyrazine-3-carboxamide;

(7S)-5-[3-chloro-4-(trifluoromethyl)phenyl]-7-methyl-4-oxo-N-(2-pyridyl)-6,7-dihydropyrazolo[1,5-a]pyrazine-3-carboxamide;

(7S)—N-(2,6-dimethyl-4-pyridyl)-7-methyl-4-oxo-5-[4-(trifluoromethyl)phenyl]-6,7-dihydropyrazolo[1,5-a]pyrazine-3-carboxamide;

(7S)-7-methyl-4-oxo-N-pyrazin-2-yl-5-[4-(trifluoromethyl)phenyl]-6,7-dihydropyrazolo[1,5-a]pyrazine-3-carboxamide;

(7S)-5-[3-fluoro-4-(trifluoromethyl)phenyl]-7-methyl-4-oxo-N-(2-pyridyl)-6,7-dihydropyrazolo[1,5-a]pyrazine-3-carboxamide;

(7S)—N-acetyl-7-methyl-4-oxo-5-[4-(trifluoromethyl)phenyl]-6,7-dihydropyrazolo[1,5-a]pyrazine-3-carboxamide;

(7S)-5-[4-chloro-3-(difluoromethoxy)phenyl]-7-methyl-N-(2-methyl-4-pyridyl)-4-oxo-6,7-dihydropyrazolo[1,5-a]pyrazine-3-carboxamide;

(7S)-7-methyl-N-(2-methyl-4-pyridyl)-4-oxo-5-phenyl-6,7-dihydropyrazolo[1,5-a]pyrazine-3-carboxamide;

(7S)-7-methyl-N-oxazol-2-yl-4-oxo-5-[4-(trifluoromethyl)phenyl]-6,7-dihydropyrazolo[1,5-a]pyrazine-3-carboxamide;

(7S)-5-[3-(fluoromethyl)-4-(trifluoromethyl)phenyl]-7-methyl-4-oxo-N-(3-pyridyl)-6,7-dihydropyrazolo[1,5-a]pyrazine-3-carboxamide;

(7S)-5-[3-(fluoromethyl)-4-(trifluoromethyl)phenyl]-7-methyl-N-(2-methyl-4-pyridyl)-4-oxo-6,7-dihydropyrazolo[1,5-a]pyrazine-3-carboxamide;

(7S)-7-methyl-4-oxo-N-thiazol-2-yl-5-[4-(trifluoromethyl)phenyl]-6,7-dihydropyrazolo[1,5-a]pyrazine-3-carboxamide;

(7S)-7-methyl-4-oxo-N-pyrimidin-4-yl-5-[4-(trifluoromethyl)phenyl]-6,7-dihydropyrazolo[1,5-a]pyrazine-3-carboxamide;

(7S)-7-methyl-N-(6-methyl-2-pyridyl)-4-oxo-5-[4-(trifluoromethyl)phenyl]-6,7-dihydropyrazolo[1,5-a]pyrazine-3-carboxamide;

(7S)—N-(1H-imidazol-2-yl)-7-methyl-4-oxo-5-[4-(trifluoromethyl)phenyl]-6,7-dihydropyrazolo[1,5-a]pyrazine-3-carboxamide;

(7S)—N-(3-methoxy-4-pyridyl)-7-methyl-4-oxo-5-[4-(trifluoromethyl)phenyl]-6,7-dihydropyrazolo[1,5-a]pyrazine-3-carboxamide;

(7S)-5-[3-(fluoromethyl)-4-(trifluoromethyl)phenyl]-7-methyl-4-oxo-N-(4-pyridyl)-6,7-dihydropyrazolo[1,5-a]pyrazine-3-carboxamide;

(7S)-5-[3-chloro-4-(trifluoromethyl)phenyl]-7-methyl-4-oxo-N-(3-pyridyl)-6,7-dihydropyrazolo[1,5-a]pyrazine-3-carboxamide;

(7S)-7-methyl-N-(3-methyl-2-pyridyl)-4-oxo-5-[4-(trifluoromethyl)phenyl]-6,7-dihydropyrazolo[1,5-a]pyrazine-3-carboxamide;

(7S)-5-[3-chloro-4-(trifluoromethyl)phenyl]-7-methyl-4-oxo-6,7-dihydropyrazolo[1,5-a]pyrazine-3-carboxamide;

(7S)-5-(3,4-dichlorophenyl)-N-(5-fluoro-2-pyridyl)-7-methyl-4-oxo-6,7-dihydropyrazolo[1,5-a]pyrazine-3-carboxamide;

(7S)-5-(3,4-dichlorophenyl)-7-methyl-4-oxo-N-(3-pyridyl)-6,7-dihydropyrazolo[1,5-a]pyrazine-3-carboxamide;

(7S)-7-methyl-N-(4-methyl-2-pyridyl)-4-oxo-5-[4-(trifluoromethyl)phenyl]-6,7-dihydropyrazolo[1,5-a]pyrazine-3-carboxamide;
(7S)-7-methyl-N-(5-methyl-3-pyridyl)-5-[3-methyl-4-(trifluoromethyl)phenyl]-4-oxo-6,7-dihydropyrazolo[1,5-a]pyrazine-3-carboxamide;
(7S)-7-methyl-5-[3-methyl-4-(trifluoromethyl)phenyl]-4-oxo-N-(3-pyridyl)-6,7-dihydropyrazolo[1,5-a]pyrazine-3-carboxamide;
(7S)-5-[3-chloro-4-(trifluoromethyl)phenyl]-7-methyl-4-oxo-N-pyrazin-2-yl-6,7-dihydropyrazolo[1,5-a]pyrazine-3-carboxamide;
(7S)-7-methyl-5-[3-methyl-4-(trifluoromethyl)phenyl]-4-oxo-N-pyrazin-2-yl-6,7-dihydropyrazolo[1,5-a]pyrazine-3-carboxamide;
(7S)-5-[3-chloro-4-(trifluoromethyl)phenyl]-7-methyl-N-(2-methyl-4-pyridyl)-4-oxo-6,7-dihydropyrazolo[1,5-a]pyrazine-3-carboxamide;
(7S)-7-methyl-5-[3-methyl-4-(trifluoromethyl)phenyl]-4-oxo-6,7-dihydropyrazolo[1,5-a]pyrazine-3-carboxamide;
(7S)—N-(5-fluoro-4-methyl-3-pyridyl)-7-methyl-4-oxo-5-[4-(trifluoromethyl)phenyl]-6,7-dihydropyrazolo[1,5-a]pyrazine-3-carboxamide;
(7S)-5-[3-chloro-4-(trifluoromethyl)phenyl]-N-(5-fluoro-4-methyl-3-pyridyl)-7-methyl-4-oxo-6,7-dihydropyrazolo[1,5-a]pyrazine-3-carboxamide;
(7S)-5-(3,4-dichlorophenyl)-7-methyl-4-oxo-N-pyrazin-2-yl-6,7-dihydropyrazolo[1,5-a]pyrazine-3-carboxamide;
(7S)-5-(3,4-dichlorophenyl)-N-(2,6-dimethyl-4-pyridyl)-7-methyl-4-oxo-6,7-dihydropyrazolo[1,5-a]pyrazine-3-carboxamide;
(7S)-5-[3-chloro-4-(trifluoromethyl)phenyl]-N-(2,6-dimethyl-4-pyridyl)-7-methyl-4-oxo-6,7-dihydropyrazolo[1,5-a]pyrazine-3-carboxamide;
(7S)-5-[3-chloro-4-(trifluoromethyl)phenyl]-N-(5-fluoro-2-pyridyl)-7-methyl-4-oxo-6,7-dihydropyrazolo[1,5-a]pyrazine-3-carboxamide;
(7S)-5-[3-chloro-4-(trifluoromethyl)phenyl]-N-(4,5-dimethyl-3-pyridyl)-7-methyl-4-oxo-6,7-dihydropyrazolo[1,5-a]pyrazine-3-carboxamide;
(7S)—N-(5-methoxy-4-methyl-3-pyridyl)-7-methyl-4-oxo-5-[4-(trifluoromethyl)phenyl]-6,7-dihydropyrazolo[1,5-a]pyrazine-3-carboxamide;
(7S)-5-[3-chloro-4-(trifluoromethyl)phenyl]-N-(5-methoxy-4-methyl-3-pyridyl)-7-methyl-4-oxo-6,7-dihydropyrazolo[1,5-a]pyrazine-3-carboxamide;
(7S)—N-(2,6-dimethyl-4-pyridyl)-7-methyl-5-[3-methyl-4-(trifluoromethyl)phenyl]-4-oxo-6,7-dihydropyrazolo[1,5-a]pyrazine-3-carboxamide;
(7S)—N-(5-fluoro-2-pyridyl)-7-methyl-5-[3-methyl-4-(trifluoromethyl)phenyl]-4-oxo-6,7-dihydropyrazolo[1,5-a]pyrazine-3-carboxamide;
(7S)-5-(3,4-dichlorophenyl)-7-methyl-4-oxo-6,7-dihydropyrazolo[1,5-a]pyrazine-3-carboxamide;
(7S)-5-(3,4-dichlorophenyl)-7-methyl-N-(5-methyl-3-pyridyl)-4-oxo-6,7-dihydropyrazolo[1,5-a]pyrazine-3-carboxamide;
(7S)—N-(5-fluoro-3-pyridyl)-7-methyl-5-[3-methyl-4-(trifluoromethyl)phenyl]-4-oxo-6,7-dihydropyrazolo[1,5-a]pyrazine-3-carboxamide;
(7S)—N-(5-methoxy-3-pyridyl)-7-methyl-5-[3-methyl-4-(trifluoromethyl)phenyl]-4-oxo-6,7-dihydropyrazolo[1,5-a]pyrazine-3-carboxamide;
(7S)-5-(4-chlorophenyl)-7-methyl-4-oxo-N-(3-pyridyl)-6,7-dihydropyrazolo[1,5-a]pyrazine-3-carboxamide;
(7S)-5-[3-fluoro-4-(trifluoromethyl)phenyl]-7-methyl-4-oxo-N-(3-pyridyl)-6,7-dihydropyrazolo[1,5-a]pyrazine-3-carboxamide;
(7S)—N-(5-fluoro-2-pyridyl)-5-[3-methoxy-4-(trifluoromethyl)phenyl]-7-methyl-4-oxo-6,7-dihydropyrazolo[1,5-a]pyrazine-3-carboxamide;
(7S)-5-(3,4-dichlorophenyl)-N-(5-methoxy-3-pyridyl)-7-methyl-4-oxo-6,7-dihydropyrazolo[1,5-a]pyrazine-3-carboxamide;
(7S)-7-methyl-N-(4-methyl-3-pyridyl)-5-[3-methyl-4-(trifluoromethyl)phenyl]-4-oxo-6,7-dihydropyrazolo[1,5-a]pyrazine-3-carboxamide;
(7S)-5-[3-methoxy-4-(trifluoromethyl)phenyl]-7-methyl-N-(4-methyl-3-pyridyl)-4-oxo-6,7-dihydropyrazolo[1,5-a]pyrazine-3-carboxamide;
(7S)—N-(5-fluoro-3-pyridyl)-5-[3-methoxy-4-(trifluoromethyl)phenyl]-7-methyl-4-oxo-6,7-dihydropyrazolo[1,5-a]pyrazine-3-carboxamide;
(7S)-5-(3,4-dichlorophenyl)-N-(5-fluoro-3-pyridyl)-7-methyl-4-oxo-6,7-dihydropyrazolo[1,5-a]pyrazine-3-carboxamide;
(7S)—N-(5-fluoro-2-pyridyl)-5-[3-fluoro-4-(trifluoromethyl)phenyl]-7-methyl-4-oxo-6,7-dihydropyrazolo[1,5-a]pyrazine-3-carboxamide;
(7S)-5-(3,4-dichlorophenyl)-7-methyl-N-(4-methyl-3-pyridyl)-4-oxo-6,7-dihydropyrazolo[1,5-a]pyrazine-3-carboxamide;
(7S)-5-[3-methoxy-4-(trifluoromethyl)phenyl]-7-methyl-N-(5-methyl-3-pyridyl)-4-oxo-6,7-dihydropyrazolo[1,5-a]pyrazine-3-carboxamide;
(7S)-5-[3-chloro-4-(trifluoromethyl)phenyl]-7-methyl-N-(3-methylisoxazol-5-yl)-4-oxo-6,7-dihydropyrazolo[1,5-a]pyrazine-3-carboxamide;
(7S)—N-(5-methoxy-3-pyridyl)-5-[3-methoxy-4-(trifluoromethyl)phenyl]-7-methyl-4-oxo-6,7-dihydropyrazolo[1,5-a]pyrazine-3-carboxamide;
(7S)-5-[3-fluoro-4-(trifluoromethyl)phenyl]-7-methyl-4-oxo-N-pyrazin-2-yl-6,7-dihydropyrazolo[1,5-a]pyrazine-3-carboxamide;
(7S)-5-[3-chloro-4-(trifluoromethyl)phenyl]-N-(5-fluoro-3-pyridyl)-7-methyl-4-oxo-6,7-dihydropyrazolo[1,5-a]pyrazine-3-carboxamide;
(7S)-5-[3-methoxy-4-(trifluoromethyl)phenyl]-7-methyl-4-oxo-N-pyrazin-2-yl-6,7-dihydropyrazolo[1,5-a]pyrazine-3-carboxamide;
(7S)—N-(5-fluoro-3-pyridyl)-5-[3-fluoro-4-(trifluoromethyl)phenyl]-7-methyl-4-oxo-6,7-dihydropyrazolo[1,5-a]pyrazine-3-carboxamide;
(7S)-5-[3-methoxy-4-(trifluoromethyl)phenyl]-7-methyl-4-oxo-6,7-dihydropyrazolo[1,5-a]pyrazine-3-carboxamide;
(7S)—N-(5-fluoro-4-methyl-3-pyridyl)-5-[3-fluoro-4-(trifluoromethyl)phenyl]-7-methyl-4-oxo-6,7-dihydropyrazolo[1,5-a]pyrazine-3-carboxamide;
(7S)—N-(5-fluoro-4-methyl-3-pyridyl)-7-methyl-5-[3-methyl-4-(trifluoromethyl)phenyl]-4-oxo-6,7-dihydropyrazolo[1,5-a]pyrazine-3-carboxamide;
(7S)-5-(3,4-dichlorophenyl)-N-(5-fluoro-4-methyl-3-pyridyl)-7-methyl-4-oxo-6,7-dihydropyrazolo[1,5-a]pyrazine-3-carboxamide;
(7S)-5-(4-chlorophenyl)-N-(5-fluoro-4-methyl-3-pyridyl)-7-methyl-4-oxo-6,7-dihydropyrazolo[1,5-a]pyrazine-3-carboxamide;
(7S)-5-(4-chloro-3-methyl-phenyl)-N-(5-fluoro-4-methyl-3-pyridyl)-7-methyl-4-oxo-6,7-dihydropyrazolo[1,5-a]pyrazine-3-carboxamide;

(7S)—N-(2,6-dimethyl-4-pyridyl)-5-[3-methoxy-4-(trifluoromethyl)phenyl]-7-methyl-4-oxo-6,7-dihydropyrazolo[1,5-a]pyrazine-3-carboxamide;

(7S)-5-[3-fluoro-4-(trifluoromethyl)phenyl]-7-methyl-N-(5-methyl-3-pyridyl)-4-oxo-6,7-dihydropyrazolo[1,5-a]pyrazine-3-carboxamide;

(7S)-5-[3-chloro-4-(trifluoromethyl)phenyl]-N-(5-methoxy-3-pyridyl)-7-methyl-4-oxo-6,7-dihydropyrazolo[1,5-a]pyrazine-3-carboxamide;

(7S)-7-methyl-N-(6-methylpyrazin-2-yl)-4-oxo-5-[4-(trifluoromethyl)phenyl]-6,7-dihydropyrazolo[1,5-a]pyrazine-3-carboxamide;

(7S)-5-(4-chlorophenyl)-7-methyl-N-(4-methyl-3-pyridyl)-4-oxo-6,7-dihydropyrazolo[1,5-a]pyrazine-3-carboxamide;

(7S)—N-(2,6-dimethyl-4-pyridyl)-5-[3-fluoro-4-(trifluoromethyl)phenyl]-7-methyl-4-oxo-6,7-dihydropyrazolo[1,5-a]pyrazine-3-carboxamide;

(7S)-5-[3-chloro-4-(trifluoromethyl)phenyl]-7-methyl-N-(4-methyl-3-pyridyl)-4-oxo-6,7-dihydropyrazolo[1,5-a]pyrazine-3-carboxamide;

(7S)-5-(4-chloro-3-methyl-phenyl)-7-methyl-N-(4-methyl-3-pyridyl)-4-oxo-6,7-dihydropyrazolo[1,5-a]pyrazine-3-carboxamide;

(7S)-5-(4-chloro-3-methyl-phenyl)-N-(5-fluoro-3-pyridyl)-7-methyl-4-oxo-6,7-dihydropyrazolo[1,5-a]pyrazine-3-carboxamide;

(7S)-5-[3-chloro-4-(trifluoromethyl)phenyl]-7-methyl-N-(5-methyl-3-pyridyl)-4-oxo-6,7-dihydropyrazolo[1,5-a]pyrazine-3-carboxamide;

(7S)-5-(4-chlorophenyl)-N-(5-fluoro-3-pyridyl)-7-methyl-4-oxo-6,7-dihydropyrazolo[1,5-a]pyrazine-3-carboxamide;

(7S)-5-[3-fluoro-4-(trifluoromethyl)phenyl]-7-methyl-4-oxo-6,7-dihydropyrazolo[1,5-a]pyrazine-3-carboxamide;

(7S)-5-[3-fluoro-4-(trifluoromethyl)phenyl]-7-methyl-N-(4-methyl-3-pyridyl)-4-oxo-6,7-dihydropyrazolo[1,5-a]pyrazine-3-carboxamide;

(7S)-5-(4-chlorophenyl)-7-methyl-4-oxo-6,7-dihydropyrazolo[1,5-a]pyrazine-3-carboxamide;

7-(methoxymethyl)-4-oxo-N-pyrazin-2-yl-5-[4-(trifluoromethyl)phenyl]-6,7-dihydropyrazolo[1,5-a]pyrazine-3-carboxamide;

(7S)-5-(4-chlorophenyl)-7-methyl-4-oxo-N-pyrazin-2-yl-6,7-dihydropyrazolo[1,5-a]pyrazine-3-carboxamide;

(7S)-5-(4-chloro-3-methyl-phenyl)-7-methyl-4-oxo-N-pyrazin-2-yl-6,7-dihydropyrazolo[1,5-a]pyrazine-3-carboxamide;

(7S)-5-(4-chloro-3-methyl-phenyl)-N-(2,6-dimethyl-4-pyridyl)-7-methyl-4-oxo-6,7-dihydropyrazolo[1,5-a]pyrazine-3-carboxamide;

(7R*)-7-(methoxymethyl)-4-oxo-N-(3-pyridyl)-5-[4-(trifluoromethyl)phenyl]-6,7-dihydropyrazolo[1,5-a]pyrazine-3-carboxamide;

(7S*)-7-(methoxymethyl)-4-oxo-N-(3-pyridyl)-5-[4-(trifluoromethyl)phenyl]-6,7-dihydropyrazolo[1,5-a]pyrazine-3-carboxamide;

(7R*)-5-[3-chloro-4-(trifluoromethyl)phenyl]-7-(methoxymethyl)-4-oxo-N-(3-pyridyl)-6,7-dihydropyrazolo[1,5-a]pyrazine-3-carboxamide;

(7S*)-5-[3-chloro-4-(trifluoromethyl)phenyl]-7-(methoxymethyl)-4-oxo-N-(3-pyridyl)-6,7-dihydropyrazolo[1,5-a]pyrazine-3-carboxamide;

(7R*)-7-(methoxymethyl)-4-oxo-N-pyrazin-2-yl-5-[4-(trifluoromethyl)phenyl]-6,7-dihydropyrazolo[1,5-a]pyrazine-3-carboxamide;

(7S*)-7-(methoxymethyl)-4-oxo-N-pyrazin-2-yl-5-[4-(trifluoromethyl)phenyl]-6,7-dihydropyrazolo[1,5-a]pyrazine-3-carboxamide;

4-oxo-N-(3-pyridyl)-5-[4-(trifluoromethyl)phenyl]-6,7-dihydropyrazolo[1,5-a]pyrazine-3-carboxamide;

(7S)-5-[3-chloro-4-(trifluoromethoxy)phenyl]-7-methyl-4-oxo-N-(3-pyridyl)-6,7-dihydropyrazolo[1,5-a]pyrazine-3-carboxamide;

(7S)—N-[2-(fluoromethyl)-4-pyridyl]-7-methyl-4-oxo-5-[4-(trifluoromethyl)phenyl]-6,7-dihydropyrazolo[1,5-a]pyrazine-3-carboxamide;

(7S)—N-[2-(hydroxymethyl)-4-pyridyl]-7-methyl-4-oxo-5-[4-(trifluoromethyl)phenyl]-6,7-dihydropyrazolo[1,5-a]pyrazine-3-carboxamide;

(7S)—N-[2-(methoxymethyl)-4-pyridyl]-7-methyl-4-oxo-5-[4-(trifluoromethyl)phenyl]-6,7-dihydropyrazolo[1,5-a]pyrazine-3-carboxamide;

(7S)—N-[5-(hydroxymethyl)-3-pyridyl]-7-methyl-4-oxo-5-[4-(trifluoromethyl)phenyl]-6,7-dihydropyrazolo[1,5-a]pyrazine-3-carboxamide;

(7S)—N-[4-(hydroxymethyl)-3-pyridyl]-7-methyl-4-oxo-5-[4-(trifluoromethyl)phenyl]-6,7-dihydropyrazolo[1,5-a]pyrazine-3-carboxamide;

(7S)-5-(3,4-dichlorophenyl)-N-(6-fluoropyrazin-2-yl)-7-methyl-4-oxo-6,7-dihydropyrazolo[1,5-a]pyrazine-3-carboxamide;

(7S)—N-(6-fluoropyrazin-2-yl)-7-methyl-4-oxo-5-[4-(trifluoromethyl)phenyl]-6,7-dihydropyrazolo[1,5-a]pyrazine-3-carboxamide;

5-[3-chloro-4-(trifluoromethyl)phenyl]-7-(methoxymethyl)-4-oxo-N-(3-pyridyl)-6,7-dihydropyrazolo[1,5-a]pyrazine-3-carboxamide;

7-(methoxymethyl)-4-oxo-N-(3-pyridyl)-5-[4-(trifluoromethyl)phenyl]-6,7-dihydropyrazolo[1,5-a]pyrazine-3-carboxamide;

(7S)-5-(4-chloro-3-methyl-phenyl)-7-methyl-4-oxo-6,7-dihydropyrazolo[1,5-a]pyrazine-3-carboxamide;

4-[[(7S)-7-methyl-4-oxo-5-[4-(trifluoromethyl)phenyl]-6,7-dihydropyrazolo[1,5-a]pyrazine-3-carbonyl]amino]benzenesulfonyl fluoride;

and the pharmaceutically acceptable salts and solvates of such compounds.

Particular compounds according to the invention include:

(7S)—N-(5-fluoro-3-pyridyl)-7-methyl-4-oxo-5-[4-(trifluoromethyl)phenyl]-6,7-dihydropyrazolo[1,5-a]pyrazine-3-carboxamide hydrochloride salt;

(7S)—N-(3-fluoro-2-pyridyl)-7-methyl-4-oxo-5-[4-(trifluoromethyl)phenyl]-6,7-dihydropyrazolo[1,5-a]pyrazine-3-carboxamide hydrochloride salt;

(7S)-5-[3-chloro-4-(trifluoromethyl)phenyl]-7-methyl-N-(4-methyl-3-pyridyl)-4-oxo-6,7-dihydropyrazolo[1,5-a]pyrazine-3-carboxamide hydrochloride salt.

The present invention further relates to derivatives designed to bind irreversibly to the mGluR2 receptor, in particular to the allosteric pocket thereof.

In an embodiment, these compounds have the formula (I-a)

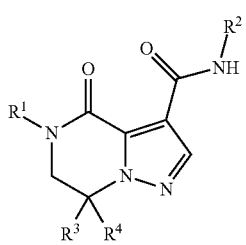

(I-a)

and stereoisomeric forms thereof, wherein $R^1$ is phenyl or 2-pyridinyl, each optionally substituted with one or more substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, $C_{3-7}$cycloalkyl, —O—$C_{1-4}$alkyl, monohalo-$C_{1-4}$alkyloxy, polyhalo-$C_{1-4}$alkyloxy, $SF_5$, $C_{1-4}$alkylthio, monohalo-$C_{1-4}$alkylthio and polyhalo-$C_{1-4}$alkylthio;

$R^2$ is phenyl substituted with —$S(O)_2F$;

$R^3$ is selected from hydrogen and $C_{1-4}$alkyl;

$R^4$ is selected from the group consisting of hydrogen, $C_{1-4}$alkyl, monohalo-$C_{1-4}$alkyl, polyhalo-$C_{1-4}$alkyl, —$C_{1-4}$alkyl-O—$C_{1-4}$alkyl and —$C_{1-4}$alkyl-OH;

and the N-oxides and the pharmaceutically acceptable salts and the solvates thereof.

The names of the compounds of the present invention were generated according to the nomenclature rules agreed upon by the International Union of Pure and Applied Chemistry (IUPAC) generated by Accelrys Direct, Revision 8.0 SP1 (Microsoft Windows 64-bit Oraclell) (8.0.100.4), Open-Eye:1.2.0. In case of tautomeric forms, the name of the depicted tautomeric form of the structure was generated. However it should be clear that the other non-depicted tautomeric form is also included within the scope of the present invention.

Definitions

The notation "$C_{1-4}$alkyl" as used herein alone or as part of another group, defines a saturated, straight or branched, hydrocarbon radical having, unless otherwise stated, from 1 to 4 carbon atoms, such as methyl, ethyl, 1-propyl, 1-methylethyl, butyl, 1-methyl-propyl, 2-methyl-1-propyl, 1,1-dimethylethyl and the like. The notation "—$C_{1-4}$alkyl-OH" as used herein alone or as part of another group, refers to $C_{1-4}$alkyl as defined before, substituted with one OH group at any available carbon atom.

The notation "halogen" or "halo" as used herein alone or as part of another group, refers to fluoro, chloro, bromo or iodo, with fluoro or chloro being preferred.

The notation "monohalo-$C_{1-4}$alkyl, polyhalo-$C_{1-4}$alkyl" as used herein alone or as part of another group, refers to $C_{1-4}$alkyl as defined before, substituted with 1, 2, 3 or where possible with more halo atoms as defined before The notation "$C_{3-7}$cycloalkyl" as used herein refers to a saturated, cyclic hydrocarbon radical having from 3 to 7 carbon atoms, such as cyclopropyl, cyclobutyl, cyclopentyl, cyclohexyl and cycloheptyl. A particular $C_{3-7}$cycloalkyl group is cyclopropyl.

The N-oxide forms of the compounds according to Formula (I) are meant to comprise those compounds of Formula (I) wherein one or several nitrogen atoms are oxidized to the so called N-oxide, particularly those N-oxides wherein a nitrogen atom in a pyridinyl radical is oxidized. N-oxides can be formed following procedures known to the skilled person. The N-oxidation reaction may generally be carried out by reacting the starting material of Formula (I) with an appropriate organic or inorganic peroxide. Appropriate inorganic peroxides comprise, for example, hydrogen peroxide, alkali metal or alkaline metal peroxides, e.g. sodium peroxide, potassium peroxide/appropriate organic peroxides may comprise peroxy acids such as, for example, benzenecarboperoxoic acid or halo substituted benzenecarboperoxoic acid, e.g. 3-chloroperoxybenzoic acid (or 3-chloroperbenzoic acid), peroxoalkanoic acids, e.g. peroxoacetic acid, alkylhydroperoxides, e.g. tert-butyl hydroperoxide. Suitable solvents, are for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Whenever the term "substituted" is used in the present invention, it is meant, unless otherwise is indicated or is clear from the context, to indicate that one or more hydrogens, preferably from 1 to 3 hydrogens, more preferably from 1 to 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

It will be appreciated that some of the compounds of Formula (I) and their pharmaceutically acceptable addition salts and solvates thereof may contain one or more centres of chirality and exist as stereoisomeric forms.

The term "compounds of the invention" as used herein, is meant to include the compounds of Formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic (partially) saturated radicals may have either the cis- or trans-configuration; for example if a compound contains a disubstituted cycloalkyl group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above formula are intended to be included within the scope of the present invention.

It follows that a single compound may exist in both stereisomeric and tautomeric forms.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form, for example $^2H$. Radiolabelled compounds of Formula (I) may comprise a radioactive isotope selected from the group consisting of $^3H$, $^{11}C$, $^{14}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group consisting of $^3H$, $^{11}C$ and $^{18}F$.

Preparation

The compounds according to the invention can generally be prepared by a succession of steps, each of which is known to the skilled person. In particular, the compounds can be prepared according to the following synthesis methods.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase or chiral supercritical fluid chromatography (SFC). Said pure stereochemically isomeric forms may also be derived from the corresponding pure stereochemically isomeric forms of the appropriate starting materials, provided that the reaction occurs stereospecifically. The absolute configuration of compounds of the invention reported herein was determined by analysis of the racemic mixture by supercritical fluid chromatography (SFC) followed by SFC comparison of the separate enantiomer(s) which were obtained by asymmetric synthesis, followed by vibrational circular dichroism (VCD) analysis of the particular enantiomer(s).

A. Preparation of the Final Compounds

Experimental Procedure 1

Final compounds according to Formula (I-a) can be prepared by a coupling reaction of a compound of Formula (II-a) with a compound of Formula (III), according to conditions known to the skilled person. Such conditions for example include a suitable coupling agent such as O-(benzotriazol-1-yl)-N,N,N',N'-tetramethyluronium hexafluorophosphate (HBTU), N-(3-dimethylaminopropyl)-N'-ethylcarbodiimide (EDCI) or 2-(7-aza-1H-benzotriazole-1-yl)-1,1,3,3-tetramethyluronium hexafluorophosphate (HATU) in presence of a suitable base such as N,N-diisopropylethylamine (DIPEA), triethylamine ($Et_3N$) or 4-(dimethylamino)pyridine (DMAP) in a suitable solvent such as N,N-dimethylformamide (DMF) or dichloromethane (DCM) under suitable reaction conditions, such as at a convenient temperature, typically room temperature (rt), for a period of time to ensure the completion of the reaction. A compound of Formula (III) can be obtained commercially or made according to procedures known in the art. In Reaction Scheme 1, all variables are defined as in Formula (I).

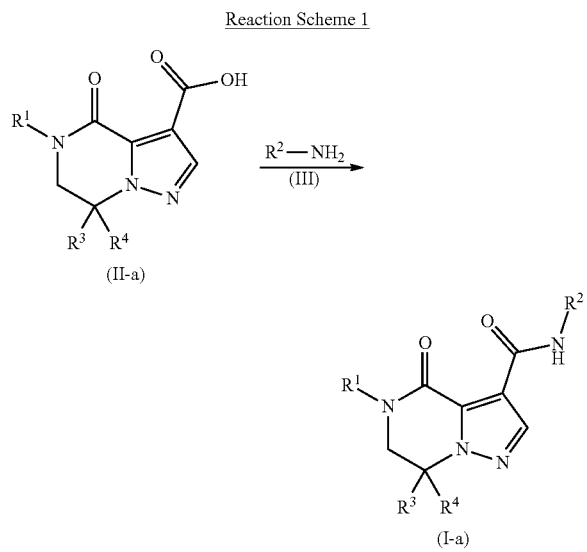

Experimental Procedure 2

Alternatively, final compounds according to Formula (I-a) can be prepared by a Goldberg coupling reaction of a compound of Formula (II-b) with an appropriate aryl/heteroaryl halide of Formula (IV) where X is a halo, according to conditions known to the skilled person. Such conditions for example include the use of a suitable palladium catalyst system such as tris(dibenzylideneacetone)dipalladium(0) ($Pd_2(dba)_3$), in the presence of a ligand such as 4,5-bis (diphenylphosphino)-9,9-dimethylxanthene (Xantphos), in the presence of a suitable base such as potassium phosphate ($K_3PO_4$) in a suitable solvent such as tetrahydrofuran (THF), under suitable reaction conditions, such as at a convenient temperature, typically ranging between 80° C. and 100° C., in particular 90° C., for a period of time to ensure the completion of the reaction. A compound of Formula (IV) can be obtained commercially or made according to procedures known in the art. In Reaction Scheme 2, all variables are defined as in Formula (I).

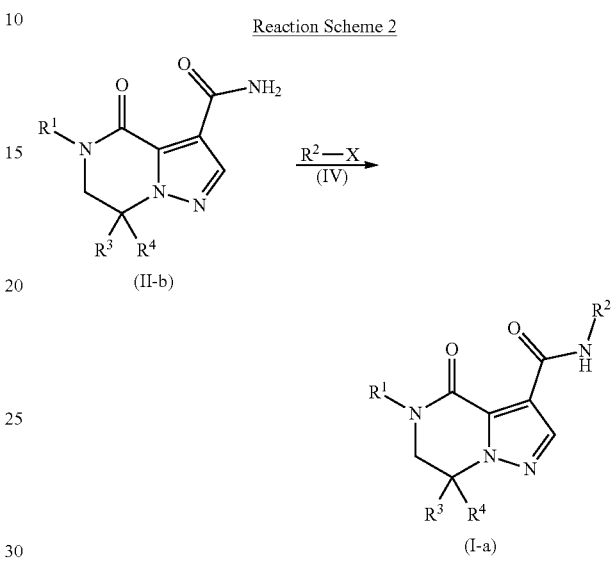

Alternatively, final compounds according to Formula (I-a) can be prepared by a Goldberg coupling reaction of a compound of Formula (II-b) with an appropriate aryl/heteroaryl halide of Formula (IV) where X is a halo, according to conditions known to the skilled person. Such conditions for example include the use of a suitable copper catalyst such as copper(I) iodide, in the presence of a ligand such as (+/−)-trans-1,2-cyclohexanediamine, in the presence of a suitable base such as potassium phosphate ($K_3PO_4$), with or without an organic base such as triethylamine (TEA), in a suitable solvent such as 1,4-dioxane, under suitable reaction conditions, such as at a convenient temperature, typically ranging between 80° C. and 120° C., in particular 100° C., for a period of time to ensure the completion of the reaction. A compound of Formula (IV) can be obtained commercially or made according to procedures known in the art. In Reaction Scheme 2, all variables are defined as in Formula (I).

Experimental Procedure 3

Alternatively, final compounds according to Formula (I-a) can be prepared by a reaction between an activated ester of Formula (II-c) with a compound of Formula (III) according to conditions known to the skilled person. Such conditions for example include the use of a suitable base such as $Et_3N$ and a suitable activating agent such as DMAP in a suitable solvent such as THF under suitable reaction conditions such as at a convenient temperature, typically ranging between 60° C. and 80° C., in particular 70° C., for a period of time to ensure the completion of the reaction. A compound of Formula (III) can be obtained commercially or made according to procedures known in the art. In Reaction Scheme 3, all variables are defined as in Formula (I).

Reaction Scheme 3

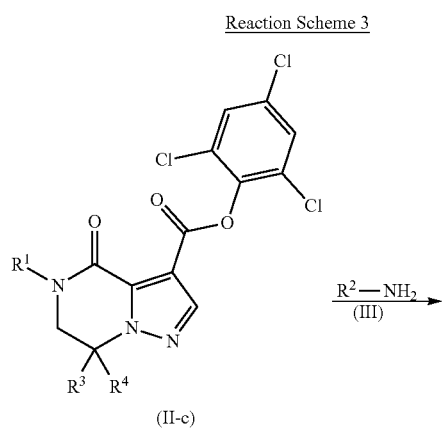

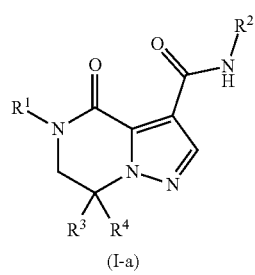

Experimental Procedure 4

Alternatively, final compounds according to Formula (I-a) can be prepared by a one pot reaction of carbonylation of a compound of Formula (V) combined with a peptide type coupling reaction with an appropriate compound of Formula (III), according to conditions known to the skilled person. Such conditions for example include the use of carbon monoxide and a suitable palladium catalyst system such as palladium(II) acetate, in the presence of a ligand such as 1,1'-bis(diphenylphosphino) ferrocene (dppf), in the presence of a suitable base such as Et₃N in a suitable solvent such as 1,4-dioxane, under suitable reaction conditions, such as at a convenient temperature, typically ranging between 80° C. and 100° C., in particular 90° C., for a period of time to ensure the completion of the reaction. A compound of Formula (III) can be obtained commercially or made according to procedures known in the art. In Reaction Scheme 4, all variables are defined as in Formula (I).

Reaction Scheme 4

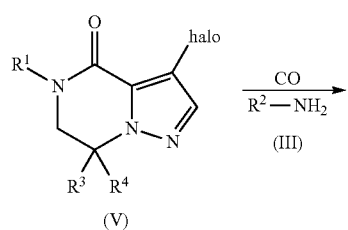

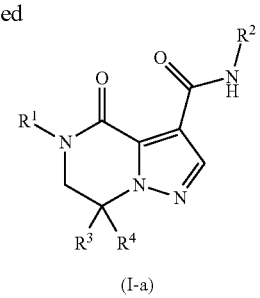

Experimental Procedure 5

Alternatively, final compounds according to Formula (I-a) can be prepared by a reaction between an ester of Formula (II-d) wherein $R^y$ is $C_{1-4}$alkyl with a compound of Formula (III) according to conditions known to the skilled person. Such conditions for example include the use of a suitable Lewis Acid such as trimethylaluminium (AlMe₃) or a Grignard reagent, such as for example isopropylmagnesium chloride lithium chloride complex solution or ethylmagnesium bromide or a suitable base such as lithium bis(trimethylsilyl)amide, in a suitable solvent such as THF under suitable reaction conditions such as such as at a convenient temperature, typically ranging between 0° C. and 30° C., for a period of time to ensure the completion of the reaction. A compound of Formula (III) can be obtained commercially or made according to procedures known in the art. In Reaction Scheme 5, all variables are defined as in Formula (I).

Reaction Scheme 5

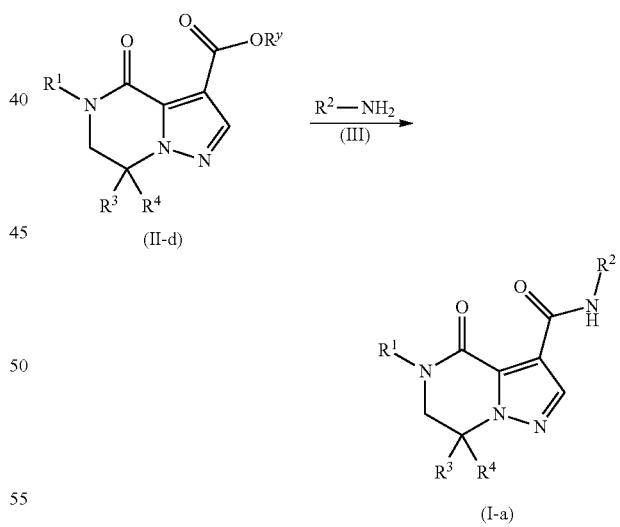

Experimental Procedure 6

Alternatively, final compounds according to Formula (I), wherein $R^2$ is —C(O)R⁵ or Het² and wherein R⁵ is as defined hereinbefore except hydrogen (hereby referred to as substituent $R^{2a}$), hereby referred to as compounds of Formula (I-b1) can be prepared by a one-step oxidation of a compound of Formula (II-e) according to conditions known to the skilled person. Such conditions for example include the use of a suitable oxidating reagent such as for example Dess-Martin Periodinane®, in a suitable mixture of solvent such as fluorobenzene and dimethylsulfoxide (DMSO) and under suitable reaction conditions such as such as at a convenient temperature, typically ranging between 80° C. and 100° C., in particular 85° C., for a period of time to ensure the completion of the reaction. In Reaction Scheme 6, all variables are defined as in Formula (I).

Reaction Scheme 6

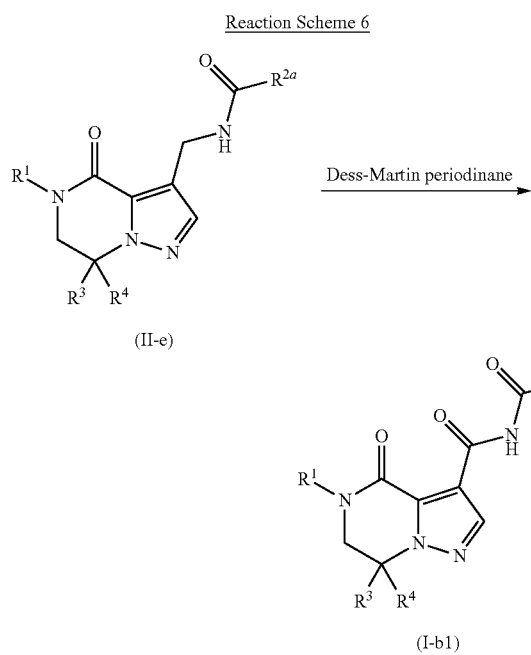

Experimental Procedure 7

Alternatively, final compounds according to Formula (I-b1) (as defined in experimental procedure 6) can be prepared by acylation of a compound of Formula (II-b) with an appropriate acid chloride of Formula (VI) according to conditions known to the skilled person. Such conditions for example include the use of a suitable base such as for example pyridine, under suitable reaction conditions such as at a convenient temperature, typically ranging between 40° C. and 60° C., in particular 50° C., for a period of time to ensure the completion of the reaction. A compound of Formula (VI) can be obtained commercially or made according to procedures known in the art. In Reaction Scheme 7, all variables are defined as in Formula (I).

Reaction Scheme 7

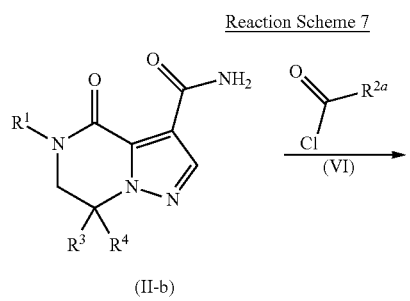

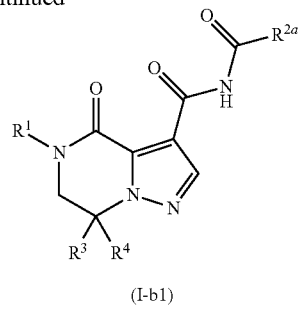

Experimental Procedure 8

Alternatively, final compounds according to Formula (I) wherein $R^2$ is —C(O)$R^5$ and wherein $R^5$ is hydrogen hereby referred to as compounds of Formula (I-b2) can be prepared by formylation of a compound of Formula (II-b) with N,N-dimethylformamide dimethyl acetal (DMFDMA) according to conditions known to the skilled person. In Reaction Scheme 8, all variables are defined as in Formula (I).

Reaction Scheme 8

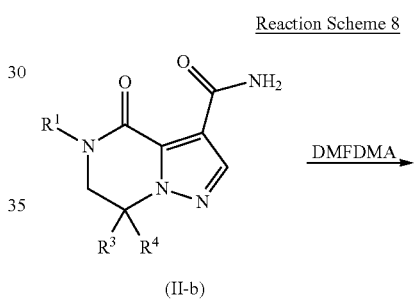

Experimental Procedure 9

Alternatively, final compounds according to Formula (I-a) can be prepared by a reaction of deprotection of a compound of Formula (I-a1) according to conditions known to the skilled person. A compound of Formula (I-a1) can be obtained by removal of the protecting group such as for example a dimethylpyrrole protecting group in the compound of Formula (I-a1), in the presence of basic media, such as hydroxylamine hydrochloride and $Et_3N$ in an inert solvent such as a mixture of ethanol/water, under suitable reaction conditions, such as at a convenient temperature, typically ranging between 80° C. and 120° C., in particular 100° C., for a period of time to ensure the completion of the reaction. In Reaction Scheme 9, all variables are defined as Reaction Scheme 9

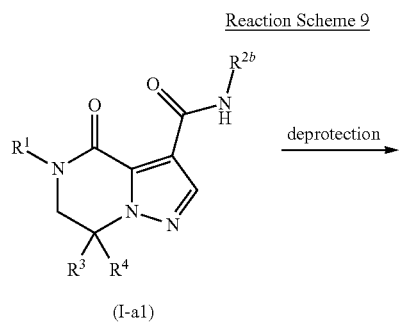

(I-a1)

↓ deprotection

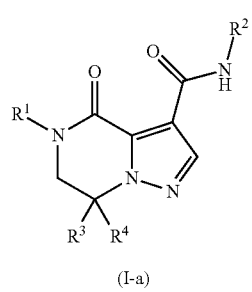

(I-a)

B. Preparation of the Intermediate Compounds

Experimental Procedure 10

Intermediate compounds according to Formula (II-a) can be prepared following art known procedures such as for example a transition metal catalyzed carbon monoxide insertion reaction of an intermediate compound of Formula (V) according to conditions known to the skilled person. Such conditions for example include the use of carbon monoxide and a suitable palladium catalyst system such as palladium (II) acetate, in the presence of a ligand such as dppf, in the presence of a suitable base such as Et₃N in a suitable solvent such as 1,4-dioxane and water, under suitable reaction conditions, such as at a convenient temperature, typically ranging between 70° C. and 90° C., in particular 80° C., for a period of time to ensure the completion of the reaction. Alternatively, an ester of Formula (II-d) can be saponified to give intermediate compound of Formula (II-a). The reaction can be performed for example by adding a hydroxide, such as sodium hydroxide (NaOH), to a solution of ester of Formula (II-d) in a suitable polar solvent such as methanol (MeOH). Heating the reaction mixture can enhance the reaction outcome. Alternatively a nitrile of Formula (II-f) can be hydrolyzed to give an intermediate compound of Formula (II-a). The reaction can be performed for example by heating a solution of nitrile of Formula (II-f) in a suitable solvent such as an aqueous solution of hydrochloric acid. Heating the reaction mixture can enhance the reaction outcome.

Intermediate compounds according to Formula (II-d) wherein $R^y$ is $C_{1-4}$alkyl can be prepared following art known procedures such as for example a transition metal catalyzed carbon monoxide insertion reaction of an intermediate compound of Formula (V) according to conditions known to the skilled person. Such conditions for example include the use of carbon monoxide and a suitable palladium catalyst system such as palladium(II) acetate, in the presence of a ligand such as dppf, in the presence of a suitable base such as Et₃N in a suitable solvent such as 1,4-dioxane and ethanol (EtOH), under suitable reaction conditions, such as at a convenient temperature, typically ranging between 80° C. and 100° C., in particular 95° C., for a period of time to ensure the completion of the reaction.

Intermediate compounds according to Formula (II-f) can be prepared following art known procedures such as for example a palladium catalyzed reaction with zinc cyanide of an intermediate of Formula (V). Such conditions for example include a Negishi type reaction of an intermediate compound of Formula (V) with a suitable palladium catalyst system such as 1,1'-bis(diphenylphosphino)ferrocene dichloropalladium(II), in a suitable solvent such as DMF, under suitable reaction conditions, such as at a convenient temperature, typically ranging between 130° C. and 170° C., in particular 150° C., for a period of time to ensure the completion of the reaction. Stirring and microwave irradiation may enhance the rate of the reaction.

In Reaction Scheme 10, halo is defined as Cl, Br or I, $R^y$ is $C_{1-4}$alkyl and all other variables are defined as in Formula (I).

Reaction Scheme 10

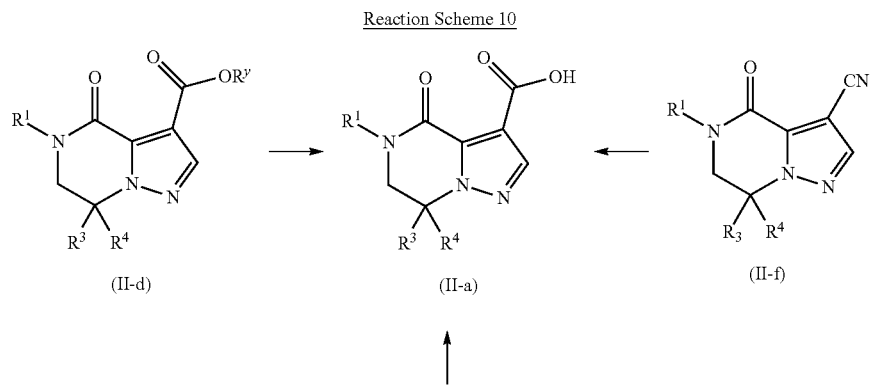

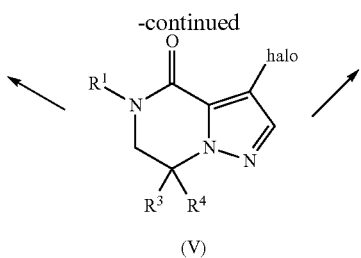

(V)

Experimental Procedure 11

Intermediate compounds according to Formula (II-b) can be prepared following art known procedures such as for example by an acidic hydrolysis of an intermediate compound of Formula (II-f). The reaction can be performed for example by heating a solution of nitrile of Formula (II-f) in a suitable solvent such as a solution of concentrated sulfuric acid. Alternatively an intermediate of Formula (II-b) can be prepared by a coupling reaction of a compound of Formula (II-a) with ammonium chloride (NH$_4$Cl), according to conditions known to the skilled person. Such conditions for example include a suitable coupling agent such as HBTU, in presence of a suitable base such as DIPEA, in a suitable solvent such as DMF, under suitable reaction conditions, such as at a convenient temperature, typically room temperature (rt), for a period of time to ensure the completion of the reaction. In Reaction Scheme 11, all variables are defined as in Formula (I).

Reaction Scheme 11

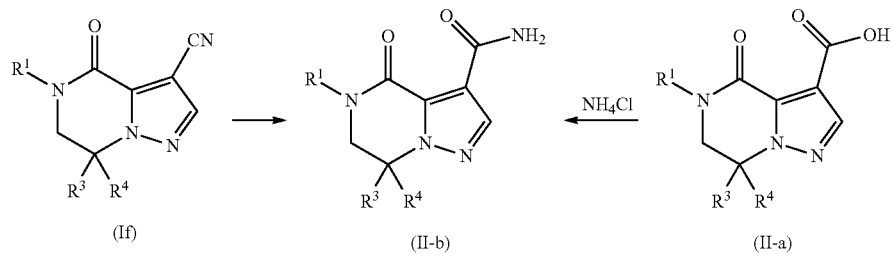

(If)     (II-b)     (II-a)

Experimental Procedure 12

Intermediate compounds according to Formula (II-c) can be prepared following art known procedures such as for example by a palladium catalyzed carbonylation reaction of an intermediate compound of Formula (V) using a carbon monoxide surrogate such as a phenylformate type derivative. Such conditions for example include the use of for example (2,4,6-trichlorophenyl)formate and a suitable palladium catalyst system such as palladium(II) acetate, in the presence of a ligand such as 4,5-bis(diphenylphosphino)-9,9-dimethylxanthene (Xantphos), in the presence of a suitable base such as Et$_3$N in a suitable solvent such as toluene, under suitable reaction conditions, such as at a convenient temperature, typically ranging between 60° C. and 80° C., in particular 70° C., for a period of time to ensure the completion of the reaction. Phenylformate type derivative can be synthesized according to literature procedures. In Reaction Scheme 12, halo is defined as Br or I and all other variables are defined as in Formula (I).

Reaction Scheme 12

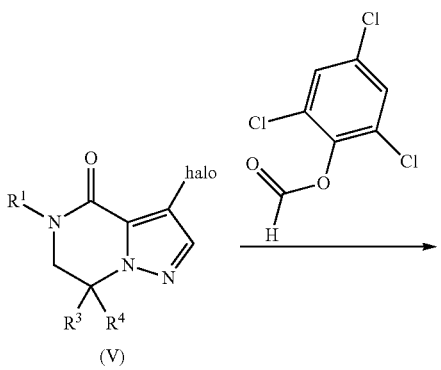

-continued

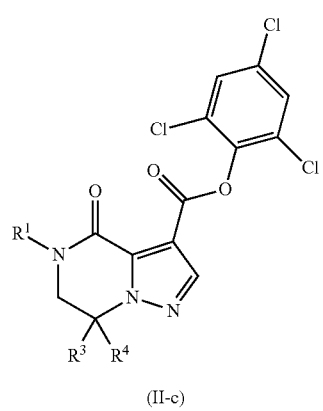

(II-c)

Experimental Procedure 13

Intermediate compounds according to Formula (V) can be prepared by a Goldberg coupling reaction of a compound of Formula (VII-a) with an appropriate aryl/heteroaryl halide of Formula (VIII) where X is halo, in particular bromo or iodo, according to conditions known to the skilled person. Such conditions include for example using a suitable copper (I) catalyst such as copper(I) iodide, in the presence of a ligand, such as N,N-dimethylethylenediamine, in the presence of a base, such as inorganic carbonates, for example sodium carbonate ($Na_2CO_3$) or potassium carbonate ($K_2CO_3$), in a suitable solvent, such as toluene or a mixture of toluene and DMF, under suitable reaction conditions, such as at a convenient temperature, typically ranging between 100° C. and 140° C., in particular 110° C., for a period of time to ensure the completion of the reaction. A compound of Formula (VIII) can be obtained commercially or made according to procedures known in the art.

Alternatively intermediate compound according to Formula (V) can be prepared via a reaction of halogenation of an intermediate of Formula (VII-b) with a halogenating reagent such as iodine, in the presence of ammonium cerium(IV) nitrate and in an inert solvent such as acetonitrile, under suitable reaction conditions, such as at a convenient temperature, typically 70° C., for a period of time to ensure the completion of the reaction.

In Reaction Scheme 13, halo is defined as Br or I and all other variables are defined as in Formula (I).

such as hydrochloric acid, in an inert solvent such as 1,4-dioxane or acetonitrile or ethyl acetate (EtOAc), under suitable reaction conditions, such as at a convenient temperature, such as from 15 to 80° C., typically 80° C. or from 15-30° C. depending on the solvent system, for a period of time to ensure the completion of the reaction followed by treatment with a base such as $Na_2CO_3$, $K_2CO_3$ or $NaHCO_3$, under suitable reaction conditions, such as at a convenient temperature, typically ranging between 0° C. and 40° C., in particular from 15 to 30° C., for a period of time to ensure the completion of the reaction.

Intermediate compound according to Formula (X-a) wherein $R^x$ is $C_{1-4}$alkyl and PG is a protecting group, for example Boc, can be prepared by a Mitsunobu type reaction between an intermediate compound of Formula (XI-a) and an appropriate alcohol of Formula (XII), in the presence of a suitable triarylphosphine, such as triphenylphosphine or a suitable trialkylphosphine, and a suitable dialkyl azodicarboxylate reagent, such as di-tert-butyl azodicarboxylate or diethyl azodicarboxylate, in a suitable inert solvent, such as THF, under suitable reaction conditions, such as at a convenient temperature, typically ranging 0° C. and rt, e.g. 20° C., for a period of time to ensure the completion of the reaction. Intermediate compounds of Formula (XII) and of Formula (IX-a) can be obtained commercially or synthesized according to literature procedures.

In Reaction Scheme 14, $R^x$ is $C_{1-4}$alkyl, PG is a protecting group, for example Boc, and all other variables are defined as in Formula (I).

Reaction Scheme 13

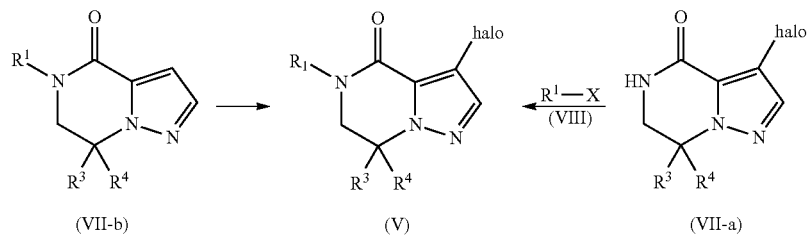

Experimental Procedure 14

Intermediate compounds according to Formula (VII-b) can be prepared by a Goldberg coupling reaction of a compound of Formula (IX-a) with an appropriate aryl/heteroaryl halide of Formula (VIII) where X is halo, in particular bromo or iodo, according to conditions known to the skilled person. Such conditions include for example using a suitable copper(I) catalyst such as copper(I) iodide, in the presence of a ligand, such as N,N-dimethylethylenediamine, in the presence of a base, such as inorganic carbonates, for example $Na_2CO_3$ or $K_2CO_3$, in a suitable solvent, such as toluene or a mixture of toluene and DMF, under suitable reaction conditions, such as at a convenient temperature, typically ranging between 100° C. and 140° C., in particular 110° C., for a period of time to ensure the completion of the reaction. A compound of Formula (VIII) can be obtained commercially or made according to procedures known in the art.

Intermediate compound according to Formula (IX-a) can be prepared by removal of the protecting group, for example a Boc group (tert-butoxycarbonyl), in an intermediate of Formula (X-a), for example in the presence of acidic media, Reaction Scheme 14

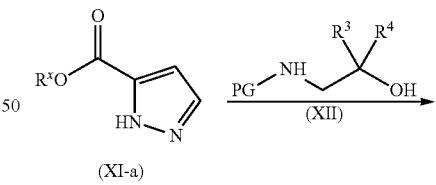

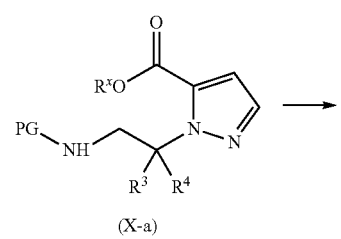

-continued

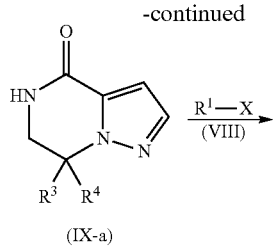 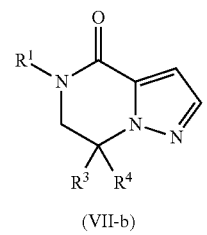

(IX-a) (VII-b)

Experimental Procedure 15

Intermediate compounds according to Formula (VII-a) wherein halo is bromo or iodo can be prepared by removal of the protecting group, for example a Boc group, in an intermediate of Formula (X-b), for example in the presence of acidic media, such as hydrochloric acid, in an inert solvent such as 1,4-dioxane or acetonitrile or ethyl acetate (EtOAc), under suitable reaction conditions, such as at a convenient temperature, such as from 15 to 80° C., typically 80° C. or from 15-30° C. depending on the solvent system, for a period of time to ensure the completion of the reaction followed by treatment with a base such as $Na_2CO_3$, $K_2CO_3$ or $NaHCO_3$, under suitable reaction conditions, such as at a convenient temperature, typically ranging between 0° C. and 40° C., in particular from 15 to 30° C., for a period of time to ensure the completion of the reaction.

Intermediate compound of Formula (X-b) wherein halo is defined as Br or I, $R^x$ is $C_{1-4}$alkyl and PG is a protecting group, for example Boc, can be prepared by a Mitsunobu type reaction between an intermediate compound of Formula (XI-b) and an appropriate alcohol of Formula (XII), in the presence of a suitable triarylphosphine, such as triphenylphosphine, or a suitable trialkylphosphine, and a suitable dialkyl azodicarboxylate reagent, such as di-tert-butyl azodicarboxylate or diethyl azodicarboxylate, in a suitable inert solvent, such as THF, under suitable reaction conditions, such as at a convenient temperature, typically ranging 0° C. and rt, e.g. 20° C., for a period of time to ensure the completion of the reaction. An intermediate compound of Formula (XII) can be obtained commercially or synthesized according to literature procedures.

Intermediate compound of Formula (IX-b) wherein $R^x$ is $C_{1-4}$alkyl, can be prepared via a reaction of halogenation of intermediate of Formula (XI-a) with a halogenating reagent such as N-iodosuccinimide, in an inert solvent such as DCM, under suitable reaction conditions, such as at a convenient temperature, typically rt, for a period of time to ensure the completion of the reaction. Intermediate compound of Formula (IX-b), wherein $R^x$ is methyl and halo is bromo, can be obtained commercially and is a particularly preferred material for use in the synthesis, including large scale, of a variety of final compounds of Formula (I) according to the general procedures described herein. An intermediate compound of Formula (XI-a) can be obtained commercially or synthesized according to literature procedures.

In Reaction Scheme 15, halo is, in particular bromo or iodo, $R^x$ is $C_{1-4}$alkyl, PG is a protecting group, such as for example Boc, and all other variables are defined as in Formula (I).

Reaction Scheme 15

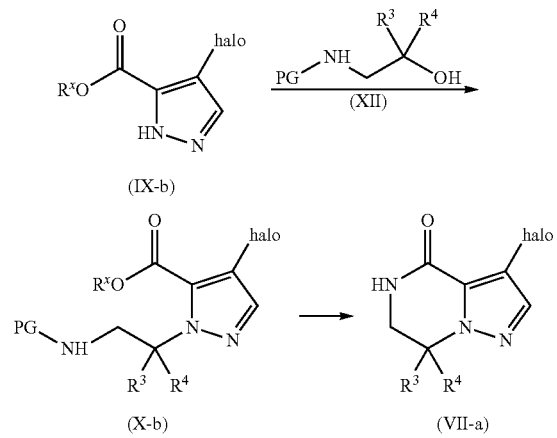

Experimental Procedure 16

Intermediate compounds according to Formula (II-d) can be prepared by a Goldberg coupling reaction of a compound of Formula (XIII) with an appropriate aryl/heteroaryl halide of Formula (VIII) where X is halo, in particular bromo or iodo, according to conditions known to the skilled person. Such conditions include for example using a suitable copper (I) catalyst such as copper(I) iodide, in the presence of a ligand, such as N,N-dimethylethylenediamine, in the presence of a base, such as inorganic carbonates, for example sodium carbonate ($Na_2CO_3$) or potassium carbonate ($K_2CO_3$), in a suitable solvent, such as toluene or a mixture of toluene and DMF, under suitable reaction conditions, such as at a convenient temperature, typically ranging between 100° C. and 140° C., in particular 110° C., for a period of time to ensure the completion of the reaction. A compound of Formula (VIII) can be obtained commercially or made according to procedures known in the art.

Intermediate compounds according to Formula (XIII) can be prepared following art known procedures such as for example a transition metal catalyzed carbon monoxide insertion reaction of an intermediate compound of Formula (VII-a) according to conditions known to the skilled person. Such conditions for example include the use of carbon monoxide and a suitable palladium catalyst system such as palladium(II) acetate, in the presence of a ligand such as dppf, in the presence of a suitable base such as $Et_3N$ in a suitable solvent such as a mixture of 1,4-dioxane and MeOH or EtOH, under suitable reaction conditions, such as at a convenient temperature, typically ranging between 70° C. and 90° C., in particular 80° C., for a period of time to ensure the completion of the reaction.

In Reaction Scheme 16, $R^y$ is $C_{1-4}$alkyl and all other variables are defined as in Formula (I).

Reaction Scheme 16

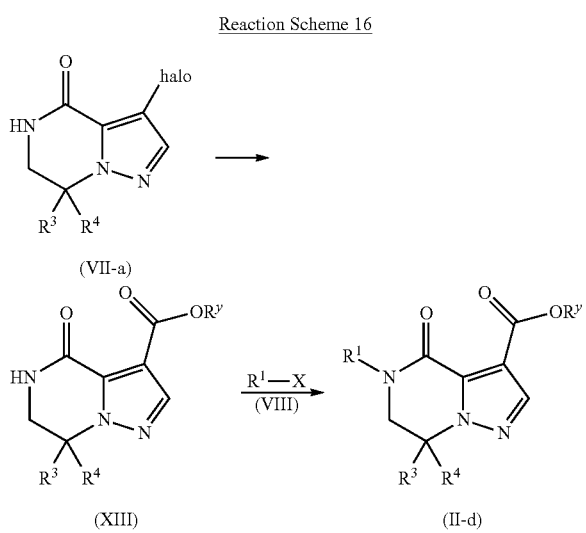

Experimental Procedure 17

Intermediate compounds according to Formula (II-d) wherein $R^y$ is $C_{1-4}$alkyl can be prepared by a reaction of compound of Formula (II-b) with N,N-dimethylformamide dimethyl acetal (DMFDMA) according to conditions known to the skilled person. In Reaction Scheme 17, all variables are defined as in Formula (I).

Reaction Scheme 17

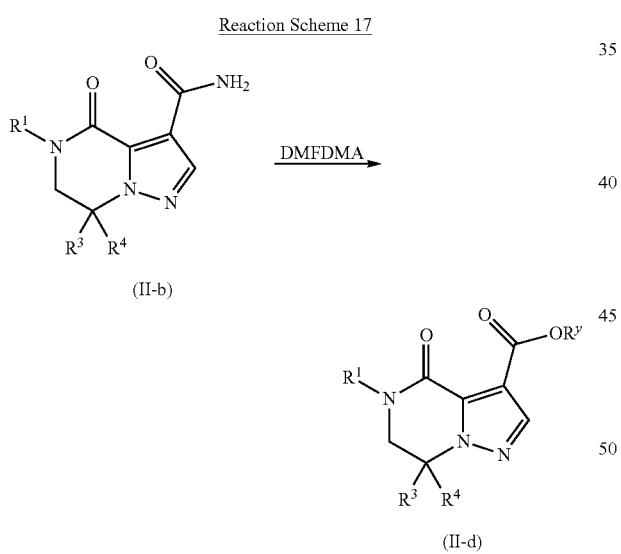

Experimental Procedure 18

Intermediate compounds according to Formula (II-e) wherein $R^{2a}$ is selected from the group consisting of $R^5$ (except hydrogen) and $Het^2$ can be prepared by acylation of a compound of Formula (XIV) with an appropriate acid chloride of Formula (VI) according to conditions known to the skilled person. Such conditions for example include the use of a suitable base such as, for example $Et_3N$, a suitable solvent such as for example DCM. Cooling the reaction mixture can enhance the reaction outcome.

Intermediate compounds according to Formula (XIV) can be prepared following art known procedures such as for example a reduction of an intermediate of Formula (II-f), for example by means of catalytic hydrogenation using a suitable metal such as for example Raney nickel and a suitable solvent such as 7 M ammonia solution in MeOH.

A compound of Formula (VI) can be obtained commercially or made according to procedures known in the art. In Reaction Scheme 18, $R^{2a}$ is selected from the group consisting of $R^5$ (except hydrogen) and $Het^2$ and all other variables are defined as in Formula (I).

Reaction Scheme 18

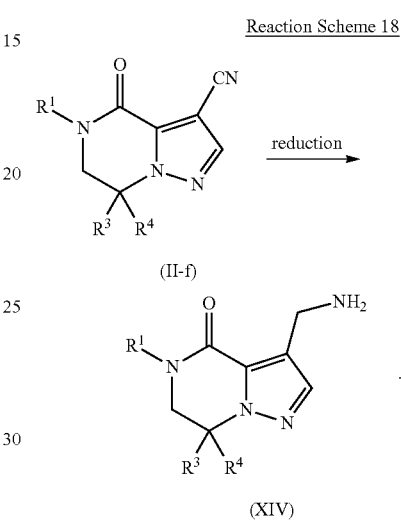

In order to obtain the HCl salt forms of the compounds, several procedures known to those skilled in the art can be used. In a typical procedure, for example, the free base can be dissolved in DIPE or $Et_2O$ and subsequently, a 6N HCl solution in 2-propanol or a 1N HCl solution in $Et_2O$ can be added dropwise. The mixture typically is stirred for 10 minutes after which the product can be filtered off. The HCl salt usually is dried in vacuo.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

The compounds provided in this invention are negative allosteric modulators (NAMs) of metabotropic glutamate receptors, in particular they are negative allosteric modulators of mGluR2. The compounds of the present invention do not appear to bind to the glutamate recognition site, the orthosteric ligand site, but instead to an allosteric site within the seven transmembrane region of the receptor. In the presence of glutamate, the compounds of this invention decrease the mGluR2 response. The compounds provided in this invention are expected to have their effect at mGluR2 by virtue of their ability to decrease the response of such receptors to glutamate, attenuating the response of the receptor.

As used herein, the term "treatment" is intended to refer to all processes, wherein there may be a slowing, interrupting, arresting or stopping of the progression of a disease or an alleviation of symptoms, but does not necessarily indicate a total elimination of all symptoms.

Hence, the present invention relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof for use as a medicament.

The invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for use in the treatment or prevention of, in particular treatment of, a condition in a mammal, including a human, the treatment or prevention of which is affected or facilitated by the neuromodulatory effect of allosteric modulators of mGluR2, in particular negative allosteric modulators thereof.

The present invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament for the treatment or prevention of, in particular treatment of, a condition in a mammal, including a human, the treatment or prevention of which is affected or facilitated by the neuromodulatory effect of allosteric modulators of mGluR2, in particular negative allosteric modulators thereof.

The present invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for use in the treatment, prevention, amelioration, control or reduction of the risk of various neurological and psychiatric disorders associated with glutamate dysfunction in a mammal, including a human, the treatment or prevention of which is affected or facilitated by the neuromodulatory effect of negative allosteric modulators of mGluR2.

Also, the present invention relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of negative allosteric modulators of mGluR2.

In particular, the neurological and psychiatric disorders associated with glutamate dysfunction, include one or more of the following central nervous system conditions or diseases: mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

In particular, the central nervous system disorder is a psychotic disorder selected from the group of schizophrenia (in particular in antipsychotic-stabilized patients), schizophreniform disorder, schizoaffective disorder, delusional disorder, brief psychotic disorder, and substance-induced psychotic disorder.

In particular, the central nervous system disorder is a substance-related disorder selected from the group of alcohol dependence, alcohol abuse, amphetamine dependence, amphetamine abuse, caffeine dependence, caffeine abuse, *cannabis* dependence, *cannabis* abuse, cocaine dependence, cocaine abuse, hallucinogen dependence, hallucinogen abuse, nicotine dependence, nicotine abuse, opioid dependence, opioid abuse, phencyclidine dependence, and phencyclidine abuse.

In particular, the central nervous system disorder is a mood disorder selected from the group of major depressive disorder, depression, treatment resistant depression, dysthymic disorder, cyclothymic disorder, and substance-induced mood disorder.

In particular, the central nervous system disorder is a disorder usually first diagnosed in infancy, childhood, or adolescence selected from mental retardation, learning disorder, motor skills disorder, communication disorder, attention-deficit and disruptive behaviour disorders (such as Attention-Deficit/Hyperactivity Disorder (ADHD)). An additional disorder usually first diagnosed in infancy, childhood, or adolescence is autistic disorder.

In particular, the central nervous system disorder is a cognitive disorder selected from the group of dementia, in particular, dementia of the Alzheimer's type, vascular dementia, dementia due to HIV disease, dementia due to head trauma, dementia due to Parkinson's disease, dementia due to Huntington's disease, dementia due to Pick's disease, dementia due to Creutzfeldt-Jakob disease, and substance-induced persisting dementia.

In particular, the central nervous system disorder is an amnestic disorder, such as substance-induced persisting amnestic disorder.

As already mentioned hereinabove, the term "treatment" does not necessarily indicate a total elimination of all symptoms, but may also refer to symptomatic treatment in any of the disorders mentioned above. In particular, symptoms that may be treated include but are not limited to, memory impairment in particular in dementia or in major depressive disorder, age-related cognitive decline, mild cognitive impairment, and depressive symptoms.

Of the disorders mentioned above, the treatment of dementia, major depressive disorder, depression, treatment resistant depression, attention-deficit/hyperactivity disorder and schizophrenia, in particular in antipsychotic-stabilized patients, are of particular importance.

The fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

A skilled person will be familiar with alternative nomenclatures, nosologies, and classification systems for the diseases or conditions referred to herein. For example, the "American Psychiatric Association: Diagnostic and Statistical Manual of Mental Disorders, Fifth Edition. Arlington, Va., American Psychiatric Association, 2013" (DSM-5™) utilizes terms such as depressive disorders, in particular, major depressive disorder, persistent depressive disorder (dysthymia), substance-medication-induced depressive disorder; neurocognitive disorders (NCDs) (both major and mild), in particular, neurocognitive disorders due to Alzheimer's disease, vascular NCD (such as vascular NCD present with multiple infarctions), NCD due to HIV infection, NCD due to traumatic brain injury (TBI), NCD due to Parkinson's disease, NCD due to Huntington's disease, frontotemporal NCD, NCD due to prion disease, and substance/medication-induced NCD; neurodevelopmental disorders, in particular, intellectual disability, specific learning disorder, neurodevelopmental motor disorder, communication disorder, and attention-deficit/hyperactivity disorder (ADHD); substance-related disorders and addictive disorders, in particular, alcohol use disorder, amphetamine use disorder, *cannabis* use disorder, cocaine use disorder, other hallucinogen use disorder, tobacco use disorder, opiod use disorder, and phencyclidine use disorder; schizophrenia spectrum and other psychotic disorders, in particular, schizophrenia, schizophreniform disorder, schizoaffective disorder, delusional disorder, brief psychotic disorder, substance/medication-induced psychotic disorder; somatic symptom disorders; hypersomnolence disorder; and cyclothymic disorder (which under DSM-5™ falls under the bipolar and related disorders category). Such terms may be used by the skilled person as an alternative nomenclature for some of the diseases or conditions referred to herein. An additional neurodevelopmental disorder includes autism spectrum disorder (ASD), which encompasses according to the DSM-5™, disorders previously known by the terms early infantile autism, childhood autism, Kanner's autism, high-functioning autism, atypical autism, pervasive developmental disorder not otherwise specified, childhood disintegrative disorder, and Asperger's disorder. In particular, the disorder is autism. Specifiers associated with ASD include those where the individual has a genetic disorder, such as in Rett syndrome or Fragile X syndrome.

Therefore, the invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for use in the treatment of any one of the diseases mentioned hereinbefore.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for use in treating any one of the diseases mentioned hereinbefore.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for the treatment or prevention, in particular treatment, of any one of the diseases mentioned hereinbefore.

The invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound of Formula (I), a stereoisomeric form thereof, or an N-oxide thereof, or a pharmaceutically acceptable salt or solvate thereof, in particular, a compound of Formula (I) or a stereoisomeric form thereof, or a pharmaceutically acceptable salt or a solvate thereof, to warm-blooded animals, including humans.

Therefore, the invention also relates to a method for the prevention and/or treatment of any one of the diseases mentioned hereinbefore comprising administering a therapeutically effective amount of a compound according to the invention to a subject in need thereof.

One skilled in the art will recognize that a therapeutically effective amount of the NAMs of the present invention is the amount sufficient to modulate the activity of the mGluR2 and that this amount varies inter alia, depending on the type of disease, the concentration of the compound in the therapeutic formulation, and the condition of the patient. Generally, an amount of NAM to be administered as a therapeutic agent for treating diseases in which modulation of the mGluR2 is beneficial, such as the disorders described herein, will be determined on a case by case by an attending physician.

Generally, a suitable dose is one that results in a concentration of the NAM at the treatment site in the range of 0.5 nM to 200 µM, and more usually 5 nM to 50 µM. To obtain these treatment concentrations, a patient in need of treatment likely will be administered an effective therapeutic daily amount of about 0.01 mg/kg to about 50 mg/kg body weight, preferably from about 0.01 mg/kg to about 25 mg/kg body weight, more preferably from about 0.01 mg/kg to about 10 mg/kg body weight, more preferably from about 0.01 mg/kg to about 2.5 mg/kg body weight, even more preferably from about 0.05 mg/kg to about 1 mg/kg body weight, more preferably from about 0.1 to about 0.5 mg/kg body weight. The amount of a compound according to the present invention, also referred to here as the active ingredient, which is required to achieve a therapeutically effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone. Examples of such combinations include the compounds of the invention in combination with antipsychotic(s), NMDA receptor antagonists (e.g. memantine), NR2B antagonists, acetylcholinesterase inhibitors (e.g. donepezil, galantamine, physostigmine and rivastigmine) and/or antidepressant neurotransmitter reuptake inhibitors. Particular combinations include the compounds of the invention in combination with antipsychotics, or the compounds of the invention in combination with memantine and/or NR2B antagonists.

Pharmaceutical Compositions

The present invention also provides compositions for preventing or treating diseases in which modulation of the mGluR2 receptor is beneficial, such as the disorders described herein. While it is possible for the active ingredient to be administered alone, it is preferable to present it as a pharmaceutical composition. Accordingly, the present invention also relates to a pharmaceutical composition comprising a pharmaceutically acceptable carrier or diluent and, as active ingredient, a therapeutically effective amount of a compound according to the invention, in particular a compound according to Formula (I), an N-oxide, a pharmaceutically acceptable salt thereof, a solvate thereof or a stereochemically isomeric form thereof, more in particular, a compound according to Formula (I), a pharmaceutically acceptable salt thereof, a solvate thereof or a stereochemically isomeric form thereof. The carrier or diluent must be "acceptable" in the sense of being compatible with the other ingredients of the composition and not deleterious to the recipients thereof.

The compounds according to the invention, in particular the compounds according to Formula (I), the N-oxides thereof, the pharmaceutically acceptable salts thereof, the solvates and the stereochemically isomeric forms thereof, more in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical, rectal or percutaneous administration, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, surfactants, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof.

Since the compounds according to the invention are orally administrable compounds, pharmaceutical compositions comprising aid compounds for oral administration are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs for use as a medicament or for use in the treatment, prevention, control, amelioration, or reduction of risk of diseases or conditions for which compounds of Formula (I) or the other drugs may have utility. The use of such a composition for the manufacture of a medicament as well as the use of such a composition for the manufacture of a medicament in the treatment, prevention, control, amelioration or reduction of risk of diseases or conditions for which compounds of Formula (I) or the other drugs may have utility are also contemplated. The present invention also relates to a combination of a compound according to the present invention and an additional drug selected from the group of antipsychotics; NMDA receptor antagonists (e.g. memantine); NR2B antagonists; acetylcholinesterase inhibitors (e.g. donepezil, galantamine, physostigmine and rivastigmine) and/or antidepressant neurotransmitter reuptake inhibitors. In particular, the present invention also relates to a combination of a compound according to the present invention and antipsychotic(s), or to a combination of a compound according to the present invention and memantine and/or an NR2B antagonist. The present invention also relates to such a combination for use as a medicine. The present invention also relates to a product comprising (a) a compound according to the present invention, an N-oxide thereof, a pharmaceutically acceptable salt thereof or a solvate thereof, in particular, a pharmaceutically acceptable salt thereof or a solvate thereof, and (b) an additional component selected from antipsychotics, NMDA receptor antagonists (e.g. memantine), NR2B antagonists, acetylcholinesterase inhibitors and/or antidepressant neurotransmitter reuptake inhibitor(s), as a combined preparation for simultaneous, separate or sequential use in the treatment or prevention of a condition in a mammal, including a human, the treatment or prevention of which is affected or facilitated by the neuromodulatory effect of mGluR2 allosteric modulators, in particular negative mGluR2 allosteric modulators. More in particular the additional component (b) is selected from antipsychotic(s) or memantine and/or an NR2B antagonist. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Chemistry

Several methods for preparing the compounds of this invention are illustrated in the following Examples. Unless otherwise noted, all starting materials were obtained from commercial suppliers and used without further purification.

Hereinafter, "BEH" means bridged ethylsiloxane/silica hybrid; "Boc" or "BOC" means tert-Butyloxycarbonyl; "CI" means chemical ionisation; "CSH" means charged surface hybrid; "DAD" means diode-array detector; "THF" means tetrahydrofuran; "Et$_3$N" means triethylamine; "DIPE" means diisopropylether; "DMAP" means 4-(dimethylamino)pyridine, "DMF" means N,N-dimethylformamide; "dppf" means 1,1'-bis(diphenylphosphino)ferrocene, "Et$_2$O" means diethylether; "EtOAc" means ethyl acetate; "EDCI.HCl" means N-(3-dimethylaminopropyl)-N-ethylcarbodiimide hydrochloride, "DCM" means dichloromethane; "DMSO" means dimethylsulfoxide; "DIPEA" means diisopropylethylamine, "L" means liter; "LRMS" means low-resolution mass spectrometry/spectra; "HATU" means 2-(7-aza-1H-benzotriazole-1-yl)-1,1,3,3-tetramethyluronium hexafluorophosphate; "HBTU" means O-(benzotriazol-1-yl)-N,N,N',N'-tetramethyluronium hexafluorophosphate, "HPLC" means high performance liquid chromatography; "HRMS" means high-resolution mass spectrometry/spectra; "mL" or "ml" means milliliter; "NH₄Ac" means ammonium acetate; "EtOH" means ethanol; "ES" means electrospray; "iPrOH" means isopropanol; "iPrNH₂" means isopropylamine; "MeOH" means methanol; "MSD" means Mass Selective Detector; "PyBOP®" means (benzotriazol-1-yloxy)tripyrrolidino-phosphonium hexafluorophosphate is a registered trademark of Merck KGaA, "Xantphos" means 4,5-bis(diphenylphosphino)-9,9-dimethylxanthene, "Pd₂(dba)₃" means tris(dibenzylideneacetone)dipalladium(0), "eq" means equivalent(s); "RP" means Reverse Phase; "rt" or "RT" mean room temperature; "M.p." means melting point; "min" means minutes; "h" means hour(s); "s" means second(s); "TOF" means time of flight; "QTOF" means Quadrupole-Time of Flight; "sat." means saturated; "SFC" means supercritical fluid chromatography; "sol." means solution; "SQD" means Single Quadrupole Detector; "UPLC" means Ultra Performance Liquid Chromatography.

Microwave assisted reactions were performed in a single-mode reactor: Initiator™ Sixty EXP microwave reactor (Biotage AB), or in a multimode reactor: MicroSYNTH Labstation (Milestone, Inc.).

Thin layer chromatography (TLC) was carried out on silica gel 60 F254 plates (Merck) using reagent grade solvents. Open column chromatography was performed on silica gel, particle size 60 Å, mesh=230-400 (Merck) using standard techniques. Automated flash column chromatography was performed using ready-to-connect cartridges from different vendors, on irregular silica gel, (normal phase disposable flash columns) on different flash systems.

Nuclear Magnetic Resonance (NMR): For a number of compounds, ¹H NMR spectra were recorded either on a Bruker Avance III, on a Bruker DPX-400 or on a Bruker AV-500 spectrometer with standard pulse sequences, operating at 400 MHz and 500 MHz, respectively. Chemical shifts (δ) are reported in parts per million (ppm) downfield from tetramethylsilane (TMS), which was used as internal standard.

The stereochemical configuration for the compounds has been designated "R" or "S"; for some compounds, the stereochemical configuration has been designated as "*R" or "*S" when the absolute stereochemistry is undetermined although the compound itself has been isolated as a single stereoisomer and is enantiomerically pure.

Synthesis of Intermediate Compounds

Intermediate 1 (I-1)

Ethyl 1H-pyrazole-5-carboxylate (I-1)

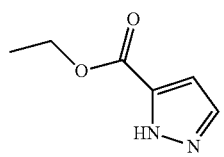

Sulfuric acid (10 mL, 187.6 mmol) was added to a solution of 1-H-pyrazole-3-carboxylic acid (1.93 g, 17.22 mmol) in EtOH (20 mL). The mixture was stirred at 90° C. for 15 h. Then it was allowed to cool to rt and the solvents were evaporated in vacuo. The residue was poured into water and the solution basified with K₂CO₃ and extracted with EtOAc. The organic layer was separated, dried (MgSO₄), filtered and the solvent evaporated in vacuo to yield intermediate compound I-1 as a white solid (2.28 g, 93% purity, 94%) which was used in the following step without further purification.

Intermediate 2 (I-2)

Ethyl 4-iodo-1H-pyrazole-5-carboxylate (I-2)

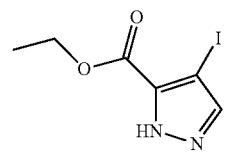

Intermediate I-1 (100 g, 0.68 mol), N-iodosuccinimide (213.5 g, 0.95 mol) were dissolved in DCM (2 L). The mixture was stirred at rt for 24 h. The mixture was treated with a sat. sol. of Na₂S₂O₃ and a sat. sol. of Na₂CO₃ and extracted with DCM. The organic layer was separated, dried (MgSO₄), filtered and the solvent evaporated in vacuo to yield intermediate compound I-2 as a white solid (160 g, 85%).

Intermediate 3 (I-3)

tert-Butyl N-[(2R)-2-hydroxypropyl]carbamate (I-3)

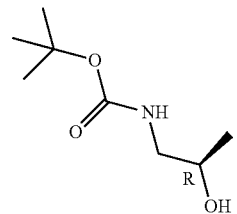

Di-tert-butyl dicarbonate (58.1 g, 266.3 mmol) in DCM (50 mL) was added to a stirred solution of (R)-(−)-1-amino-2-propanol in DCM (50 mL) at 0° C. under nitrogen. The mixture was stirred at rt for 2 h. The mixture was diluted with cooled water and extracted with DCM. The organic layer was separated, dried (Na₂SO₄), filtered and the solvents evaporated in vacuo to yield intermediate compound I-3 as a colorless oil (47 g, quant.). The product was used in the next step without further purification.

Intermediate 4 (I-4)

tert-Butyl N-(2-hydroxy-3-methoxy-propyl)carbamate (I-4)

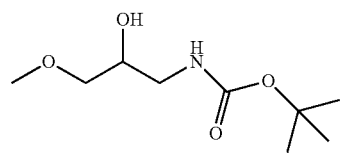

Intermediate I-4 was synthesized following a similar approach described for I-3. Starting from 1-amino-3-methoxy-2-propanol (2.3 g, 21.9 mmol), and introducing a purification step (flash column chromatography (silica; MeOH in DCM 0/100 to 5/95)), I-4 (3.1 g, 69%) was obtained.

Intermediate 5 (I-5)

Ethyl 2-[(1S)-2-(tert-butoxycarbonylamino)-1-methyl-ethyl]-4-iodo-pyrazole-3-carboxylate (I-5)

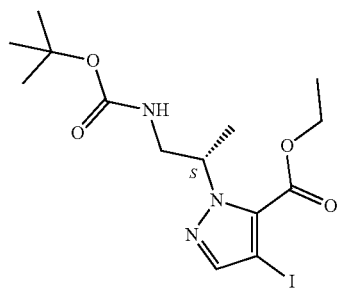

Di-tert-butyl azodicarboxylate (4.67 g, 20.3 mmol) was added to a stirred solution of intermediate I-2 (3 g, 11.28 mmol), intermediate I-3 (4.44 g, 22.55 mmol) and triphenylphosphine (5.32 g, 20.3 mmol) in THF (56 mL) under nitrogen. The mixture was stirred at rt for 5 h. The solvent was evaporated in vacuo and the crude product was triturated with DIPE. The solid was filtered and the filtrate was evaporated in vacuo. The crude product was purified by flash column chromatography (silica; EtOAc in Heptane 0/100 to 30/70). The desired fractions were collected and the solvents evaporated in vacuo to give intermediate compound I-5 as a colorless oil (4.9 g, 91% purity, 93%).

Intermediate 6 (I-6)

Ethyl 2-[(1S)-2-(tert-butoxycarbonylamino)-1-methyl-ethyl]pyrazole-3-carboxylate (I-6)

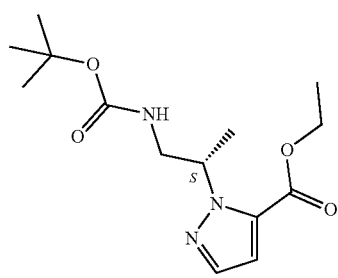

Intermediate compound I-6 was synthesized following a similar approach described for intermediate I-5. Starting from intermediate I-1 (25.82 g, 184.25 mmol) and intermediate I-3 (47.16 g, 239.5 mmol), intermediate compound I-6 was obtained as a yellow oil (123 g, quant) which was used in the following step without further purification.

Intermediate 7 (I-7)

Ethyl 2-[(1S)-2-amino-1-methyl-ethyl]-4-iodo-pyrazole-3-carboxylate. Hydrochloride Salt (I-7)

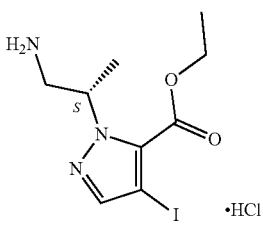

A 4M solution of HCl in 1,4-dioxane (10 mL, 40 mmol) was added to a solution of intermediate I-5 (4.2 g, 9.63 mmol) in acetonitrile (20 mL). The mixture was stirred at 80° C. for 2h. The solvent was evaporated in vacuo to yield intermediate compound I-7 (3.5 g, 97%).

Intermediate 8 (I-8)

Ethyl 2-[(1S)-2-amino-1-methyl-ethyl]pyrazole-3-carboxylate. Hydrochloride Salt (I-8)

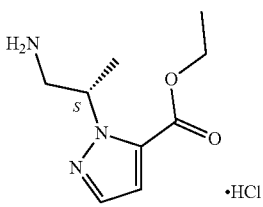

Intermediate compound I-8 was synthesized following a similar approach described for intermediate I-7. Starting from intermediate I-6 (54.79 g, 184.25 mmol) and a 4M solution of HCl in 1,4-dioxane (415 mL, 1.66 mol), intermediate compound I-8 was obtained as a white solid (32.5 g, 82% purity, 75%) which was used in the following step without further purification.

Intermediate 9 (I-9)

(7S)-3-Iodo-7-methyl-6,7-dihydro-5H-pyrazolo[1,5-a]pyrazin-4-one (I-9)

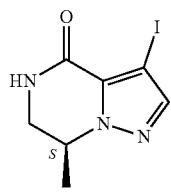

Intermediate I-7 as HCl salt (180 g, 350.4 mmol) was dissolved in a sat. sol. of NaHCO$_3$ (2 L). The mixture was stirred at rt for 12 h. The mixture was diluted with water and extracted with DCM. The organic layers were separated, dried (Na$_2$SO$_4$), filtered and the solvents evaporated in vacuo. Then the residue was washed with tert-butyl methyl ether to yield intermediate compound I-9 (92 g, 90%).

Intermediate 10 (I-10)

(7S)-7-Methyl-6,7-dihydro-5H-pyrazolo[1,5-a]pyrazin-4-one (I-10)

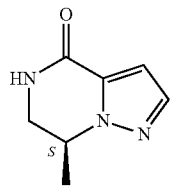

Intermediate compound I-10 was synthesized following a similar approach described for intermediate I-9. Starting from intermediate I-8 (32.5 g, 139.1 mmol), intermediate compound I-10 was obtained as a solid (14.8 g, 70%).

Intermediate 11 (I-11)

Ethyl 2-[1-[(tert-butoxycarbonylamino)methyl]-2-methoxy-ethyl]pyrazole-3-carboxylate (I-11)

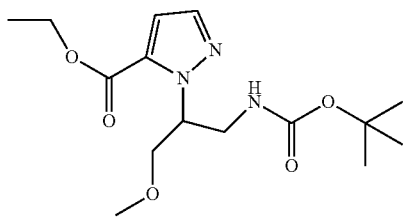 [SMILES: CCOC(=O)c1ccnn1C(CNC(=O)OC(C)(C)C)COC]

Di-tert-butyl azodicarboxylate (7.30 g, 31.68 mmol) was added to a stirred solution of I-1 (1.78 g, 12.671 mmol), intermediate I-4 (3.12 g, 15.21 mmol) and triphenylphosphine (8.31 g, 31.68 mmol) in THF (80 mL) under nitrogen at 0° C. The mixture was stirred at rt for 1 h. The solvent was evaporated and the residue was treated with DIPE, the solid was filtered and the filtrate was evaporated in vacuo. The crude product was purified by flash column chromatography (silica; EtOAc in heptane 0/100 to 50/50). The desired fractions were collected and the solvents evaporated in vacuo to give intermediate compound I-11 (4 g, 96%).

Intermediate 12 (I-12)

Ethyl 2-[1-(aminomethyl)-2-methoxy-ethyl]pyrazole-3-carboxylate (I-12)

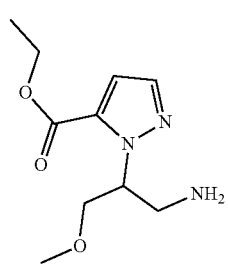 [SMILES: CCOC(=O)c1ccnn1C(CN)COC]

HCl (4 M in dioxane, 15.3 mL, 61.1 mmol) was added to a solution of I-11 (4 g, 12.22 mmol) in MeCN (55.3 mL). The mixture was stirred at rt for 1 h. The mixture was evaporated in vacuo to give intermediate compound I-12 (2.77 g) which was used without any further purification.

Intermediate 13 (I-13)

7-(Methoxymethyl)-6,7-dihydro-5H-pyrazolo[1,5-a]pyrazin-4-one (I-13)

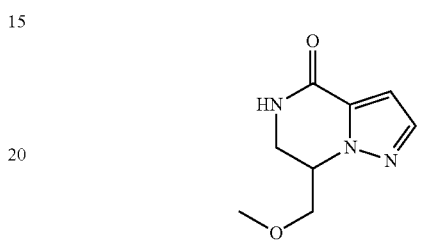

NaHCO₃ (sat. aqueous solution, 40 mL) was added to a solution of intermediate I-12 (2.77 g, 12.189 mmol) in MeOH (14.205 mL). The mixture was stirred at rt for 16 h. The mixture was diluted with water and extracted with DCM, EtOAc and THF/EtOAc 1:1. The organic layer was separated, dried (Na₂SO₄), filtered and the solvents evaporated in vacuo to give intermediate compound I-13 (1.92 g) which was used without any further purification.

Intermediate 14 (I-14)

4-Bromo-2-(methoxymethyl)-1-(trifluoromethyl)benzene (I-14)

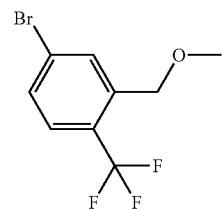

NaH (60% dispersion in mineral oils, 368 mg, 9.20 mmol) was added to a solution of 5-bromo-2-(trifluoromethyl)-benzenemethanol (1.96 g, 7.666 mmol) in THF (30.6 mL) at 0° C. and the mixture was stirred for 10 min at 0° C. Then methyl iodide (573 μL, 9.2 2799 mmol) was added and the mixture was stirred at rt for 1 h. Then, additional methyl iodide (95 μL, 1.5 mmol) was added and the mixture was stirred for 2 h. The mixture was quenched with water and extracted with EtOAc. The organic layer was separated, washed with sat. sol. NaCl, dried (Na₂SO₄), filtered and concentrated in vacuo to yield intermediate compound I-14 (2.06 g) which was used without any further purification.

Intermediate 15 (I-15)

(7S)-7-Methyl-5-[4-(trifluoromethyl)phenyl]-6,7-dihydropyrazolo[1,5-a]pyrazin-4-one (I-15)

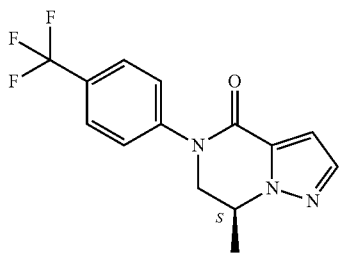

A mixture of intermediate I-14 (5 g, 33.01 mmol), copper (I) iodide (3.78 g, 19.85 mmol) and $K_2CO_3$ (9.14 g, 66.15 mmol) in toluene (150 mL) was nitrogen flushed for a few min. Then 4-bromobenzotrifluoride (9.3 mL, 66.1 mmol) and N,N-dimethylethylenediamine (2.1 mL, 19.8 mmol) were added. The mixture was stirred under nitrogen at rt for 10 min and then stirred at 100° C. for 16 h. Then, DMF (20 mL) was added and the mixture was stirred at 100° C. for 8 h. Then water, a conc. sol. of ammonia and DCM were added. The organic layer was separated, dried ($Na_2SO_4$), filtered and the solvents evaporated in vacuo. The crude product was purified by flash column chromatography (silica; EtOAc in DCM 0/100 to 50/50). The desired fractions were collected and the solvents evaporated in vacuo to yield intermediate compound I-15 as a pale yellow oil (9.6 g, 98%).

In a procedure analogous to that described for intermediate I-15, the following intermediates were synthesized:

-continued
| Starting Material | Reagent | Intermediate Product | |
|---|---|---|---|
| I-10 | 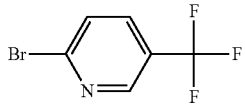 (solvent: toluene) | 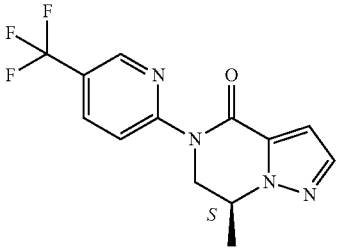 | I-20(*) |
| I-10 | 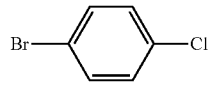 (solvent: toluene) | 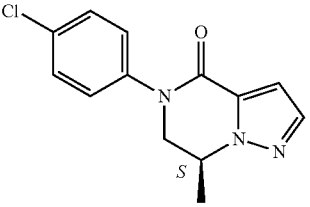 | I-21 |
| I-10 | 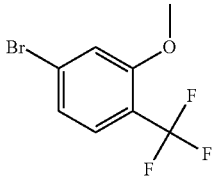 (solvent: toluene/DMF) | 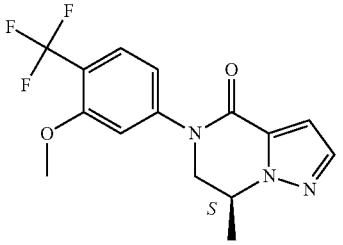 | I-22(**) |
| I-10 | 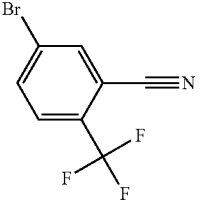 (solvent: toluene) | 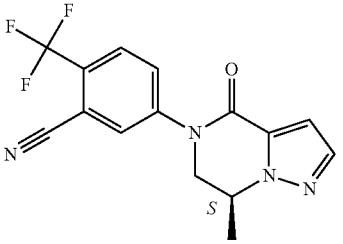 | I-23 |
| I-10 | 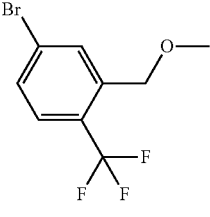 (solvent: toluene) | 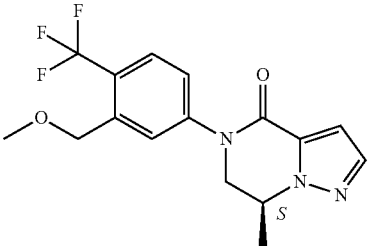 | I-24 |
| I-10 | 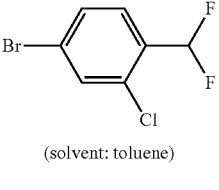 [SMILES: FC(F)c1ccc(Br)cc1Cl] (solvent: toluene) | 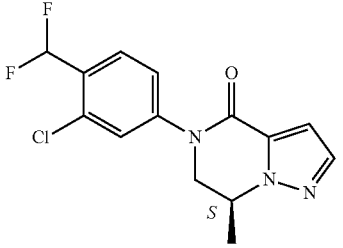 | I-25 |

-continued
| Starting Material | Reagent | Intermediate Product | |
|---|---|---|---|
| I-10 | 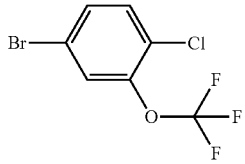 (solvent: toluene) | 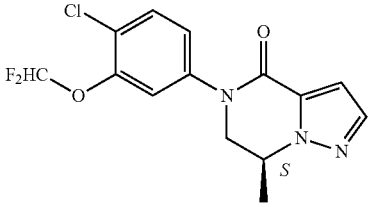 | I-26 |
| I-10 | 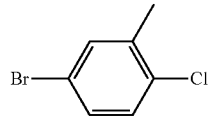 (solvent: toluene) | 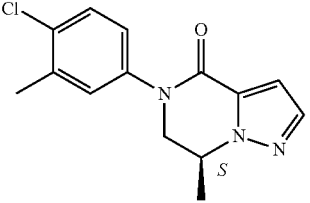 | I-27 |
| I-10 | 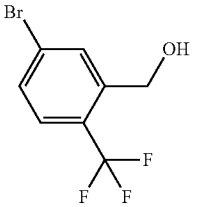 (solvent: toluene) | 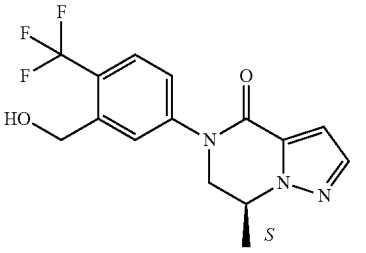 | I-28 |
| I-13 | 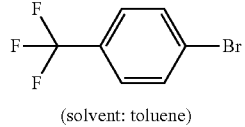 (solvent: toluene) | 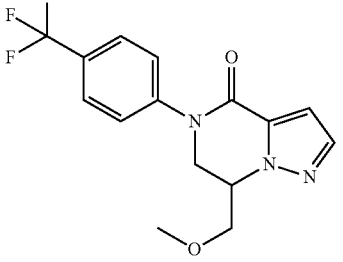 | I-29 |
| I-10 | 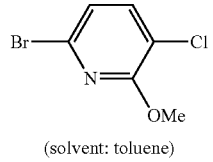 (solvent: toluene) | 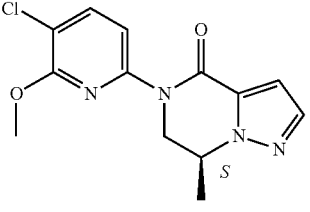 | I-30 |
| I-10 | 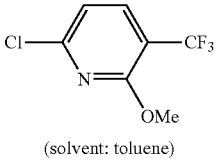 [SMILES: COc1nc(Cl)ccc1C(F)(F)F] (solvent: toluene) | 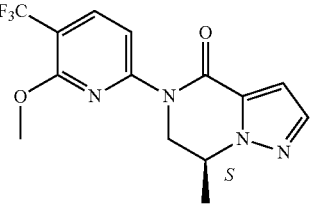 | I-31 |

| Starting Material | Reagent | Intermediate Product | |
|---|---|---|---|
| I-10 | 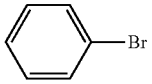<br>(solvent: toluene/DMF) | 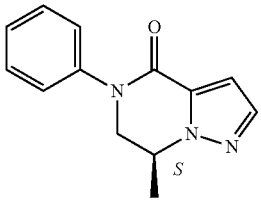 | I-32 |
| I-56 | 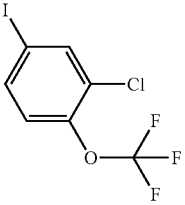 [SMILES: FC(F)(F)Oc1ccc(I)cc1Cl] | 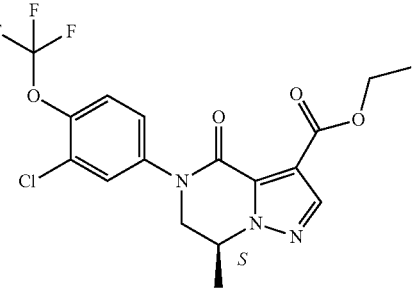 | I-94 |
| I-13 | 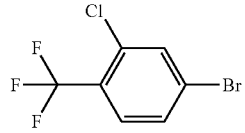<br>(solvent: toluene) | 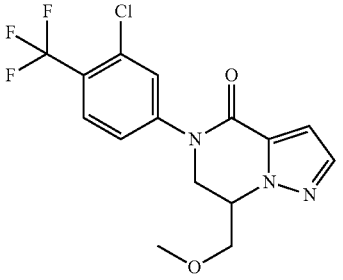 [SMILES: COCC1CN(c2ccc(C(F)(F)F)c(Cl)c2)C(=O)c2ccnn21] | I-98 |

(*)Intermediate I-20 was also made according to the procedure described below for I-34 using 2-chloro-5-(trifluoromethyl)pyridine as the reagent.
(**)Intermediate I-22 was also made according to the procedure described below for I-34.

Intermediate 33 (I-33)

6-Chloro-2-methoxy-pyridin-3-amine (I-33)

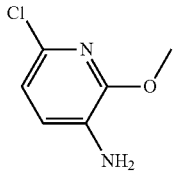

Sodium methoxide (25 wt. % in MeOH, 3.7 mL, 64.8 mmol) was added to a stirred solution of 3-amino-2,6-dichloropyridine (3 g, 18.4 mmol) in 1,4-dioxane (30 mL). The mixture was stirred at 140° C. for 20 min under microwave irradiation. The mixture was treated with a sat. sol. NH$_4$Cl and water and was stirred for 30 min. Then the mixture was extracted with Et$_2$O, washed with brine, dried (Na$_2$SO$_4$), filtered and the solvents concentrated in vacuo to yield intermediate compound I-33 (3.09 g, quant.) as a brown solid which was used in the following step without further purification.

Intermediate 34 (I-34)

6-Chloro-3-iodo-2-methoxy-pyridine (I-34)

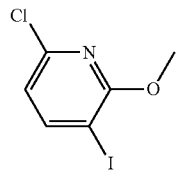

To a suspension of copper(I) iodide (7.86 g, 41.3 mmol) and tert-butyl nitrite (48 mL, 41.3 mmol) in MeCN (600 mL), intermediate I-33 in MeCN (600 mL) was added slowly at 0° C. for 5 min. The mixture was stirred at 0° C. for 1 h. Then it was stirred at 65° C. for 1 h. The crude was filtered over celite. The mixture was diluted with water and extracted with Et$_2$O. The organic phase was separated, dried (Na$_2$SO$_4$), filtered and the solvents concentrated in vacuo to yield intermediate compound I-34 (7.96 g, 71%) as a brown oil that was used in the next reaction step without any further purification.

Intermediate 35 (I-35)

6-Chloro-2-methoxy-3-(trifluoromethyl)pyridine (I-35)

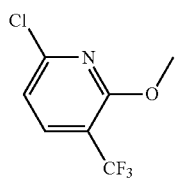

Copper(I) iodide (8.44 g, 44.3 mmol) was added to a stirred suspension of intermediate I-34 (7.96 g, 29.53 mmol) and methyl fluorosulphonyldifluoroacetate (8.6 mL, 67.9 mmol) in DMF (60 mL). The mixture was stirred at 100° C. for 16 h. The crude was filtered through celite. The mixture was diluted with Et$_2$O and extracted with a sat. sol. of NH$_4$C$_1$. The organic layer was separated, dried (Na$_2$SO$_4$), filtered and the solvents concentrated in vacuo carefully (without heating) to yield intermediate compound I-35 (8.92 g, 55% pure, 78%).

Intermediate 36 (I-36)

(7S)-5-[6-Methoxy-5-(trifluoromethyl)-2-pyridyl]-7-methyl-6,7-dihydropyrazolo[1,5-a]pyrazin-4-one (I-36)

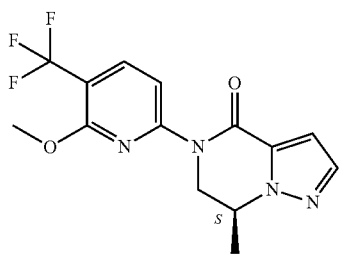

Pd(PPh$_3$)$_4$ (4.39 g, 3.798 mmol) was added to a stirred suspension of intermediate I-10 (5.74 g, 37.98 mmol), intermediate I-35 (14.88 g, 37.98 mmol), Xantphos (4.40 g, 7.60 mmol), Cs$_2$CO$_3$ (24.75 g, 75.958 mmol) in 1,4-dioxane (140 mL) in a sealed tube and under nitrogen. The mixture was stirred at 100° C. for 16 h. The mixture was filtered through a pad of diatomaceous earth and washed with DCM. The organic layer was evaporated in vacuo. The crude product was purified by flash column chromatography (silica, EtOAc in DCM 0/100 to 50/50). The desired fractions were collected, concentrated in vacuo. Then obtained product was purified again by flash column chromatography (silica, EtOAc in DCM 0/100 to 20/80). The desired fractions were collected, concentrated in vacuo to yield intermediate compound I-36 (5.52 g, 44%) as a brown oil that solidified upon standing at rt.

Intermediate 37 (I-37)

(7S)-5-[3-(fluoromethyl)-4-(trifluoromethyl)phenyl]-7-methyl-6,7-dihydropyrazolo[1,5-a]pyrazin-4-one (I-37)

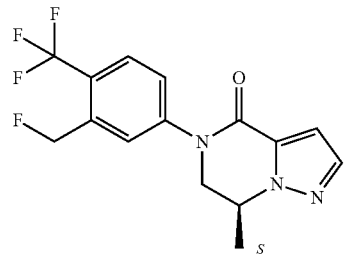

Bis(2-methoxyethyl)amino-sulfur trifluoride (4.85 mL, 26.33 mmol) was added to a stirred solution of intermediate I-28 (1.71 g, 5.26 mmol) in DCM (30 mL) at 0° C. and under nitrogen. The mixture was allowed to warm up to rt and stirred at rt for 17 h. Then it was treated with a sat. sol. NaHCO$_3$ at 0° C. and extracted with EtOAc. The organic layer was separated, dried (Na$_2$SO$_4$), filtered and concentrated in vacuo. The crude product was purified by flash column chromatography (silica; EtOAc in DCM 0/100 to 30/70). The desired fractions were collected and concentrated in vacuo to yield intermediate compound I-37 (1.1 g, 64%) as colorless oil that solidified upon standing at rt.

Intermediate 38 (I-38)

3-Iodo-7S-methyl-5-(4-trifluoromethyl-phenyl)-6,7-dihydro-5H-pyrazolo [1,5-a]pyrazin-4-one (I-38)

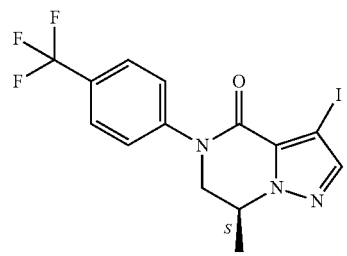

Iodine (11.55 g, 45.5 mmol) was added to a solution of intermediate I-15 (19.2 g, 65.0 mmol) and ammonium cerium(IV) nitrate (24.95 g, 45.5 mmol) in MeCN (350 mL). The mixture was stirred at 70° C. for 1 h. Then the mixture was diluted with EtOAc and washed with a sat. sol. of Na$_2$S$_2$O$_3$ and brine. The organic layer was separated, dried (Na$_2$SO$_4$), filtered and the solvents evaporated in vacuo. The residue was precipitated with DIPE and then was purified by short column chromatography (silica, DCM) then by flash column chromatography (silica; DCM in heptane 50/50 to 100/0). The desired fractions were collected and the solvents evaporated in vacuo to yield intermediate compound I-38 as a solid (24.8 g, 90%).

In a procedure analogous to that described for intermediate I-38, the following intermediates were synthesized:

| Starting Material | Intermediate obtained | |
|---|---|---|
| I-16 | (3,4-dichlorophenyl derivative) | I-39 |
| I-17 | (3-methyl-4-trifluoromethylphenyl derivative) | I-40 |
| I-18 | (3-fluoro-4-trifluoromethylphenyl derivative) | I-41 |
| I-19 | (3-chloro-4-trifluoromethylphenyl derivative) | I-42 |
| I-20 | (5-trifluoromethylpyridin-2-yl derivative) | I-43 |
| I-21 | (4-chlorophenyl derivative) | I-44 |
| I-22 | (3-methoxy-4-trifluoromethylphenyl derivative) | I-45 |
| I-23 | (3-cyano-4-trifluoromethylphenyl derivative) | I-46 |
| I-24 | (3-methoxymethyl-4-trifluoromethylphenyl derivative) | I-47 |
| I-25 | (3-chloro-4-difluoromethylphenyl derivative) | I-48 |
| I-26 | (4-chloro-3-difluoromethoxyphenyl derivative) | I-49 |
| I-27 | (4-chloro-3-methylphenyl derivative) | I-50 |

-continued

| Starting Material | Intermediate obtained | |
|---|---|---|
| I-31 | 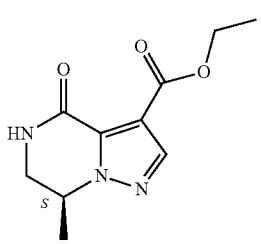 | I-51 |
| I-37 | | I-52 |
| I-29 | | I-53 |
| I-30 | | I-54 |
| I-32 | | I-55 |
| I-98 | 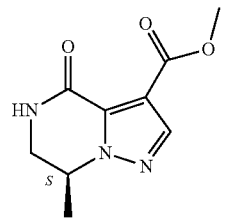 | I-99 |

Intermediate 56 (I-56)

Ethyl (7S)-7-methyl-4-oxo-6,7-dihydro-5H-pyrazolo[1,5-a]pyrazine-3-carboxylate (I-56)

Et₃N (12 mL, 86.62 mmol) was added to a mixture of intermediate I-9 (8 g, 28.87 mmol), Pd(OAc)₂ (129 mg, 0.577 mmol) and dppf (640 mg, 1.155 mmol) in EtOH (30 mL) and 1,4-dioxane (30 mL) under CO atmosphere (6 atm) at 95° C. for 18 h. The mixture was diluted with sat. NaHCO₃ and EtOAc was added. The aqueous phase was extracted with EtOAc and DCM/MeOH 9/1. The combined organics were dried (MgSO₄), filtered and evaporated. The crude product was purified by flash column chromatography (silica; EtOAc in DCM 5/100 to 70/30). The desired fractions were collected and concentrated in vacuo to yield intermediate compound I-56 (5 g, 74%) as a beige solid.

Intermediate 56'(I-56')

Intermediate 56' was synthesized following a procedure analogous to that described for I-56, starting from I-9, and using Pd(dppf)Cl₂ as catalyst and DMF as solvent. After the reaction took place, the reaction mixture was filtered through diatomaceous earth, the solvents concentrated and the crude product purified by flash column chromatography (silica; EtOAc in petroleum ether 1/10 to 1/0).

In a procedure analogous to that described for intermediate I-15, the following intermediates were synthesized:
| Starting Material | Reagent | Intermediate Product | |
|---|---|---|---|
| I-56 | 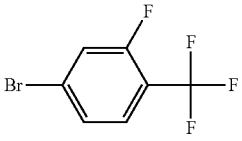 [SMILES: Fc1cc(Br)ccc1C(F)(F)F] |  | I-57 |
| I-56 | 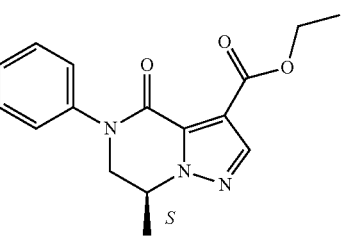 | 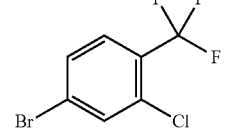 | I-58 |
| I-56' | 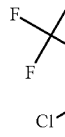 | 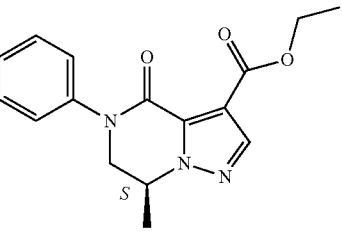 | I-58' |
| I-56 | 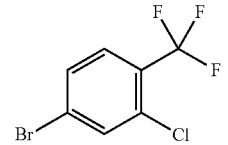 [SMILES: FC(F)(F)c1ccc(Br)cc1Cl] | 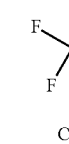 | I-59 |
| I-56' | 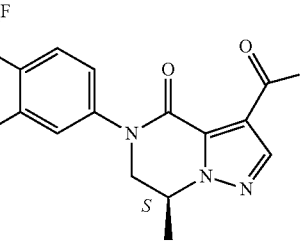 | 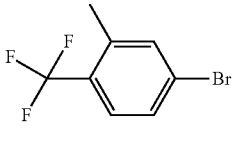 | I-I-59' |
| I-56 |  | 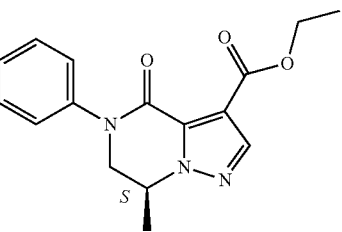 | I-60 |

-continued
| Starting Material | Reagent | Intermediate Product | |
|---|---|---|---|
| I-56 | 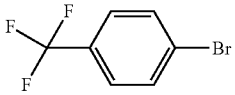 | 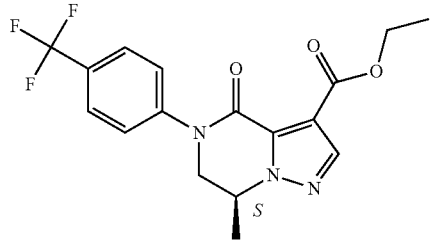 | I-61 |
| I-56 | 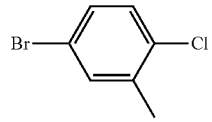 | 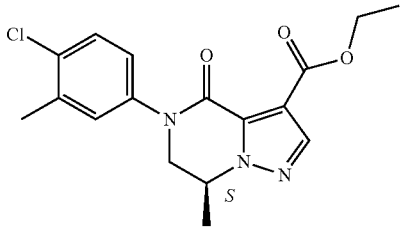 | I-62 |
| I-56 | 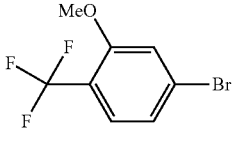 | 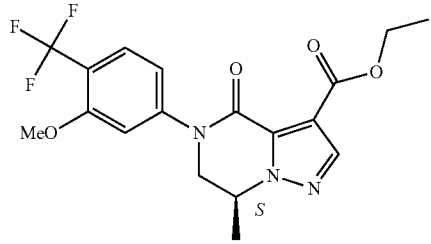 | I-63 |
| I-56 | 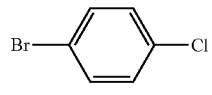 | 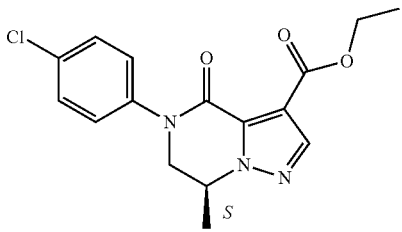 | I-64 |
| I-56' | 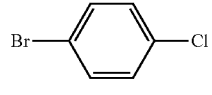 | 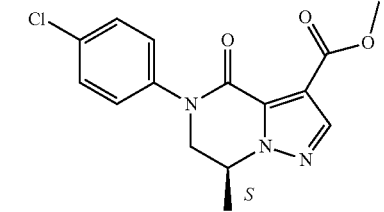 | I-64' |

Intermediate 65 (I-65)

(7S)-7-Methyl-4-oxo-5-[4-(trifluoromethyl)phenyl]-6,7-dihydropyrazolo [1,5-a]pyrazine-3-carbonitrile (I-65)

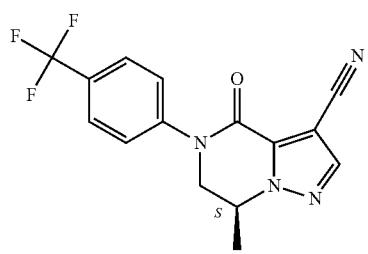

A mixture of intermediate I-35 (1.6 g, 3.80 mmol), zinc cyanide (579 mg, 4.94 mmol) and PdCl$_2$(dppf) (139 mg, 0.19 mmol) in DMF (14.7 mL) was stirred at 150° C. for 16 h. The crude product was filtered through a pad of diatomaceous earth and the solvent was evaporated in vacuo. The crude product was purified by flash column chromatography (silica; DCM). The desired fractions were collected and evaporated in vacuo to give intermediate compound I-65 (1.21 g, 99%).

Following a procedure analogous to that described for intermediate I-65, the following intermediate was also synthesized:

| Starting Material | Intermediate | |
|---|---|---|
| I-39 | | I-66 |
| I-42 | | I-67 |
| I-52 | | I-68 |

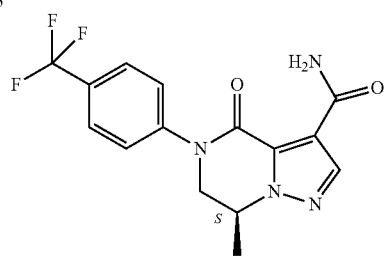

Intermediate 69 (I-69)

(7S)-7-methyl-4-oxo-5-[4-(trifluoromethyl)phenyl]-6,7-dihydropyrazolo [1,5-a]pyrazine-3-carboxamide (I-69)

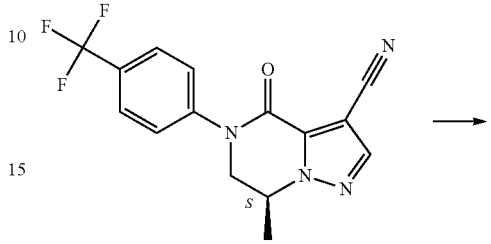

I-65

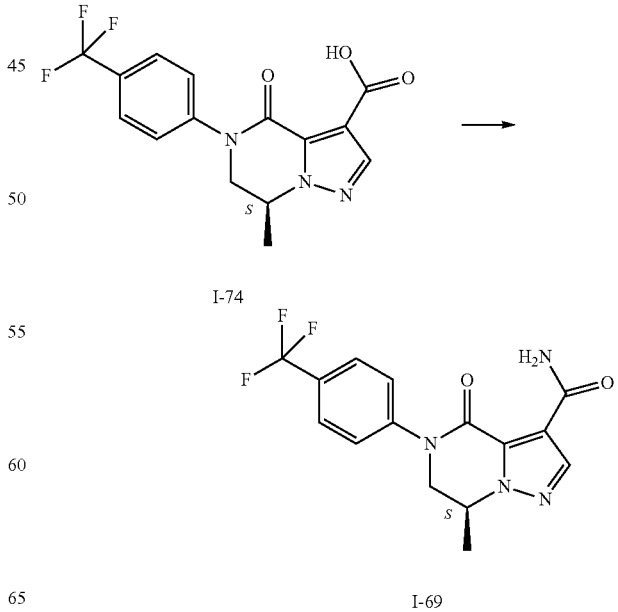

I-69

Procedure A): A mixture of intermediate I-65 (468 mg, 1.461 mmol) in concentrated sulfuric acid (2.3 mL) was stirred at rt for 18 h. The mixture was poured onto ice and then it was carefully basified with an aq sol. NH$_4$OH. The mixture was extracted with EtOAc. The organic layer was separated, dried (Na$_2$SO$_4$), filtered and the solvents concentrated in vacuo to yield intermediate compound I-69 (488 mg, 99%) as a white solid.

Procedure B): HBTU (285 mg, 0.752 mmol) was added portionwise to a stirred solution of intermediate I-74 (170 mg, 0.501 mmol), NH₄Cl (53 mg, 1.002 mmol) and DIPEA (0.248 mL, 1.503 mmol) in DMF (5 mL). The mixture was stirred at rt for 3 days. The mixture was poured into sat. sol. NaHCO₃ and extracted with EtOAc. The organic layer was separated, dried (MgSO₄), filtered and evaporated in vacuo. The crude was purified by reverse phase from 75% H₂O (25 mM NH₄HCO₃)–25% MeCN—MeOH to 0% H₂O (25 mM NH₄HCO₃)–100% MeCN-MeOH. The desired fractions were collected and the solvents concentrated in vacuo. The crude product was triturated with DIPE to yield intermediate compound I-69 (145 mg, 86%) as a white solid.

Intermediate 70 (I-70)

Methyl (7S)-7-methyl-4-oxo-5-[4-(trifluoromethyl)phenyl]-6,7-dihydropyrazolo [1,5-a]pyrazine-3-carboxylate (I-70)

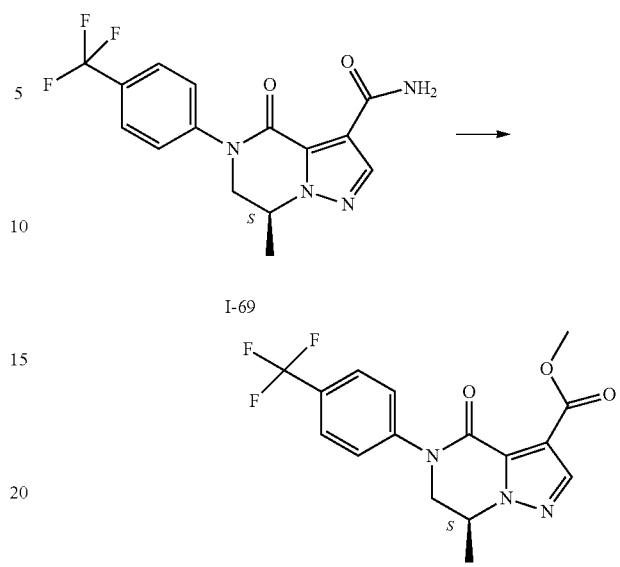

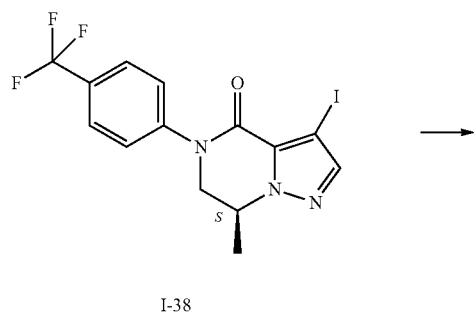

Procedure B): To a solution of intermediate I-69 (780 mg, 2.31 mmol) in MeOH (9.3 mL) was added N,N-dimethylformamide dimethyl acetal (0.92 mL, 6.92 mmol) at rt. The mixture was stirred at 45° C. for 24 h. The mixture was diluted with sat. aq. NH₄Cl and extracted with DCM. The organic layer was dried (Na₂SO₄), filtered and concentrated in vacuo to yield intermediate I-70 (795 mg, 97%) as a white solid.

Following a procedure analogous to procedure A) described for intermediate I-70, the following intermediates were also synthesized:

| Starting Material | Intermediate Product |
|---|---|
| I-54 | I-71 |
| I-51 | I-72 |

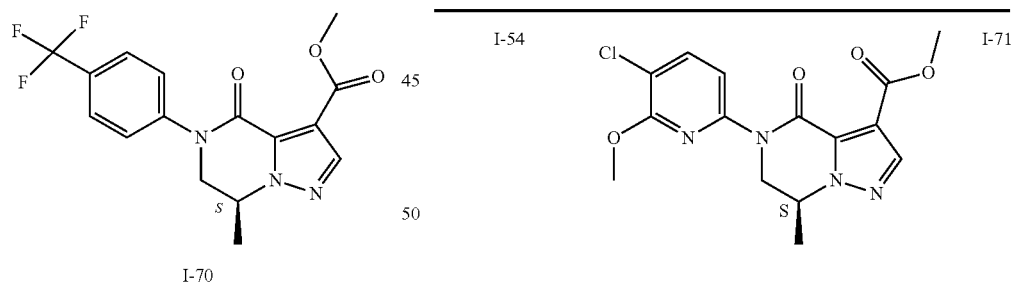

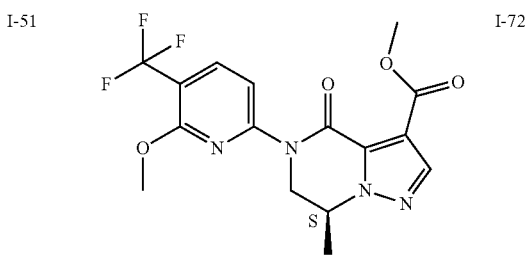

Procedure A): A mixture of intermediate I-38 (1.5 g, 3.56 mmol), Pd(OAc)₂ (16 mg, 0.071 mmol), dppf (78 mg, 0.142 mmol) and Et₃N (1.48 mL, 10.68 mmol) in MeOH (15 mL) and 1,4-dioxane (15 mL) was stirred under CO atmosphere (6 atm) at 95° C. for 18 h. The mixture was diluted with sat. sol. NaHCO₃ and EtOAc were added. The aqueous phase was extracted once more. The combined organic layers were washed with water (×2), brine (×2), dried (MgSO₄), filtered and evaporated in vacuo. The crude product was purified by flash column chromatography (silica; EtOAc in Heptane 0/100 to 70/30). The desired fractions were collected and concentrated in vacuo to yield intermediate compound I-70 (1.23 g, 95%) as a beige solid.

-continued

| Starting Material | Intermediate Product |
|---|---|
| I-53 | I-73 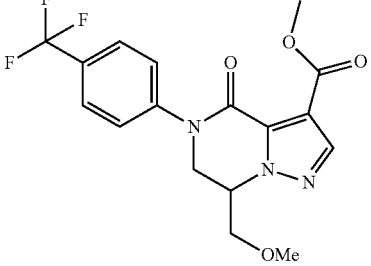 |

| Starting Material | Intermediate Product |
|---|---|
| I-73 | I-96 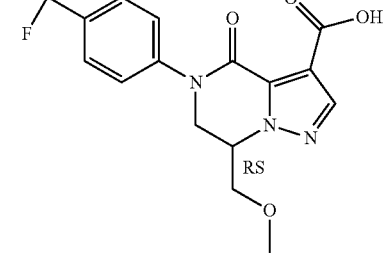 |

Intermediate 74 (I-74)

(7S)-7-methyl-4-oxo-5-[4-(trifluoromethyl)phenyl]-6,7-dihydropyrazolo [1,5-a]pyrazine-3-carboxylic acid (I-74)

Procedure B): LiOH (2 mg, 0.078 mmol) was added to a stirred mixture of intermediate I-70 (25 mg, 0.071 mmol) in 1,4-dioxane (1 mL) and water (0.1 mL) at rt. The mixture was stirred at rt for 24 h and the solvents were concentrated in vacuo to yield intermediate compound I-74 (23 mg, 74%) which was used without further purification.

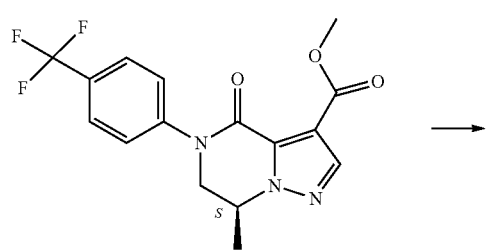

I-70

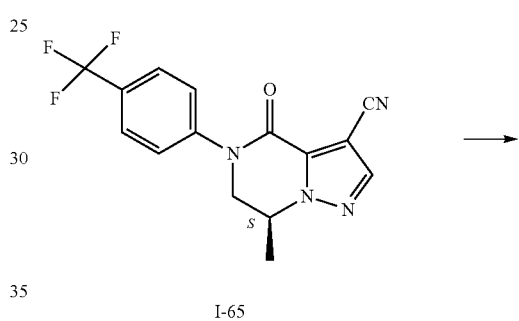

I-65

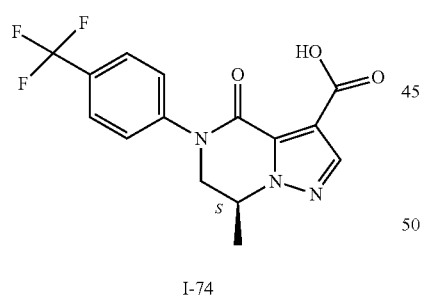

I-74

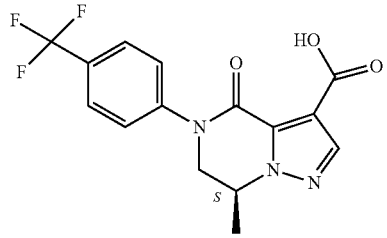

I-74

Procedure A): NaOH (2 M in water, 0.743 mL, 1.486 mmol) was added to a mixture of intermediate I-70 (500 mg, 1.415 mmol) in MeOH (5 mL). The mixture was stirred at 50° C. for 4 h. Then HCl (1 N) was added until pH=4-5 at 0° C. The mixture was diluted with EtOAc and washed with water. Then the organic layer was separated, dried (MgSO$_4$), filtered and the solvent evaporated in vacuo to yield intermediate compound I-74 (500 mg) as a beige solid which was used in the subsequent step without further purification.

Following a procedure analogous to procedure A) described for intermediate I-74, the following intermediates were also synthesized:

Procedure C): A stirred solution of intermediate I-65 (1.99 g, 6.213 mmol) in HCl (3.9 mL, 37% in water) was stirred at 110° C. for 18 h. Then, HCl (3.9 mL, 37% in water) was added and the mixture was stirred at 110° C. for 16 h. The mixture was allowed to reach rt and then the solvents were evaporated in vacuo. The residue was dissolved in water and extracted with DCM. The organic layer was separated, dried (Na$_2$SO$_4$), filtered and the solvents evaporated in vacuo to give intermediate compound I-74 (2 g, 95%) as a cream solid.

Intermediate 75 (I-75)

(7S)-5-[3-(fluoromethyl)-4-(trifluoromethyl)phenyl]-7-methyl-4-oxo-6,7-dihydropyrazolo[1,5-a]pyrazine-3-carboxylic acid I-75

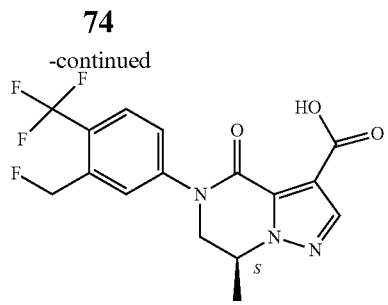

I-75

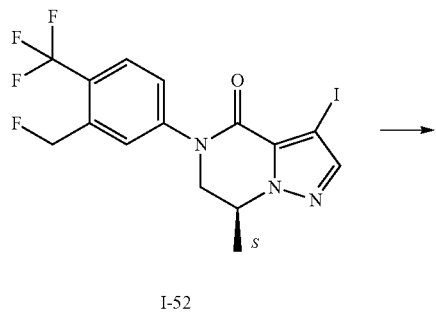

I-52

Procedure D): Et₃N (0.174 mL, 1.257 mmol) was added to a mixture of intermediate I-52 (170 mg, 0.375 mmol), Pd(OAc)₂ (2 mg, 0.008 mmol), dppf (9 mg, 0.016 mmol), 3-aminopyridine (35 mg, 0.375 mmol) in 1,4-dioxane (30 mL). The mixture was stirred under CO atmosphere (6 atm) at 90° C. for 18 h. The mixture was filtered and concentrated in vacuo. The crude was purified by flash column chromatography (silica; DCM/MeOH 9:1 in DCM 5/95 to 70/30). The desired fractions were collected and concentrated in vacuo to yield intermediate compound I-75 (160 mg, 85% pure, 98%).

Following procedures A)-D) as indicated, analogous to those described for intermediates I-74 and I-75, the following compounds were also synthesized:

| Starting Material | Procedure | Intermediate Product | |
|---|---|---|---|
| I-58<br>I-42 | A)<br>D) | *structure with CF₃, F, Cl substituents on phenyl, pyrazolo[1,5-a]pyrazine with COOH* | I-76 |
| I-59<br>I-40 | A)<br>D) | *structure with CF₃, F, methyl substituents on phenyl, pyrazolo[1,5-a]pyrazine with COOH* | I-77 |
| I-60<br>I-66<br>I-39 | A)<br>C)<br>D) | *structure with 3,4-dichlorophenyl, pyrazolo[1,5-a]pyrazine with COOH* | I-78 |

-continued

| Starting Material | Procedure | Intermediate Product | |
|---|---|---|---|
| I-71 | A) | [5-(5-chloro-6-methoxypyridin-2-yl)-4-oxo-(7S)-methyl-4,5,6,7-tetrahydropyrazolo[1,5-a]pyrazine-3-carboxylic acid] | I-79 |
| I-57<br>I-41 | A)<br>D) | [5-(3-fluoro-4-(trifluoromethyl)phenyl)-4-oxo-(7S)-methyl-4,5,6,7-tetrahydropyrazolo[1,5-a]pyrazine-3-carboxylic acid] | I-80 |
| I-62 | A) | [5-(4-chloro-3-methylphenyl)-4-oxo-(7S)-methyl-4,5,6,7-tetrahydropyrazolo[1,5-a]pyrazine-3-carboxylic acid] | I-81 |
| I-63 | A) | [5-(3-methoxy-4-(trifluoromethyl)phenyl)-4-oxo-(7S)-methyl-4,5,6,7-tetrahydropyrazolo[1,5-a]pyrazine-3-carboxylic acid] | I-82 |
| I-64<br>I-44 | A)<br>D) | [5-(4-chlorophenyl)-4-oxo-(7S)-methyl-4,5,6,7-tetrahydropyrazolo[1,5-a]pyrazine-3-carboxylic acid] | I-83 |
| I-55 | D) | [5-phenyl-4-oxo-(7S)-methyl-4,5,6,7-tetrahydropyrazolo[1,5-a]pyrazine-3-carboxylic acid] | I-84 |

-continued

| Starting Material | Procedure | Intermediate Product | |
|---|---|---|---|
| I-47 | D) | 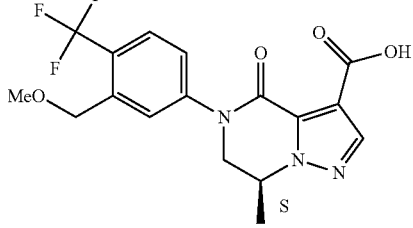 | I-85 |

Intermediate 86 (I-86)

(7S)-3-(aminomethyl)-7-methyl-5-[4-(trifluoromethyl)phenyl]-6,7-dihydropyrazolo[1,5-a]pyrazin-4-one (I-86)

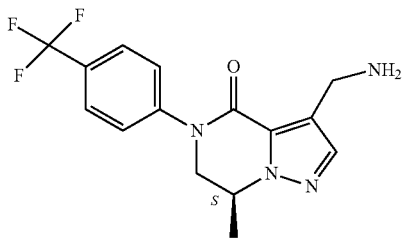

A solution of intermediate I-65 (440 mg, 1.374 mmol) in 7 M $NH_3$ in MeOH (26.4 mL) was hydrogenated in an H-Cube® reactor (Raney Ni short cartridge, 1 mL/min, 80° C., full Hz, 2 cycles). The solvent was concentrated in vacuo to yield intermediate compound I-86 (460 mg, 98%) as a colorless oil.

Intermediate 87 (I-87)

(2,4,6-Trichlorophenyl) (7S)-7-methyl-4-oxo-5-[4-(trifluoromethyl)phenyl]-6,7-dihydropyrazolo[1,5-a]pyrazine-3-carboxylate (I-87)

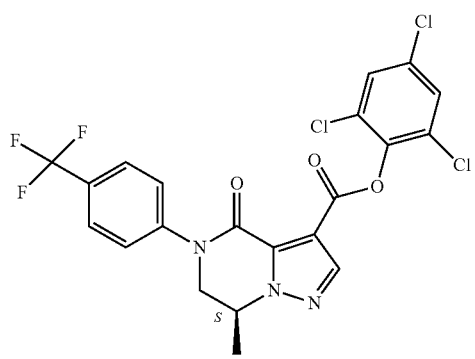

A mixture of intermediate I-38 (800 mg, 1.90 mmol), Pd(OAc)$_2$ (13 mg, 0.057 mmol), Xantphos (66 mg, 0.114 mmol) and Et$_3$N (0.528 mL, 3.80 mmol) in 1,4-dioxane (4.8 mL) was degassed for 5 min and then it was stirred under nitrogen at 70° C. for 5 min. Then a solution of 2,4,6-trichlorophenyl formate (prepared as described in Org. Lett. 2014, 5370-5373) (728 mg, 3.230 mmol) in degassed toluene (7.2 mL) was added with a syringe pump over 4 h. The crude product was filtered through a filter and the solvent was concentrated in vacuo. The crude product was purified by flash column chromatography (silica; DCM). The desired fractions were collected and evaporated in vacuo to give a residue which was purified by RP HPLC (Stationary phase: C$_{18}$ XBridge 30×100 mm 5 nm), Mobile phase: Gradient from 54% 0.1% NH$_4$CO$_3$H/NH$_4$OH pH 9 solution in Water, 46% MeCN to 64% 0.1% NH$_4$CO$_3$H/NH$_4$OH pH 9 solution in Water, 36% MeCN), to yield intermediate compound I-87 (390 mg, 80% pure, 31%).

Following a procedure analogous to that described for intermediate I-87, the following intermediates were also synthesized:

| Starting Material | Intermediate | |
|---|---|---|
| I-39 | 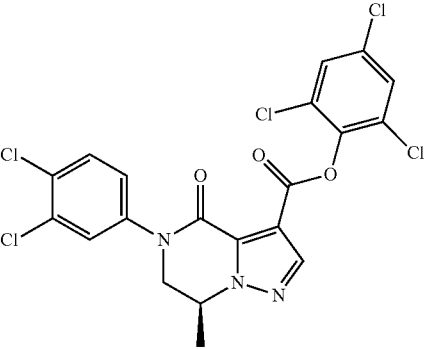 [SMILES: C[C@H]1CN(c2ccc(Cl)c(Cl)c2)C(=O)c2c(C(=O)Oc3c(Cl)cc(Cl)cc3Cl)cnn21] | I-88 |

Intermediate 89 (I-89)

(7S)—N-[[6-(2,5-Dimethylpyrrol-1-yl)-3-pyridyl]methyl]-7-methyl-4-oxo-5-[4-(trifluoromethyl)phenyl]-6,7-dihydropyrazolo[1,5-a]pyrazine-3-carboxamide (I-89)

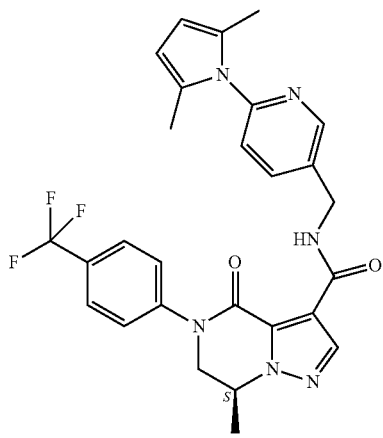

HBTU (0.101 g, 0.266 mmol) was added portionwise to a stirred solution of intermediate I-74 (60 mg, 0.177), 6-(2,5-dimethyl-1H-pyrrol-1-yl)-3-pyridinemethanamine (CAS: 1531539-96-4, 43 mg, 0.212 mmol) and DIPEA (87.8 µL, 0.531 mmol) in DMF (3 mL). The mixture was stirred at rt for two days. The mixture was diluted with sat. NaHCO$_3$ aq. sol. and extracted with EtOAc. Then the organic layer was separated, dried (MgSO$_4$), filtered and evaporated in vacuo. The crude product was purified by flash column chromatography (silica; EtOAc in DCM 5/100 to 30/70). The desired fractions were collected and the solvents concentrated in vacuo to yield intermediate compound I-89 (75 mg, 80%) as a colorless oil.

Intermediate 90 (I-90)

N-[[(7S)-7-methyl-4-oxo-5-[4-(trifluoromethyl)phenyl]-6,7-dihydropyrazolo [1,5-a]pyrazin-3-yl]methyl]cyclobutanecarboxamide (I-90)

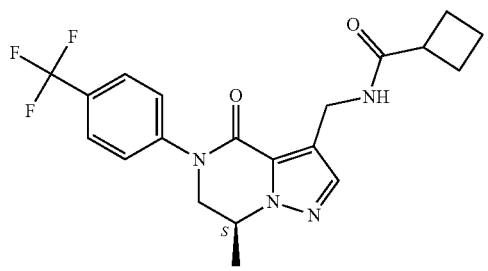

To a solution of intermediate I-86 (240 mg, 0.555 mmol), PyBOP® (289 mg, 0.555 mmol) and Et$_3$N (116 µL, 0.832 mmol) in DCM (2.1 mL) was added cyclobutanecarboxylic acid (56 mg, 0.555 mmol). The mixture was stirred at rt for 1 h. Then the mixture was diluted with water and extracted with DCM. The organic layer was dried (Na$_2$SO$_4$), filtered and concentrated in vacuo. The crude product was purified by flash column chromatography (silica; 7N NH$_3$ in MeOH/DCM 0/100 to 3/97). The desired fractions were collected and the solvents concentrated in vacuo. The residue was further purified by RP HPLC (Stationary phase: C18 XBridge 30×100 mm 5 µm; mobile phase: gradient from 67% 0.1% NH$_4$CO$_3$H/NH$_4$OH pH 9 solution in water, 33% MeCN to 50% 0.1% NH$_4$CO$_3$H/NH$_4$OH pH 9 solution in water, 50% MeCN), to yield intermediate compound I-90 (145 mg, 64%).

Intermediate 91 (I-91)

N-[[(7S)-7-methyl-4-oxo-5-[4-(trifluoromethyl)phenyl]-6,7-dihydropyrazolo[1,5-a]pyrazin-3-yl]methyl]acetamide (I-91)

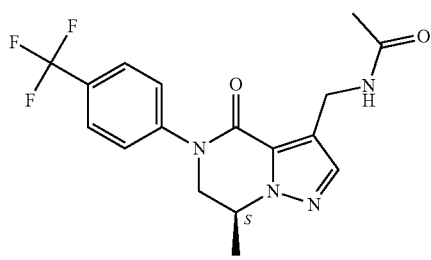

Acetyl chloride (52 µL, 0.74 mmol) was added to a stirred solution of intermediate I-86 (0.24 g, 0.74 mmol) and Et$_3$N (103 µL, 0.74 mmol) in DCM (5 mL) at −78° C. under nitrogen. The mixture was stirred at −78° C. for 1 h and then quenched by the addition of sat. aq. Na$_2$CO$_3$. The mixture was allowed to reach rt and the organic layer was separated, dried (Na$_2$SO$_4$), filtered and the solvents concentrated in vacuo. The crude product was purified by flash column chromatography (silica; MeOH in DCM 0/100 to 8/92) to yield intermediate compound I-91 (230 mg, 76% pure, 64%).

A sample was purified by RP HPLC (Stationary phase: C18 Sunfire 19×100 mm 5 µm, Mobile phase: Gradient from 80% 0.1% HCOOH solution in Water, 20% MeCN to 0% 0.1% HCOOH solution in Water, 100% MeCN) and the residue was dissolved in DCM and washed with aq. NaHCO$_3$. The organic layer was dried (Na$_2$SO$_4$), filtered and the solvents concentrated in vacuo to yield intermediate compound I-91 (20 mg) as a colorless oil.

Intermediate 92 (I-92)

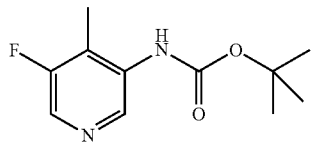 [SMILES: Cc1c(F)cncc1NC(=O)OC(C)(C)C]

Butyllithium (2.5M in hexanes, 13.3 mL, 33.21 mmol) was added dropwise to a stirred solution of (5-fluoro-3- pyridinyl)-carbamic acid 1,1-dimethylethyl ester (CAS: 342603-20-7, 2.82 g, 13.28 mmol) in THF (97 mL) at −78° C. (keeping Tint <−65° C.). The resulting mixture was warmed to −30° C. and stirred at this temperature for 2 h. The solution was cooled to −78° C. and methyl iodide (3.3 mL, 53.15 mmol) was added dropwise, (keeping Tint <−70° C.). The resulting solution was stirred at −78° C. for 1.5 h and then quenched by addition of water (5 mL). The mixture was diluted with EtOAc and water. The organic phase was separated, dried (Na$_2$SO$_4$), filtered and the solvents concentrated in vacuo. The crude product was purified by flash column chromatography (silica; EtOAc in Heptane 0/100 to 30/70). The desired fractions were collected and concentrated in vacuo to yield intermediate compound I-92 (2.67 g, 89%) as a pale yellow oil.

Intermediate 93 (I-93)

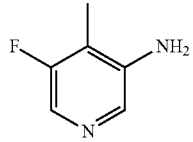

Trifluoroacetic acid (4.54 mL, 59.00 mmol) was added to a stirred solution of intermediate I-92 (2.67 g, 11.81 mmol) in DCM (42 mL). The mixture was stirred at rt for 1 h. The solvent was concentrated in vacuo. The residue was dissolved in DCM and washed with a sat sol of Na$_2$CO$_3$. The organic layer was separated, dried (Na$_2$SO$_4$), filtered and the solvents concentrated in vacuo to yield intermediate compound I-93 (1.07 g, 72%) as a pale brown solid. The aqueous phase was further extracted with DCM/EtOH (9/1). The organic layer was separated, dried (Na$_2$SO$_4$), filtered and the solvents concentrated in vacuo to yield a second fraction of intermediate compound I-93 (460 mg, 83% pure, 25%) as a brown oil.

Following a sequence analogous to that described for compound I-93, the following compounds were also synthesized:

| Reagent | Intermediate |
|---|---|
| 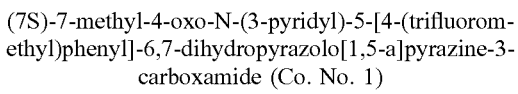 | |

Preparation of Final Compounds

Example 1 (E-1)

(7S)-7-methyl-4-oxo-N-(3-pyridyl)-5-[4-(trifluoromethyl)phenyl]-6,7-dihydropyrazolo[1,5-a]pyrazine-3-carboxamide (Co. No. 1)

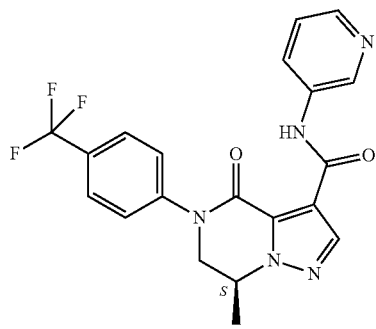

DMAP (70 mg, 0.575 mmol) was added to intermediate I-74 (130 mg, 0.383 mmol), 3-aminopyridine (36 mg, 0.383 mmol) in dry DCM (10 mL). Molecular sieves powder (1 g, 4 Å, activated) was added and the mixture was stirred at rt for 1 h. EDCI.HCl (110 mg, 0.575 mmol) was added portionwise and the mixture was stirred at rt for 24 h. The mixture was filtered through a pad of diatomaceous earth and the filtrate was washed twice with 10% aq. NH$_4$Cl sol. The organic layers were combined, dried (MgSO$_4$), filtered and the solvents evaporated in vacuo. The crude product was purified by flash column chromatography (silica; DCM/MeOH 20:1 in DCM 5/95 to 70/30). The desired fractions were collected and the solvents concentrated in vacuo. The solid was triturated with DIPE to yield final compound Co. No. 1 (141 mg, 87%) as a white solid. $^1$H NMR (300 MHz, CDCl$_3$) δ ppm 1.79 (d, J=6.6 Hz, 3H) 4.06 (dd, J=12.9, 7.3 Hz, 1H) 4.35 (dd, J=12.8, 4.3 Hz, 1H) 4.79-4.96 (m, 1H) 7.27-7.35 (m, 1H) 7.57 (d, J=8.4 Hz, 2H) 7.82 (d, J=8.4 Hz, 2H) 8.23-8.41 (m, 2H) 8.37 (s, 1H) 8.85 (br. s., 1H) 12.10 (br. s., 1H).

Following a procedure analogous to that described for E-1, the following compounds were also synthesized:

| Intermediate | Reagent | Final Compound | |
|---|---|---|---|
| I-74 | H₂N–C₆H₄–S(O)₂–CH₃ (3-methylsulfonylaniline) | [structure] | Co. No. 2 |
| I-74 | 4-aminopyridine | [structure] | Co. No. 3 |
| I-74 | 4-amino-3-fluoropyridine | [structure] | Co. No. 4 |
| I-74 | 4-amino-2-methylpyridine | [structure] | Co. No. 5 |

-continued
| Intermediate | Reagent | Final Compound | |
|---|---|---|---|
| I-74 | 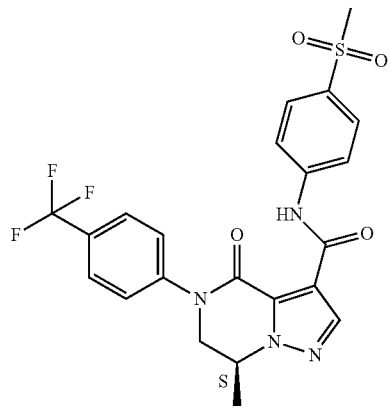 | 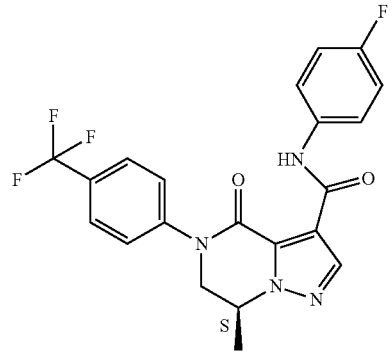 | Co. No. 6 |
| I-74 | 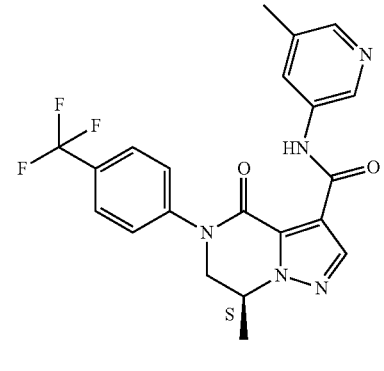 | 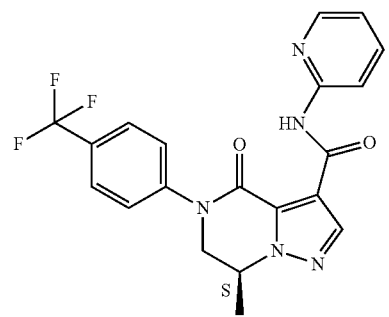 | Co. No. 7 |
| I-74 | | | Co. No. 8 |
| I-74 | | | Co. No. 9 |

-continued

| Intermediate | Reagent | Final Compound | |
|---|---|---|---|
| I-74 | 3-amino-2-methylpyridine | (structure) | Co. No. 10 |
| I-74 | 2-amino-3-methoxypyridine | (structure) | Co. No. 11 |
| I-74 | 2-amino-3-fluoropyridine | (structure) | Co. No. 12 (free base)<br>Co. No. 12a (HCl salt) |
| I-74 | 3-amino-5-fluoropyridine | (structure) | Co. No. 13 (free base)<br>Co. No. 13a (HCl salt) |

-continued

| Intermediate | Reagent | Final Compound | |
|---|---|---|---|
| I-74 | 4-methyl-pyridin-3-amine | | Co. No. 14 |
| I-74 | 3-methyl-pyridin-2-amine | | Co. No. 15 |
| I-74 | 3-methoxy-pyridin-4-amine | | Co. No. 16 |
| I-74 | 6-methyl-pyridin-2-amine | | Co. No. 17 |

-continued
| Intermediate | Reagent | Final Compound | |
|---|---|---|---|
| I-74 | 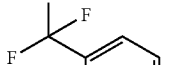 | 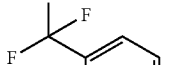 | Co. No. 18 |
| I-74 | 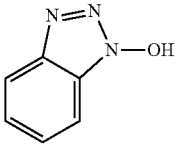 | 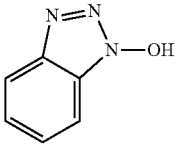 | Co. No. 19 |
| I-80 | 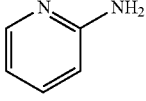 | 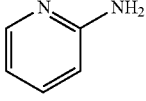 | Co. No. 20 (**) |
| I-80 | 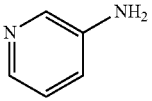 | 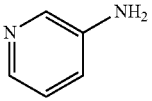 | Co. No. 21 (**) |

| Intermediate | Reagent | Final Compound | |
|---|---|---|---|
| I-80 | 3-amino-5-methylpyridine | | Co. No. 22 |
| I-80 | 3-amino-4-methylpyridine | | Co. No. 23 |
| I-80 | 3-amino-5-fluoropyridine | | Co. No. 24 |
| I-78 | 2-aminopyridine | | Co. No. 25 (**) |

| Intermediate | Reagent | Final Compound | |
|---|---|---|---|
| I-78 | H₂N-(3-pyridyl) | (structure) | No. 26 (**) |
| I-78 | H₂N-(5-fluoro-3-pyridyl) | (structure) | Co. No. 27 |
| I-78 | H₂N-(5-methyl-3-pyridyl) | (structure) | Co. No. 28 |
| I-78 | H₂N-(5-methoxy-3-pyridyl) | (structure) | Co. No. 29 |

-continued

| Intermediate | Reagent | Final Compound | |
|---|---|---|---|
| I-78 | 4-methylpyridin-3-amine | Co. No. 30 |
| I-85 | pyridin-2-amine | Co. No. 31 |
| I-82 | 4-methylpyridin-3-amine | Co. No. 32 |
| I-82 | 5-methylpyridin-3-amine | Co. No. 33 |

-continued
| Intermediate | Reagent | Final Compound | |
|---|---|---|---|
| I-82 | 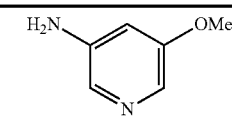 | 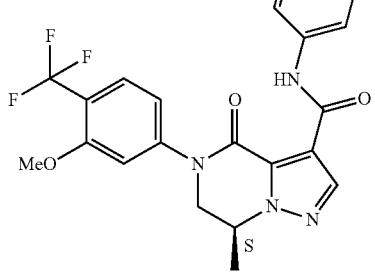 | Co. No. 34 |
| I-77 | 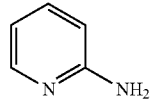 | 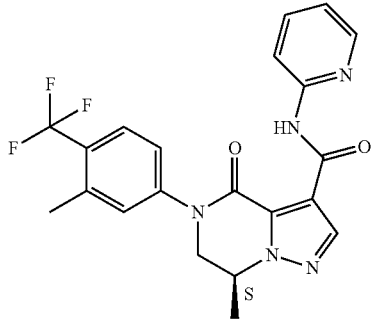 | Co. No. 35 (**) |
| I-77 | 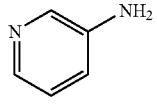 | 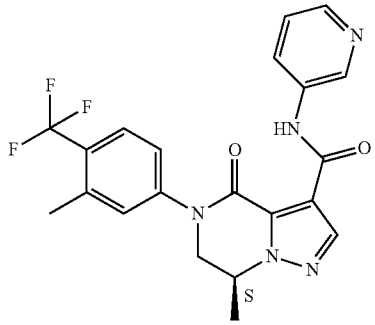 | Co. No. 36 (‡)(**) |
| I-77 | 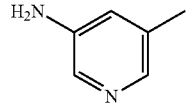 | 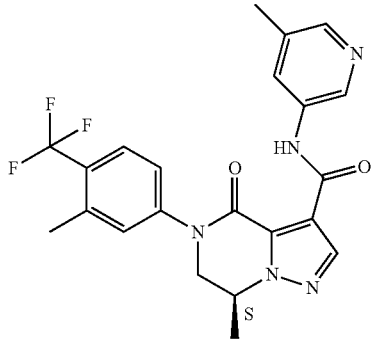 | Co. No. 37 |

-continued

| Intermediate | Reagent | Final Compound | |
|---|---|---|---|
| I-77 | 3-amino-4-methylpyridine | | Co. No. 38 |
| I-77 | 3-amino-5-fluoropyridine | | Co. No. 39 |
| I-77 | 3-amino-5-methoxypyridine | | Co. No. 40 |
| I-83 | 3-aminopyridine | | Co. No. 41 (‡)(**) |

-continued
| Intermediate | Reagent | Final Compound | |
|---|---|---|---|
| I-83 | 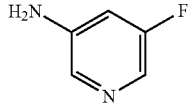 | 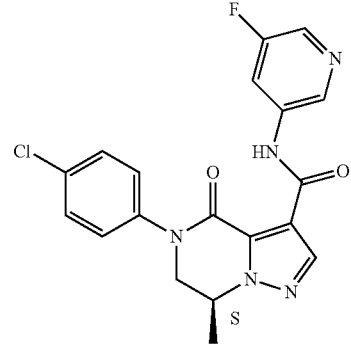 | Co. No. 42 |
| I-83 | 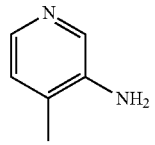 | 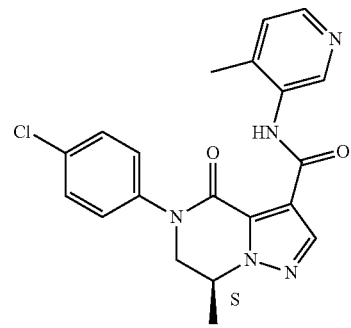 | Co. No. 43 |
| I-81 | 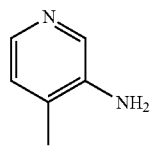 | 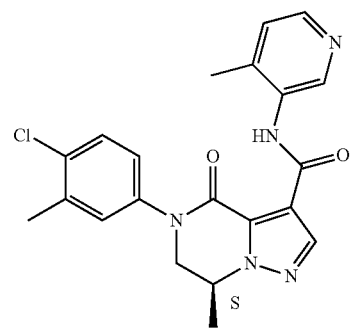 | Co. No. 44 |
| I-81 | 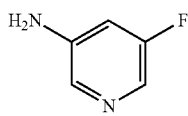 | 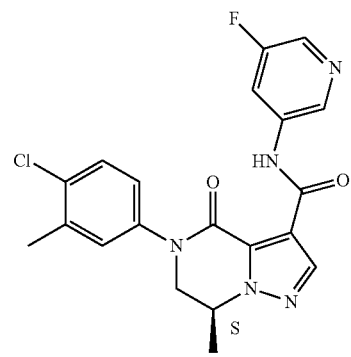 | Co. No. 45 |

-continued
| Intermediate | Reagent | Final Compound | |
|---|---|---|---|
| I-76 | 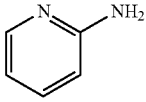 | 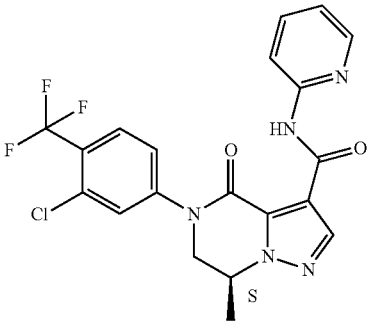 | Co. No. 46 (**) |
| I-76 | 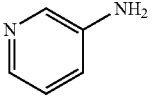 | 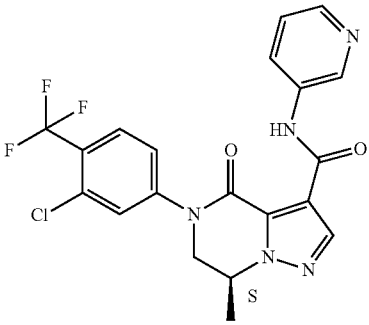 | Co. No. 47 (‡)(**) |
| I-76 | 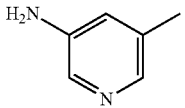 | 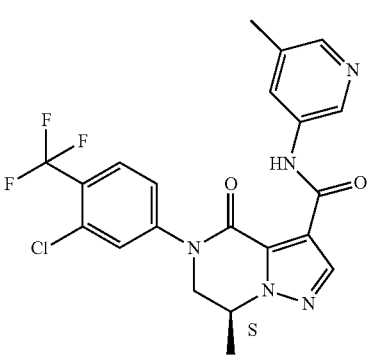 | Co. No. 48 |
| I-76 | 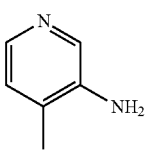 | 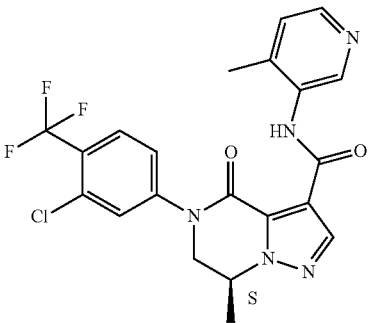 | Co. No. 49 (•HCl) |

-continued
| Intermediate | Reagent | Final Compound | |
|---|---|---|---|
| I-76 | 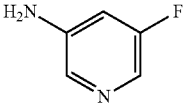 H₂N—⟨pyridine⟩—F | 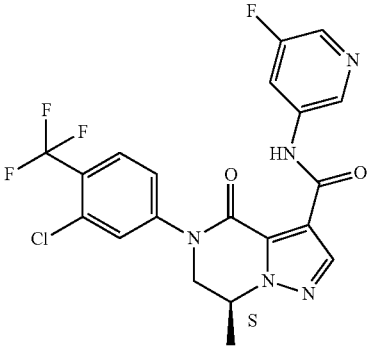 | Co. No. 50 |
| I-76 | 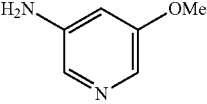 H₂N—⟨pyridine⟩—OMe | 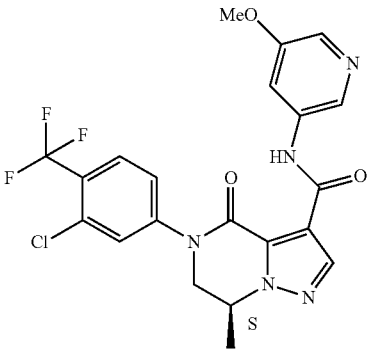 | Co. No. 51 |
| I-75 | 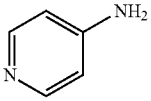 ⟨pyridine⟩—NH₂ | 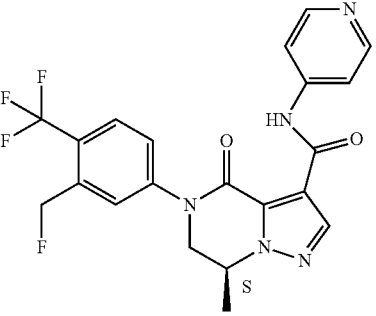 | Co. No. 52 (**) |
| I-75 | 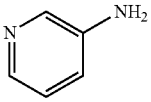 ⟨pyridine⟩—NH₂ | 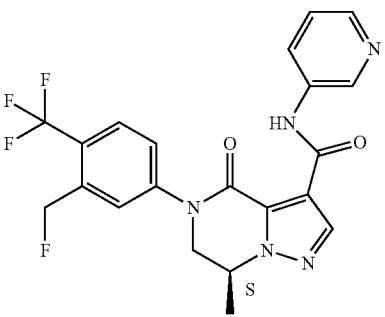 | Co. No. 53 |

-continued
| Intermediate | Reagent | Final Compound | |
|---|---|---|---|
| I-75 | 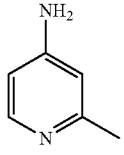 | 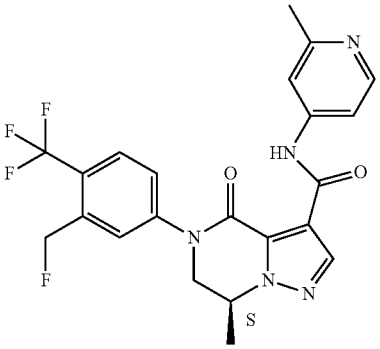 | Co. No. 54 (**) |
| I-74 | 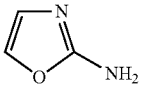 | 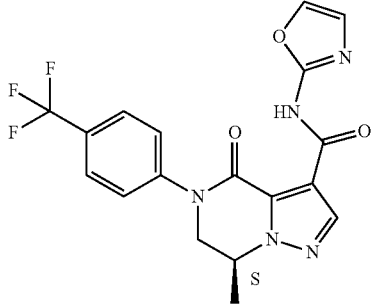 | Co. No. 139 |
| I-74 | 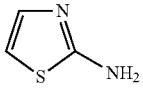 | 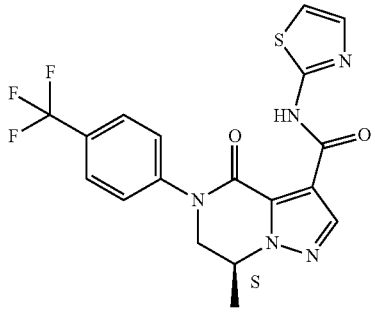 | Co. No. 140 |
| I-74 | 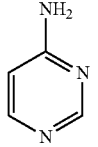 | 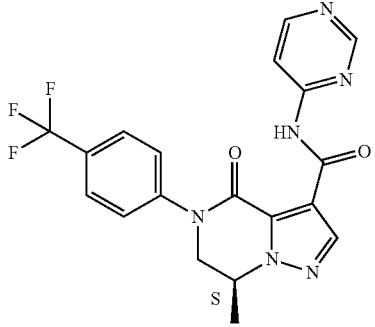 | Co. No. 141 |

| Intermediate | Reagent | Final Compound | |
|---|---|---|---|
| I-74 | 2-aminoimidazole | | Co. No. 142 |
| I-74 | 3-amino-5-methoxypyridine | | Co. No. 144 |
| I-82 | 3-amino-5-fluoropyridine | | Co. No. 117 |
| I-74 | 3-aminopyridine | | Co. No. 153 |

| Intermediate | Reagent | Final Compound | |
|---|---|---|---|
| I-96 | 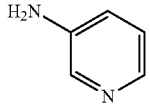 | 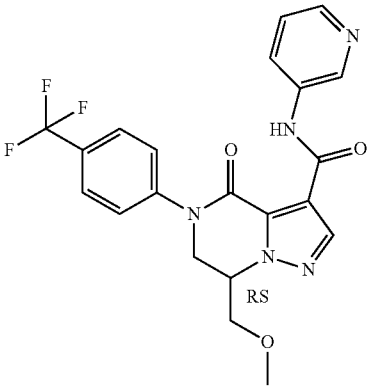 | Co. No. 165 |

Co No. 165 was purified by Chiral SFC (Stationary phase: CHIRALPAK IC 5 µm 250 × 20 mm, Mobile phase: 60% CO2, 40% iPrOH) to yield Co. No. 158 and Co. No. 159

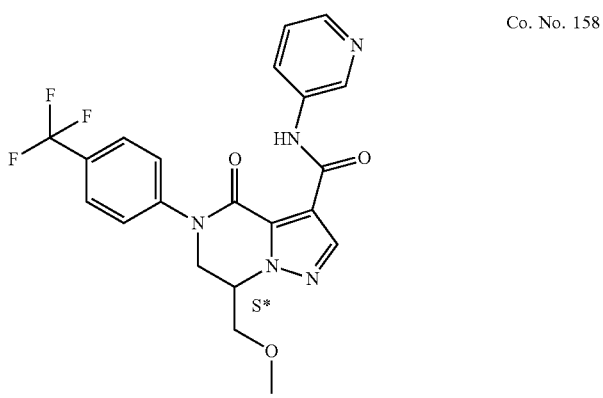

Co. No. 158

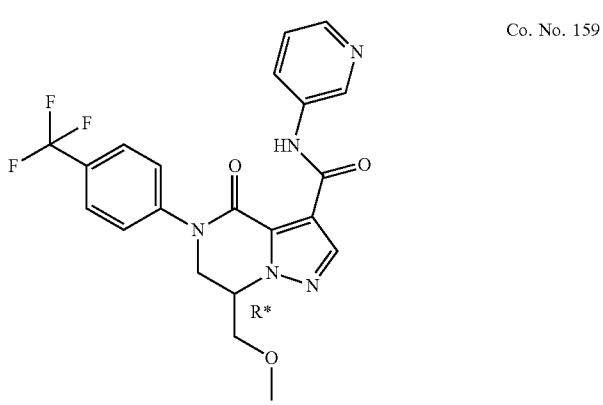

Co. No. 159

(‡) Compounds Co. No. 36, 41 and 47 were alternatively prepared according to a method analogous to that described in E-8, starting from I-59', I-64'and I-58', respectively;
(**) Compounds Co. No. 20, Co. No. 21, Co. No. 25, Co. No. 26, Co. No. 35, Co. No. 36, Co. No. 41, Co. No. 46, Co. No. 47, Co. No. 52, Co. No. 54 were alternatively prepared according to the method (different purification reverse phase solvent systems) described below, which resulted in the desired compound and the corresponding carboxylic acid species:

Example 1a (E-1a)

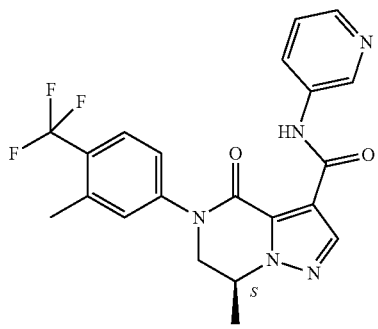
Co. No. 36

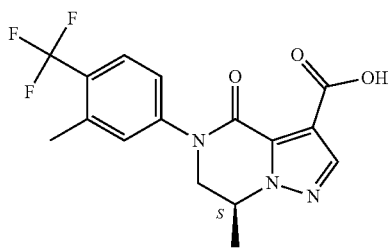
I-77

Et₃N (0.227 mL, 1.635 mmol) was added to a mixture of intermediate I-40 (237 mg, 0.544 mmol), Pd(OAc)$_2$ (2 mg, 0.011 mmol), ddpf (12 mg, 0.022 mmol), 3-aminopyridine (77 mg, 0.818 mmol) in 1,4-dioxane (30 mL) stirred at 90° C. for 18 h under CO atmosphere (6 atm). The mixture was filtered and the solvents concentrated in vacuo. The crude product was purified by reverse phase from 75% H$_2$O (0.1% TFA)–25% MeCN to 38% H$_2$O (0.1% TFA)–62% MeCN. Product was neutralized, concentrated and extracted with EtOAc to yield final compound Co. No. 36 (25 mg, 11%); intermediate compound I-77 (149 mg, 74%) was used in the subsequent step without further purification.

Following a procedure analogous to that described for compound Co. No. 36 and intermediate I-77 (E-1a), the following compounds and intermediates were also synthesized:

| Intermediate | Reagent | Final Compound |
|---|---|---|
| I-42 | 2-aminopyridine | Co. No. 46 | and

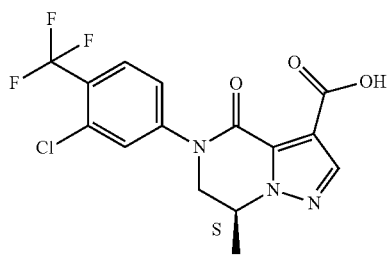
I-76

| Intermediate | Reagent | Final Compound | |
|---|---|---|---|
| I-40 |  | 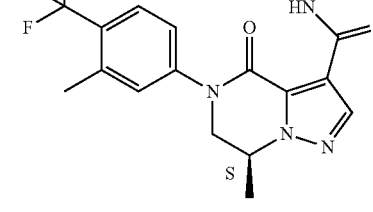 and 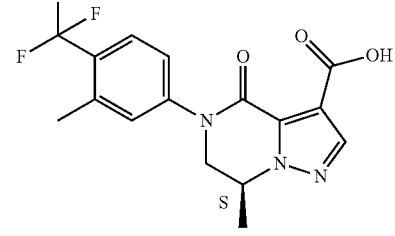 | Co. No. 35 I-77 |
| I-39 |  | 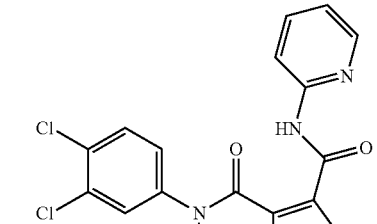 and 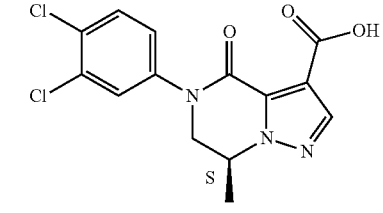 | Co. No. 25 I-78 |
| I-39 |  | 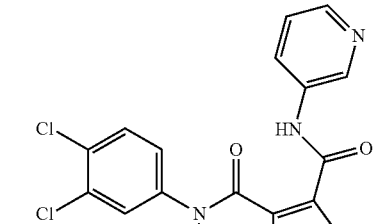 and | Co. No. 26 |

| Intermediate | Reagent | Final Compound | |
|---|---|---|---|
| | | (structure of I-78: 5-(3,4-dichlorophenyl)-4-oxo-7-methyl-4,5,6,7-tetrahydropyrazolo[1,5-a]pyrazine-3-carboxylic acid, S-configuration) | I-78 |
| I-41 | 2-aminopyridine | (structure: N-(pyridin-2-yl) amide of 5-(3-fluoro-4-(trifluoromethyl)phenyl)-7-methyl-4-oxo-4,5,6,7-tetrahydropyrazolo[1,5-a]pyrazine-3-carboxamide, S) and (I-80 carboxylic acid structure) | Co. No. 20 and I-80 |
| I-41 | 3-aminopyridine | (structure: N-(pyridin-3-yl) amide analog, S) and (I-80 carboxylic acid structure) | Co. No. 21 and I-80 |

| Intermediate | Reagent | Final Compound | |
|---|---|---|---|
| I-44 | 3-aminopyridine | [Co. No. 41: (S)-5-(4-chlorophenyl)-4-oxo-N-(pyridin-3-yl)-7-methyl-4,5,6,7-tetrahydropyrazolo[1,5-a]pyrazine-3-carboxamide] and [I-83: (S)-5-(4-chlorophenyl)-7-methyl-4-oxo-4,5,6,7-tetrahydropyrazolo[1,5-a]pyrazine-3-carboxylic acid] | Co. No. 41 / I-83 |
| I-42 | 3-aminopyridine | [Co. No. 47: (S)-5-(3-chloro-4-(trifluoromethyl)phenyl)-7-methyl-4-oxo-N-(pyridin-3-yl)-4,5,6,7-tetrahydropyrazolo[1,5-a]pyrazine-3-carboxamide] and [I-76: corresponding carboxylic acid] | Co. No. 47 / I-76 |
| I-52 | 4-aminopyridine | [Co. No. 52: (S)-5-(3-(fluoromethyl)-4-(trifluoromethyl)phenyl)-7-methyl-4-oxo-N-(pyridin-4-yl)-4,5,6,7-tetrahydropyrazolo[1,5-a]pyrazine-3-carboxamide] and | Co. No. 52 |

-continued

| Intermediate | Reagent | Final Compound | |
|---|---|---|---|
| | | [Structure of I-75: 5-(3-(difluoromethyl)-4-(trifluoromethyl)phenyl)-7-methyl-4-oxo-4,5,6,7-tetrahydropyrazolo[1,5-a]pyrazine-3-carboxylic acid, S-configuration] | I-75 |
| I-52 | [4-amino-2-methylpyridine] | [Structure of Co. No. 54: 5-(3-(difluoromethyl)-4-(trifluoromethyl)phenyl)-7-methyl-4-oxo carboxylic acid, S-configuration] | Co. No. 54 |
| | | and | |
| | | [Structure of I-75, S-configuration] | I-75 |
| I-99 | [3-aminopyridine] | [Structure of Co. No. 164: 5-(3-chloro-4-(trifluoromethyl)phenyl)-7-(methoxymethyl)-4-oxo-N-(pyridin-3-yl)-4,5,6,7-tetrahydropyrazolo[1,5-a]pyrazine-3-carboxamide, RS] | Co. No. 164 |

Co No. 164 was purified by
Chiral SFC (Stationary phase:
CHIRALPAK IC 5 μm
250 × 20 mm, Mobile phase: 60%
CO2, 40% MeOH) to yield Co.
No. 156 and Co. No. 157.

-continued

| Intermediate | Reagent | Final Compound |
|---|---|---|
| | | 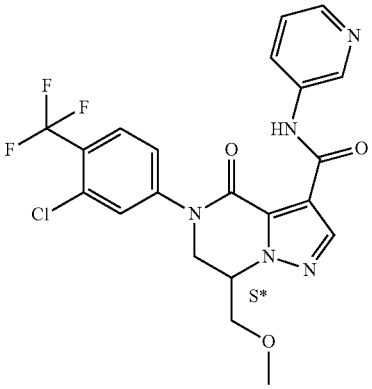
Co. No. 156 |
| | | 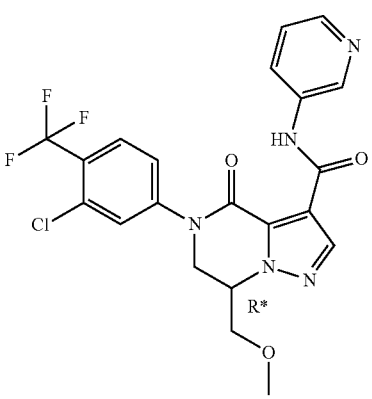
Co. No. 157 |

Example 2 (E-2)

(7S)—N-(6-fluoro-3-pyridyl)-7-methyl-4-oxo-5-[4-(trifluoromethyl)phenyl]-6,7-dihydropyrazolo[1,5-a]pyrazine-3-carboxamide (Co. No. 55)

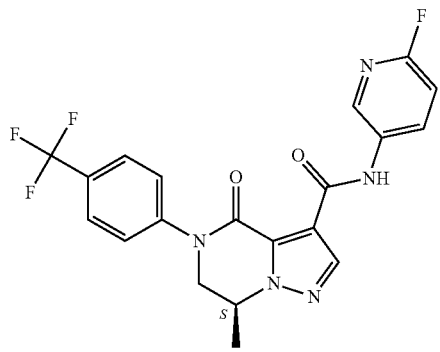

DMAP (2 mg, 0.019 mmol) was added to a stirred mixture of intermediate I-87 (200 mg, 0.385 mmol), 5-amino-2-fluoropyridine (86 mg, 0.771 mmol) and Et$_3$N (161 μL, 1.156 mmol) in THF (6.7 mL) at rt under nitrogen. The mixture was stirred at 70° C. for 18 h. The solvent was concentrated in vacuo. The crude product was purified by flash column chromatography (silica; 7N solution of ammonia in MeOH in DCM 0/100 to 3/97). The desired fractions were collected and the solvents evaporated in vacuo. The product was purified by RP HPLC (Stationary phase: C18 XBridge 30×100 mm 5 μm), Mobile phase: Gradient from 54% 0.1% NH$_4$CO$_3$H/NH$_4$OH pH 9 solution in Water, 46% MeCN to 64% 0.1% NH$_4$CO$_3$H/NH$_4$OH pH 9 solution in Water, 36% MeCN) to yield final compound Co. No. 55 (75 mg, 45%). $^1$H NMR (400 MHz, CDCl$_3$) δ ppm 1.77 (d, J=6.7 Hz, 3H) 4.05 (dd, J=12.9, 7.4 Hz, 1H) 4.33 (dd, J=12.8, 4.3 Hz, 1H) 4.85 (quind, J=6.7, 4.5 Hz, 1H) 6.89 (dd, J=8.8, 3.2 Hz, 1H) 7.55 (d, J=8.3 Hz, 2H) 7.80 (d, J=8.6 Hz, 2H) 8.28 (ddd, J=8.9, 7.1, 2.8 Hz, 1H) 8.34 (s, 1H) 8.45 (dd, J=2.3, 1.2 Hz, 1H) 12.08 (br. s, 1H).

Following a procedure analogous to that described for E-2, the following compounds were also synthesized:

| Intermediate | Reagent | Final compound |
|---|---|---|
| I-87 | H₂N-pyridine-NH₂ | Co. No. 19 |
| I-88 | F-pyridine-NH₂ | Co. No. 56 |

HBTU (251 mg, 0.663 mmol) was added portionwise to a stirred solution of intermediate I-74 (150 mg, 0.442 mmol), aniline (48 μL, 0.53 mmol) and DIPEA (219 μL, 1.326 mmol) in DMF (3 mL). The mixture was stirred at rt for 16 h. The mixture was diluted with sat. sol. NaHCO₃ and extracted with EtOAc. Then the organic layer was separated, dried (MgSO₄), filtered and the solvents evaporated in vacuo. The crude product was purified by reverse phase from 50% [25 mM NH₄HCO₃ pH=8]-50% [MeCN: MeOH 1:1] to 0%[25 mM NH₄HCO₃ pH=8]–100% [MeCN: MeOH 1:1]. The desired fractions were collected and the solvents concentrated in vacuo. The product was triturated with DIPE to yield final compound Co. No. 57 (115 mg, 62%) as a white solid. $^1$H NMR (300 MHz, CDCl₃) δ ppm 1.77 (d, J=6.6 Hz, 3H) 4.02 (dd, J=12.9, 7.3 Hz, 1H) 4.32 (dd, J=12.9, 4.3 Hz, 1H) 4.76-4.92 (m, 1H) 7.03-7.13 (m, 1H) 7.31 (t, J=7.9 Hz, 2H) 7.55 (d, J=8.2 Hz, 2H) 7.73 (d, J=7.6 Hz, 2H) 7.79 (d, J=8.4 Hz, 2H) 8.35 (s, 1H) 11.86 (br. s., 1H).

Example 3 (E-3)

(7S)-7-Methyl-4-oxo-N-phenyl-5-[4-(trifluoromethyl)phenyl]-6,7-dihydropyrazolo[1,5-a]pyrazine-3-carboxamide (Co. No. 57)

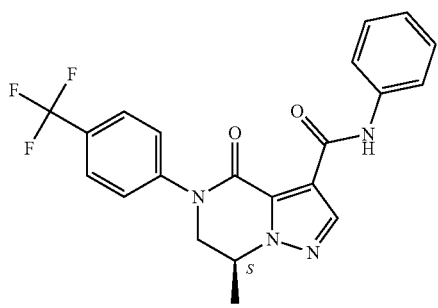

Following a procedure analogous to that described for E-3, the following compounds were also synthesized:
| Intermediate | Reagent | Final Compound |
|---|---|---|
| I-74 | 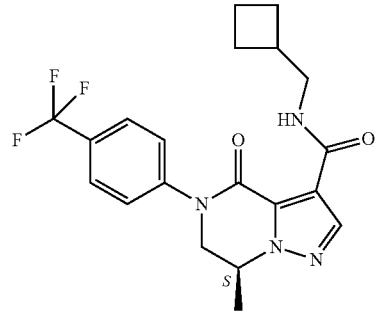 | 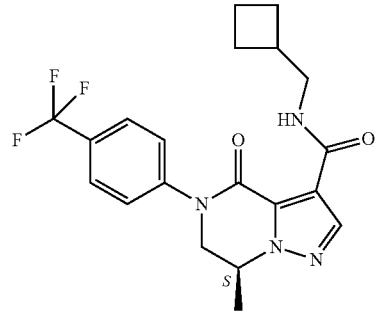 Co. No. 58 |
| I-74 | 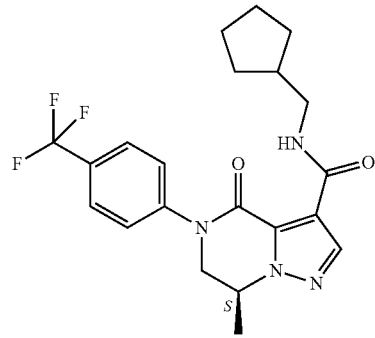 | 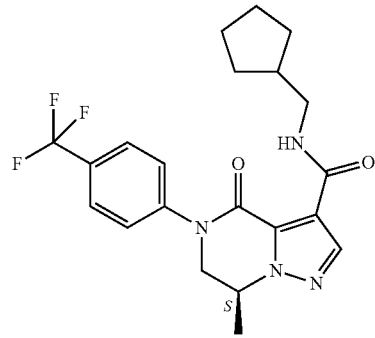 Co. No. 59 |
| I-74 | 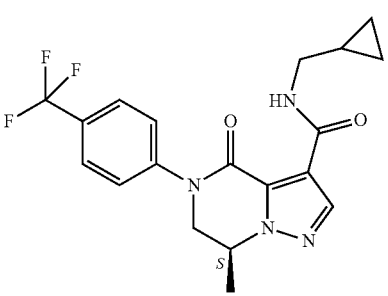 | 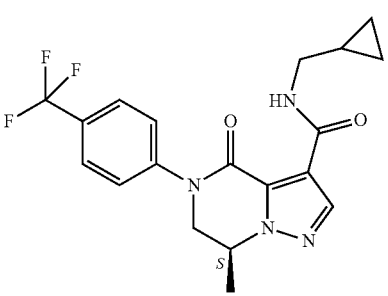 Co. No. 60 |
| I-74 | 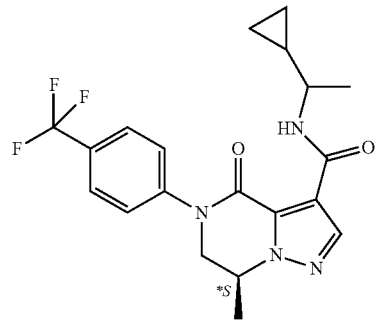 | 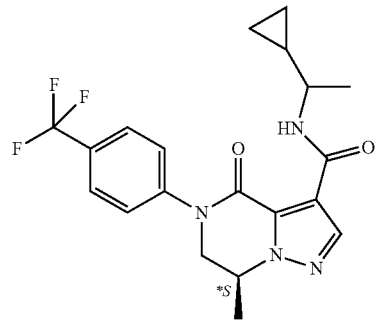 Co. No. 61 |

-continued

| Intermediate | Reagent | Final Compound |
|---|---|---|
| I-74 | tetrahydrofuran-2-ylmethanamine | Co. No. 62 |
| I-74 | (2-methylpyridin-4-yl)methanamine | Co. No. 63 |
| I-74 | tetrahydrofuran-3-ylmethanamine | Co. No. 64 |
| I-74 | cyclohexanamine | Co. No. 65 |

-continued

| Intermediate | Reagent | Final Compound |
|---|---|---|
| I-74 | 4-aminotetrahydropyran | Co. No. 66 |
| I-74 | benzylamine | Co. No. 67 |
| I-74 | tert-butylamine | Co. No. 68 |
| I-74 | methylamine·HCl | Co. No. 69 |

| Intermediate | Reagent | Final Compound |
|---|---|---|
| I-74 | 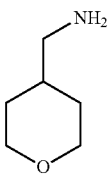 | 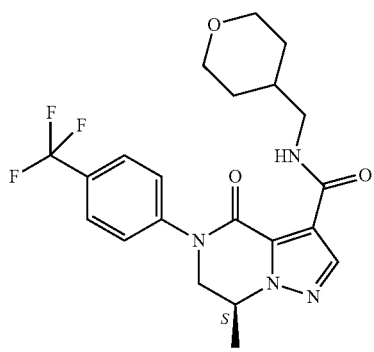<br>Co. No. 70 |
| I-74 | 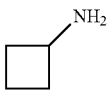 | 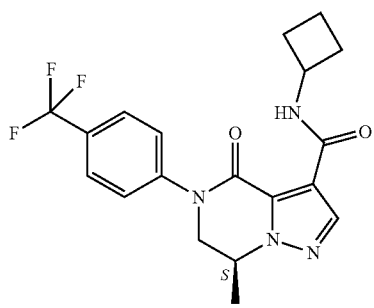<br>Co. No. 71 |
| I-74 | 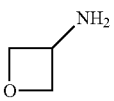 | 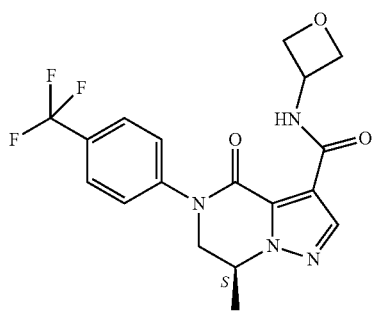<br>Co. No. 72 |
| I-74 | NH₄Cl | 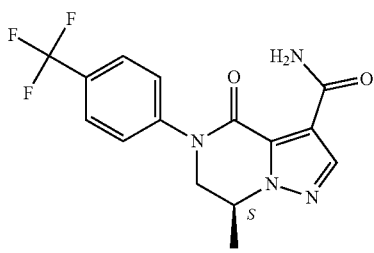<br>I-69 and Co. No. 73 |

-continued
| Intermediate | Reagent | Final Compound |
|---|---|---|
| I-76 | NH$_4$Cl | 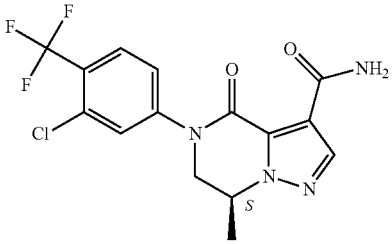<br>Co. No. 74 |
| I-77 | NH$_4$Cl | 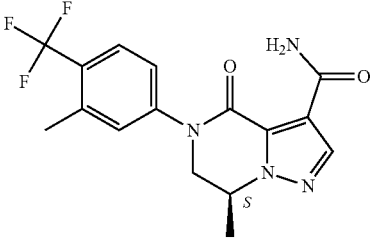<br>Co. No. 75 |
| I-78 | NH$_4$Cl | 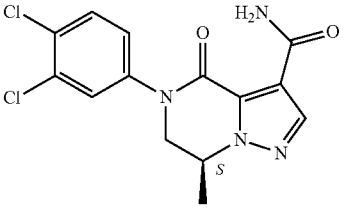<br>Co. No. 76 |
| I-80 | NH$_4$Cl | 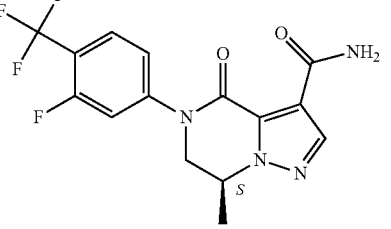<br>Co. No. 77 |
| I-80 | 5-fluoro-2-aminopyridine | 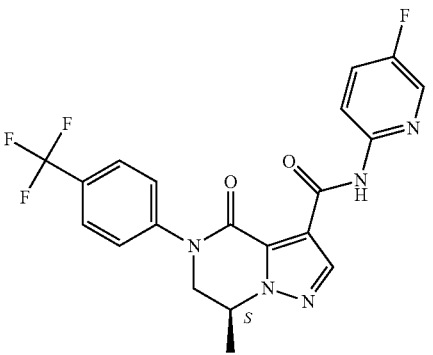<br>Co. No. 78 |

-continued

| Intermediate | Reagent | Final Compound |
|---|---|---|
| I-81 | I-93 | Co. No. 79 |
| I-82 | NH₄Cl | Co. No. 80 |
| I-82 | (5-fluoropyridin-2-amine) | Co. No. 81 |
| I-83 | NH₄Cl | Co. No. 82 |
| I-81 | NH₄Cl | Co. No. 166 |

| Intermediate | Reagent | Final Compound |
|---|---|---|
| I-96 | NH₄Cl | 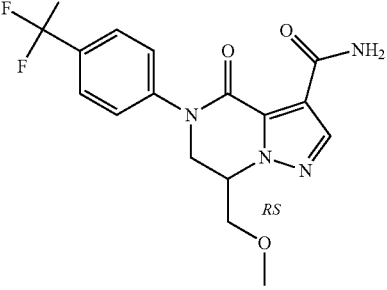<br>I97 |

Example 4 (E-4)

(7S)-5-(5-Chloro-6-methoxy-2-pyridyl)-7-methyl-4-oxo-N-phenyl-6,7-dihydropyrazolo[1,5-a]pyrazine-3-carboxamide (Co. No. 83)

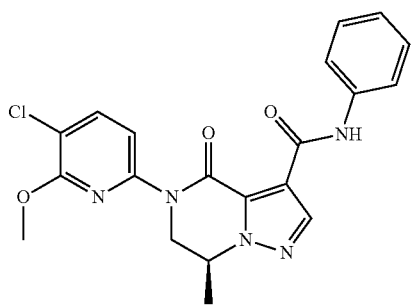 [SMILES: COc1nc(N2C[C@H](C)n3ncc(C(=O)Nc4ccccc4)c3C2=O)ccc1Cl]

A mixture of intermediate I-79 (100 mg, 0.297 mmol), aniline (30 µL, 0.327 mmol), HATU (147 mg, 0.386 mmol) and DIPEA (119 µL, 0.683 mmol) in DMF (1.5 mL) was stirred at 80° C. for 16 h. The mixture was diluted in DCM and washed with sat. sol. NaHCO₃. The organic layer was separated, dried (Na₂SO₄), filtered and the solvents evaporated in vacuo. The crude product was triturated with MeOH to yield final compound Co. No. 83 (75 mg, 61%) as a pale yellow solid. $^1$H NMR (400 MHz, CDCl₃) δ ppm 1.73 (d, J=6.7 Hz, 3H) 4.03 (s, 3H) 4.34 (dd, J=13.6, 7.2 Hz, 1H) 4.56 (dd, J=13.6, 4.2 Hz, 1H) 4.79 (quind, J=6.7, 6.7, 6.7, 6.7, 4.3 Hz, 1H) 7.05-7.15 (m, 1H) 7.29-7.40 (m, 2H) 7.61 (d, J=8.1 Hz, 1H) 7.74-7.77 (m, 2H) 7.77 (d, J=8.3 Hz, 1H) 8.34 (s, 1H) 11.91 (br. s, 1H).

Following a procedure analogous to that described for E-4, the following compounds were also synthesized:

| Intermediate | Reagent | Final Compound |
|---|---|---|
| I-74 | 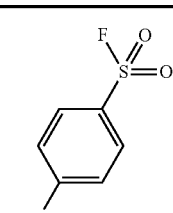 | 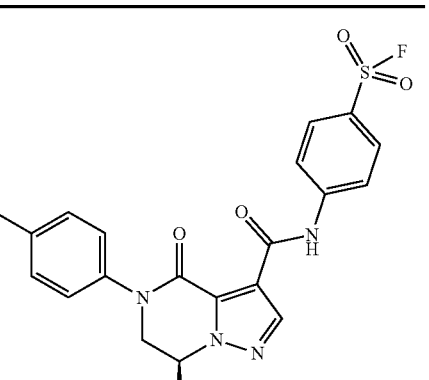<br>Co. No. 167 |

Example 5 (E-5)

(7S)-5-[4-chloro-3-(difluoromethoxy)phenyl]-7-methyl-N-(2-methyl-4-pyridyl)-4-oxo-6,7-dihydropyrazolo[1,5-a]pyrazine-3-carboxamide (Co. No. 84)

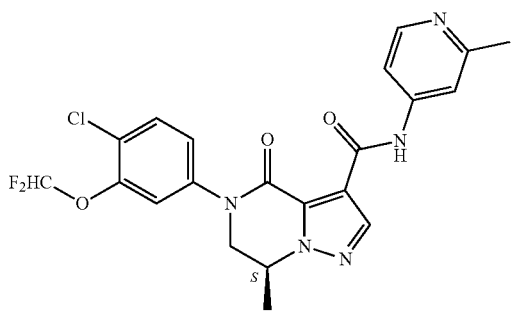

Et$_3$N (275 µL, 1.983 mmol) was added to a mixture of intermediate I-49 (290 mg, 0.693 mmol), Pd(OAc)$_2$ (3 mg, 0.013 mmol), dppf (14 mg, 0.026 mmol), 4-amino-2-methylpyridine (71 mg, 0.661 mmol) in 1,4-dioxane (30 mL) was stirred under CO atmosphere (6 atm) at 90° C. for 18 h. The mixture was diluted with sat. sol. NaHCO$_3$ and extracted with EtOAc. The organic layer was separated, dried (MgSO$_4$), filtered and the solvents evaporated in vacuo. The crude product was purified by flash column chromatography (silica; EtOAc in heptane 0/100 to 90/10). The desired fractions were collected and the solvents concentrated in vacuo. The product was triturated with pentane to yield final compound Co. No. 84 (135 mg, 45%). $^1$H NMR (300 MHz, CDCl$_3$) δ ppm 1.76 (d, J=6.5 Hz, 3H) 2.53 (s, 3H) 3.99 (dd, J=12.9, 7.6 Hz, 1H) 4.26 (dd, J=12.9, 4.3 Hz, 1H) 4.75-4.90 (m, 1H) 6.63 (t, J=72.7 Hz, 1H) 7.22-7.29 (m, 1H) 7.33 (s, 1H) 7.47 (d, J=5.6 Hz, 1H) 7.50 (s, 1H) 7.61 (d, J=8.7 Hz, 1H) 8.32 (s, 1H) 8.36 (d, J=5.6 Hz, 1H) 12.08 (br. s., 1H).

Following a procedure analogous to that described for E-5, the following compounds were also synthesized:

| Intermediate | Reagent | Final Compound |
|---|---|---|
| I-39 | 4-amino-2-methylpyridine | Co. No. 85 |
| I-40 | 4-amino-2-methylpyridine | Co. No. 86 |
| I-41 | 4-amino-2-methylpyridine | Co. No. 87 |

-continued
| Intermediate | Reagent | Final Compound |
|---|---|---|
| I-43 | | |
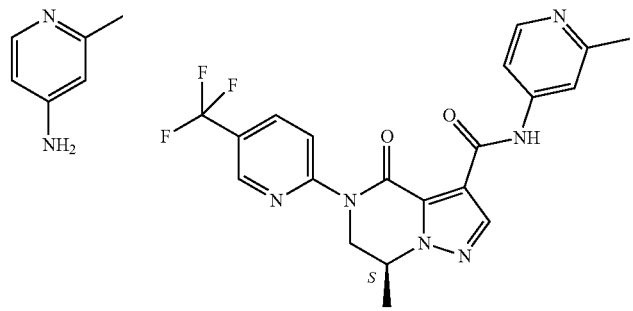
Co. No. 88
| I-44 | | |
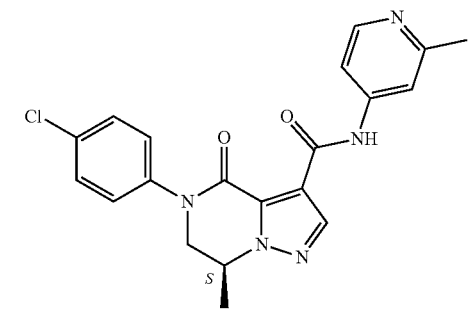
Co. No. 89
| I-45 | | |
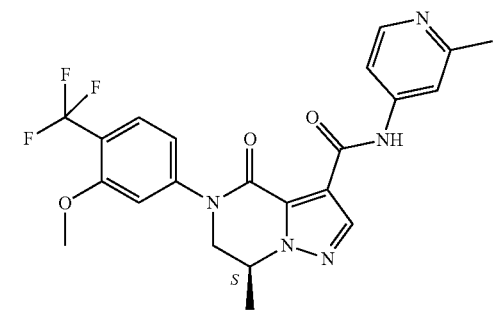
Co. No. 90
| I-46 | | |
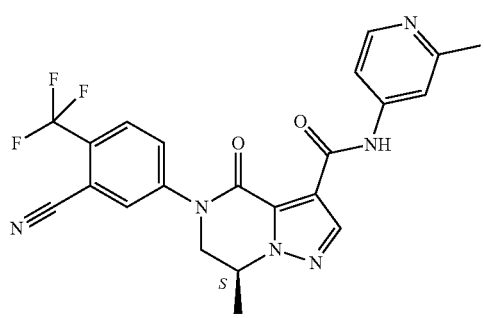
Co. No. 91

-continued
| Intermediate | Reagent | Final Compound |
|---|---|---|
| I-53 | 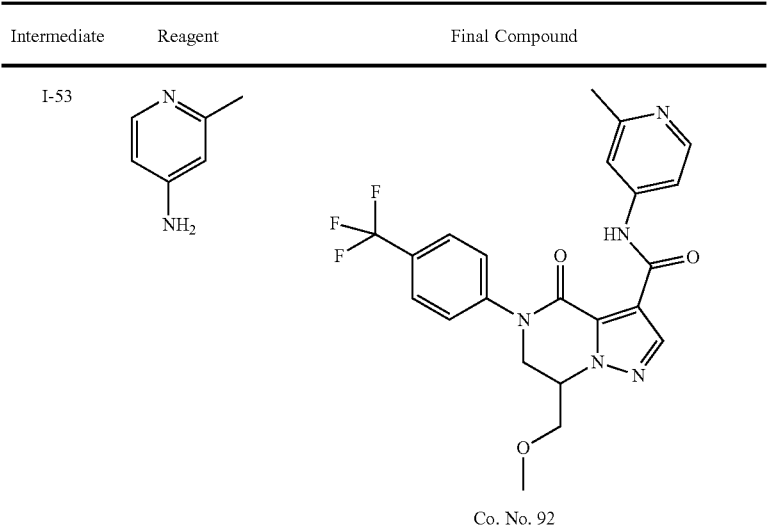 | |
Co. No. 92
Then separated by chiral SFC
(Stationary phase: CHIRALPAK IC
5 μm 250 x 30 mm, Mobile phase:
60% CO$_2$, 40% EtOH(0.3%
iPrNH$_2$)) - yielding 126 mg Co. No.
92 and 135 mg Co. No. 93
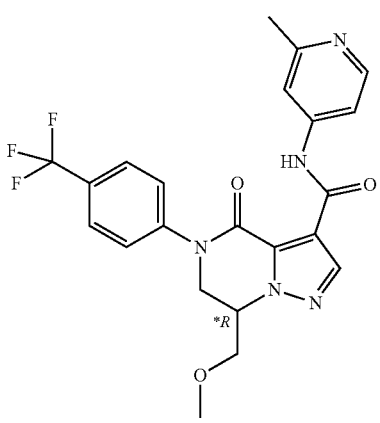
Co. No. 93

-continued
| Intermediate | Reagent | Final Compound |
|---|---|---|
| | | 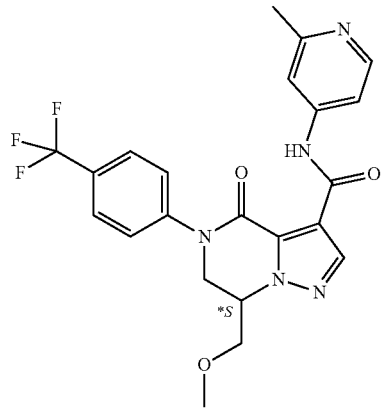
Co. No. 94 |
| I-47 | 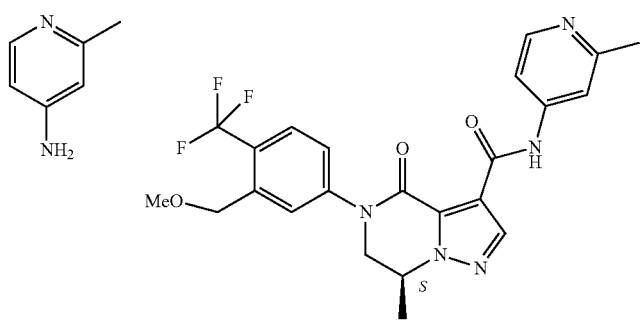
Co. No. 95
and also obtained |
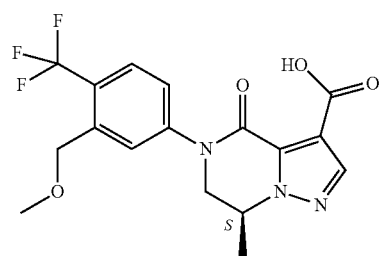
I-85

-continued
| Intermediate | Reagent | Final Compound |
|---|---|---|
| I-48 | 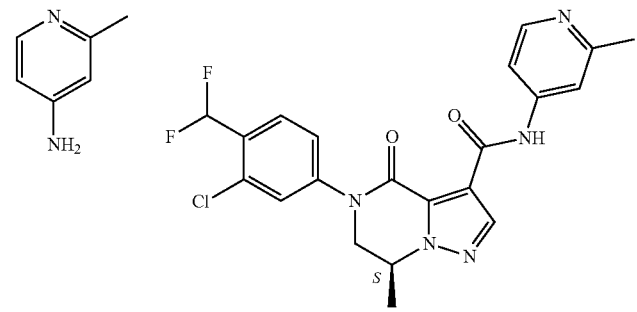 | 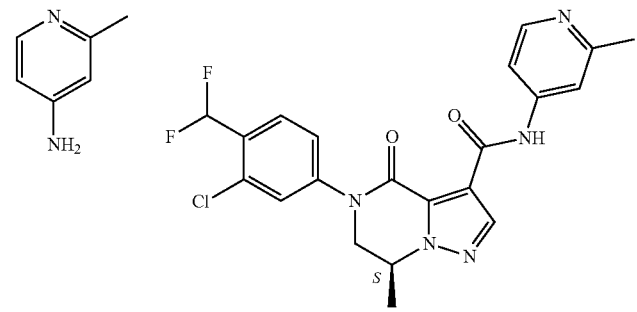
Co. No. 96 |
| I-55 | 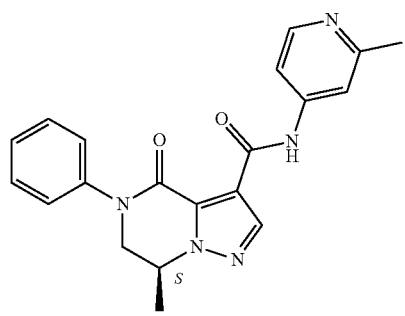 | 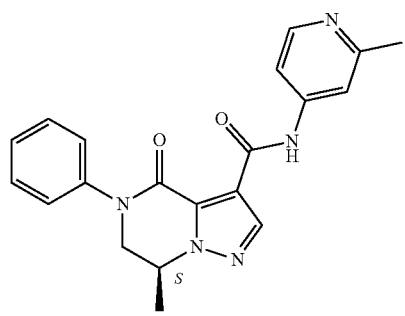
Co. No. 97
and also obtained
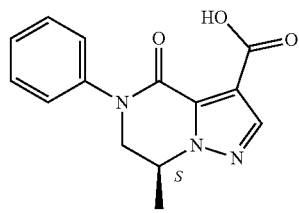
I-84 |

Example 6 (E-6)

(7S)-5-(3,4-Dichlorophenyl)-N-(5-fluoro-2-pyridyl)-7-methyl-4-oxo-6,7-dihydropyrazolo[1,5-a]pyrazine-3-carboxamide (Co. No. 98)

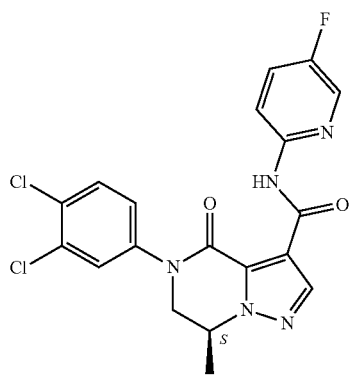

Pd$_2$(dba)$_3$ (24 mg, 0.026 mmol) and 2-bromo-5-fluoro-pyridine (78 mg, 0.442 mmol) were added to a stirred mixture of compound Co. No. 76 (150 mg, 0.442 mmol), Xantphos (26 mg, 0.044 mmol), K$_3$PO$_4$ (281 mg, 1.326 mmol) in THF (6 mL) in a sealed tube and under nitrogen. The mixture was stirred at 90° C. for 4 h. The mixture was treated with sat. sol. NaHCO$_3$ and extracted with EtOAc. The organic layer was separated, dried (Na$_2$SO$_4$), filtered and the solvents concentrated in vacuo. The crude product was purified by flash column chromatography (silica; EtOAc in Heptane 0/100 to 50/50). The desired fractions were collected and the solvents concentrated in vacuo to yield final compound Co. No. 98 (178 mg, 93%) as a cream solid after triturating with DIPE. $^1$H NMR (400 MHz, CDCl$_3$) δ ppm 1.75 (d, J=6.7 Hz, 3H) 3.97 (dd, J=12.9, 7.4 Hz, 1H) 4.26 (dd, J=12.8, 4.3 Hz, 1H) 4.82 (quind, J=6.7, 4.4 Hz, 1H) 7.26 (dd, J=8.6, 2.5 Hz, 1H) 7.43 (ddd, J=9.1, 7.8, 3.0 Hz, 1H) 7.51 (d, J=2.5 Hz, 1H) 7.55 (d, J=8.6 Hz, 1H) 8.19 (d, J=3.0 Hz, 1H) 8.34 (s, 1H) 8.38 (dd, J=9.2, 3.9 Hz, 1H) 12.39 (br. s, 1H).

Following a procedure analogous to that described for E-6, the following compounds were also synthesized:

| Intermediate | Reagent | Final Compound |
|---|---|---|
| I-69 | Br-pyrimidine-2-methyl | Co. No. 99 |
| I-69 | 2-chloropyrazine | Co. No. 100 |

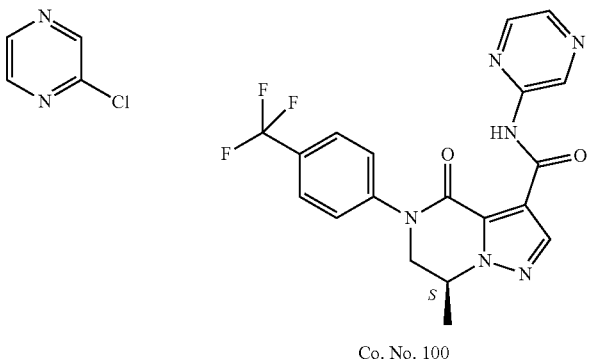

-continued

| Intermediate | Reagent | Final Compound |
|---|---|---|
| I-69 | 4-bromo-2,6-dimethylpyridine | Co. No. 101 |
| I-69 | 2-bromo-5-methoxypyridine | Co. No. 102 |
| I-69 | 2-bromopyrimidine | Co. No. 103 |
| I-69 | 2-bromo-5-fluoropyridine | Co. No. 104 |

-continued
| Intermediate | Reagent | Final Compound |
|---|---|---|
| I-69 | 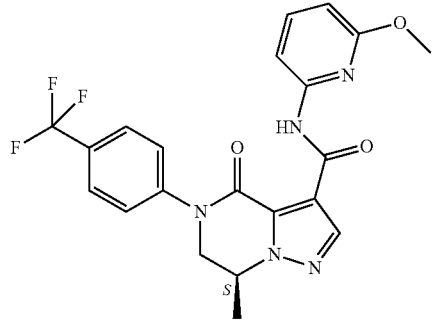 | 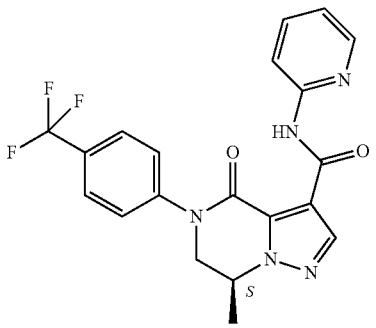<br>Co. No. 105 |
| I-69 | | Co. No. 9 |
| Co. No. 74 | 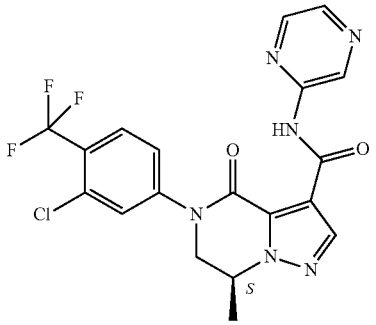 | Co. No. 106 |
| Co. No. 74 | 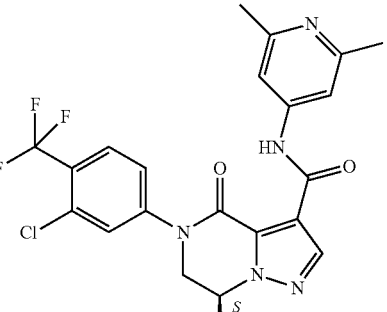 | Co. No. 107 |

-continued
| Intermediate | Reagent | Final Compound |
|---|---|---|
| Co. No. 74 | 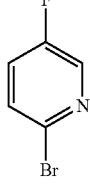 | 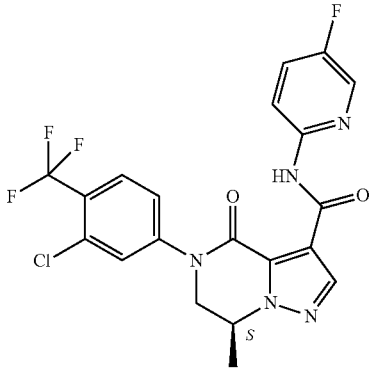<br>Co. No. 108 |
| Co. No. 74 | 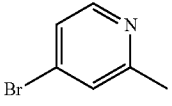 | 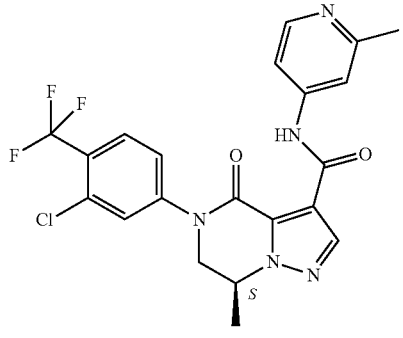<br>Co. No. 109 |
| Co. No. 75 | 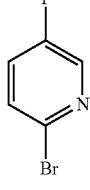 | 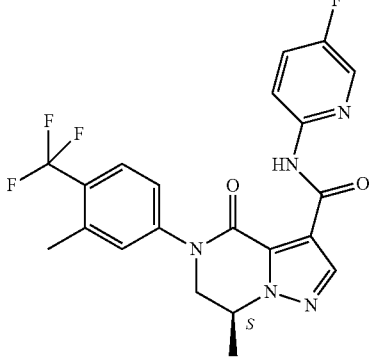<br>Co. No. 110 |
| Co. No. 75 | 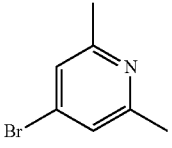 | 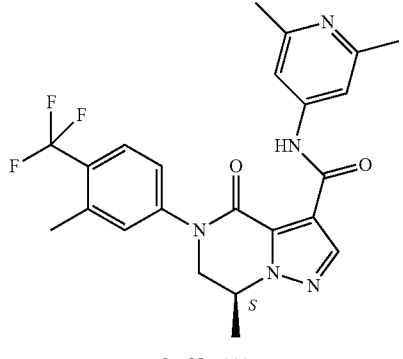<br>Co. No. 111 |

| Intermediate | Reagent | Final Compound |
|---|---|---|
| Co. No. 75 | 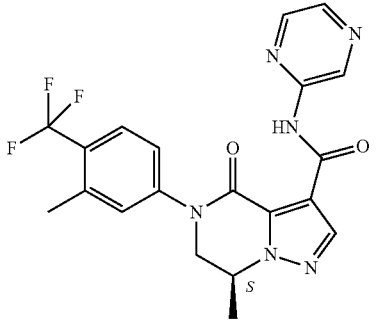 | 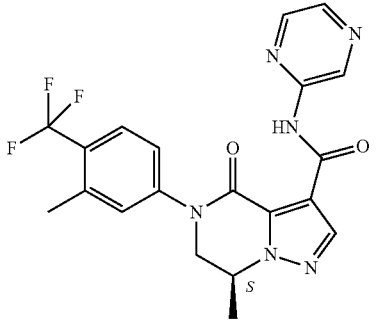<br>Co. No. 112 |
| Co. No. 77 | 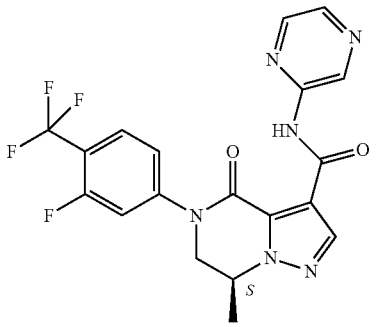 | 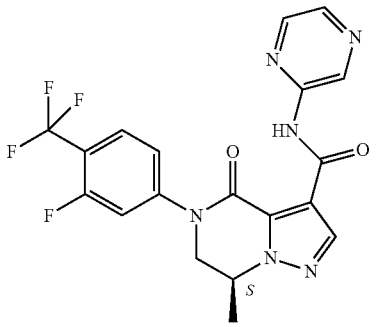<br>Co. No. 113 |
| Co. No. 77 | 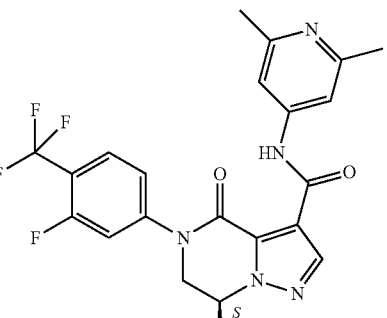 | 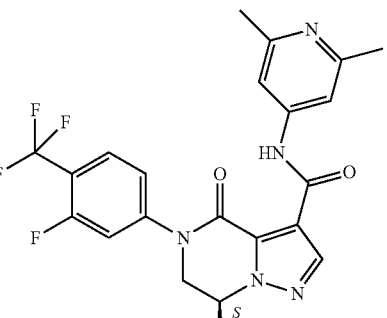<br>Co. No. 114 |
| Co. No. 80 | 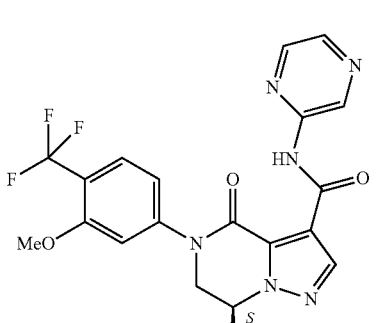 | 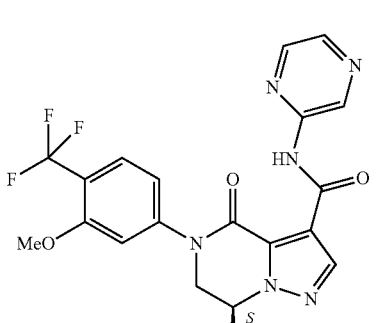<br>Co. No. 115 |

-continued
| Intermediate | Reagent | Final Compound |
|---|---|---|
| Co. No. 76 | 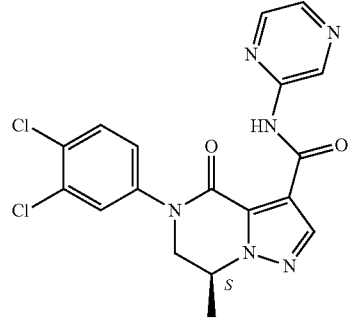 | 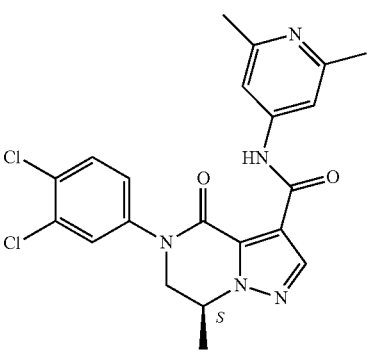<br>Co. No. 116 |
| Co. No. 76 | 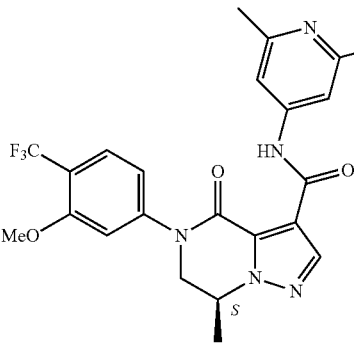 | 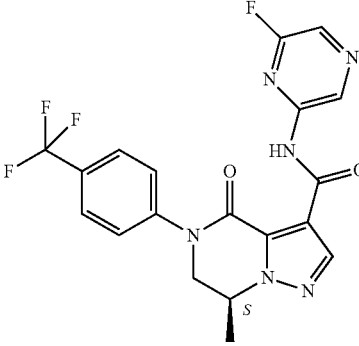<br>Co. No. 118 |
| Co. No. 80 | | Co. No. 143 |
| I-69 | | Co. No. 145 |

-continued
| Intermediate | Reagent | Final Compound |
|---|---|---|
| I-69 (Procedure A) | 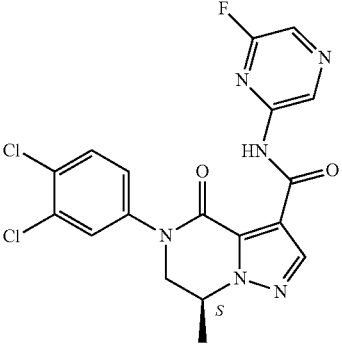 | 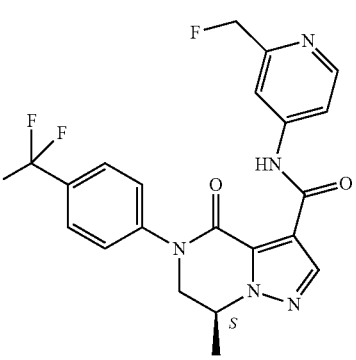<br>Co. No. 146 |
| I-69 | | Co. No. 151 |
| Co. No. 166 | 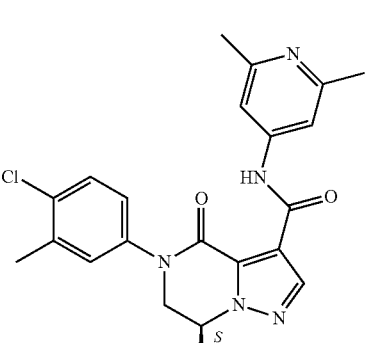 | Co. No. 160 |
| Co. No. 166 | 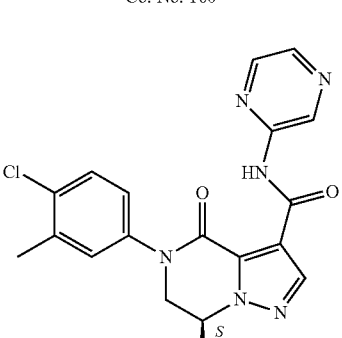 | Co. No. 161 |

| Intermediate | Reagent | Final Compound |
|---|---|---|
| Co. No. 82 | | 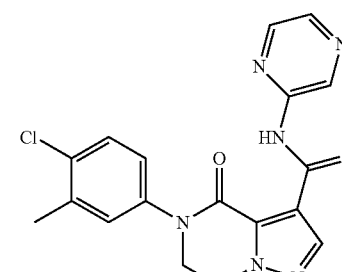 Co. No. 162 |
| | | 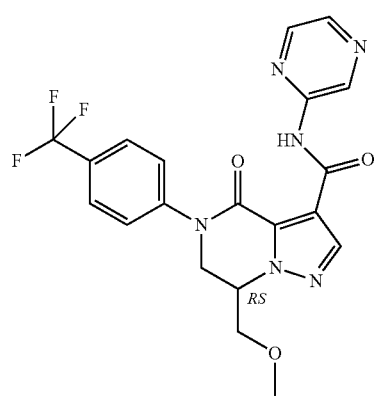 Co. No. 163<br>Co. No. 163 was purified by Chiral SFC (Stationary phase: CHIRALCEL OD-H 5 μm 250x20 mm, Mobile phase: 70% CO2, 30% iPrOH) to yield Co. No. 154 and Co. No. 155. |
| I-97 | | 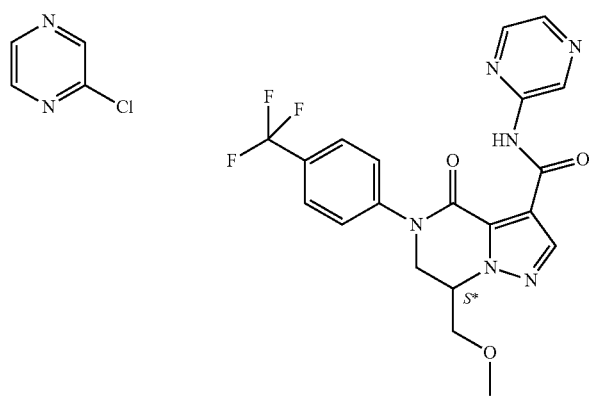 Co. No. 154 |

| Intermediate | Reagent | Final Compound |
|---|---|---|
| | | 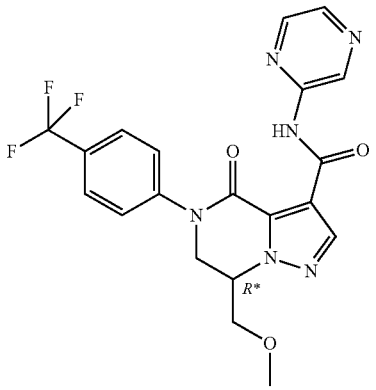<br>Co. No. 155 |

Example 7 (E-7) (7S)—N-(3-Methoxyphenyl)-5-[6-methoxy-5-(trifluoromethyl)-2-pyridyl]-7-methyl-4-oxo-6,7-dihydropyrazolo[1,5-a]pyrazine-3-carboxamide (Co. No. 119)

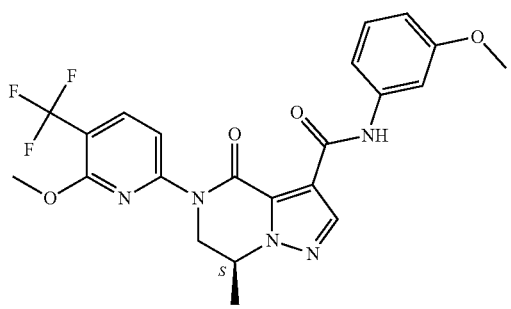

Trimethylaluminium (2M in Heptane, 293 µL, 0.585 mmol) was added to a stirred solution of m-anisidine (66 µL, 0.585 mmol) in THF (2.5 mL) at 0° C. under nitrogen atmosphere. To this solution intermediate I-72 (150 mg, 0.390 mmol) in THF (2 mL) was added at 0° C. The mixture was stirred at 150° C. for 5 min under microwave irradiation. The excess of trimethylaluminium was quenched with HCl 1N and diluted with DCM. The organic layer was separated, dried ($Na_2SO_4$), filtered and the solvent evaporated in vacuo. The crude product was purified by flash column chromatography (silica, EtOAc in DCM 0/100 to 20/80). The desired fractions were collected and the solvent evaporated in vacuo to yield final compound Co. No. 119 (92 mg, 49%). as a white solid. $^1$H NMR (400 MHz, $CDCl_3$) δ ppm 1.74 (d, J=6.7 Hz, 3H) 3.84 (s, 3H) 4.06 (s, 3H) 4.40 (dd, J=13.8, 7.3 Hz, 1H) 4.63 (dd, J=13.6, 4.2 Hz, 1H) 4.79 (quind, J=6.7, 4.3 Hz, 1H) 6.67 (ddd, J=7.6, 2.5, 1.6 Hz, 1H) 7.14-7.26 (m, 2H) 7.58 (t, J=2.1 Hz, 1H) 7.78 (d, J=8.1 Hz, 1H) 8.00 (d, J=8.6 Hz, 1H) 8.34 (s, 1H) 11.82 (br. s, 1H).

Following a procedure analogous to that described for E-7, the following compounds were also synthesized:

| Intermediate | Reagent | Final Compound |
|---|---|---|
| I-72 | | |
| | | 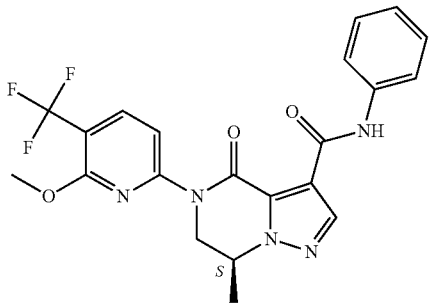<br>Co. No. 120 |

-continued

| Intermediate | Reagent | Final Compound |
|---|---|---|
| I-72 | 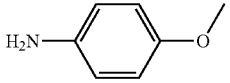 | 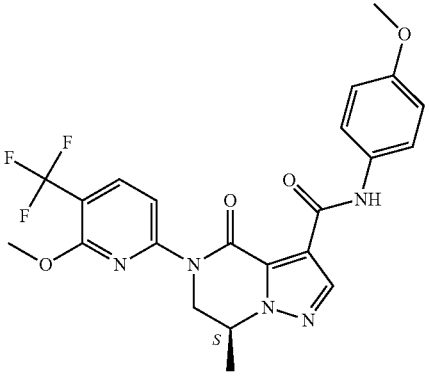
Co. No. 121 |
| I-72 | 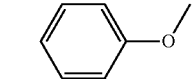 | 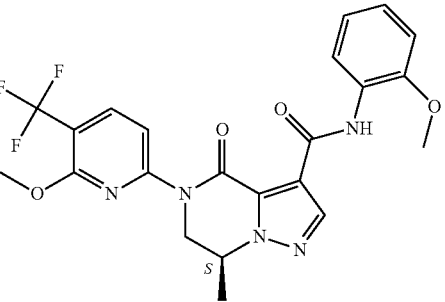
Co. No. 122 |

Example 8 (E-8)

(7S)-7-Methyl-5-[3-methyl-4-(trifluoromethyl)phenyl]-4-oxo-N-(3-pyridyl)-6,7-dihydropyrazolo[1,5-a]pyrazine-3-carboxamide (Co. No. 36)

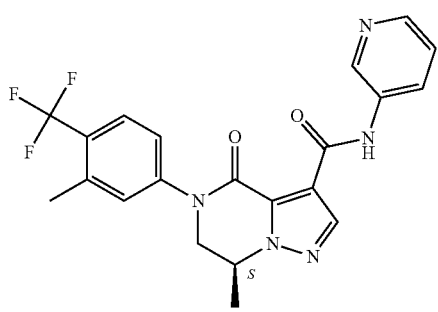

Isopropylmagnesium chloride lithium chloride complex solution (1.3 M in THF, 12.6 mL, 16.33 mmol) was added to a stirred solution of 3-aminopyridine (1.15 g, 12.25 mmol) in THF (49.5 mL) under nitrogen. The mixture was stirred at rt for 1 h. The resulting solution was added to a stirred solution of intermediate I-59 (3 g, 8.16 mmol) in THF (49.5 mL) and the mixture was stirred at 65° C. for 16 h. More isopropylmagnesium chloride lithium chloride complex solution (1.3 M in THF, 6.3 mL, 8.16 mmol) was added and the mixture was stirred at 70° C. for 1 h. Water was added and the mixture was extracted with EtOAc. The organic layer was separated, dried (Na$_2$SO$_4$), filtered and the solvents concentrated in vacuo. The crude product was purified by flash column chromatography (silica; EtOAc in DCM 0/100 to 100/0). The desired fractions were collected and the solvents concentrated in vacuo. The crude product was purified by flash column chromatography (silica; MeOH in DCM 0/100 to 10/90). The desired fractions were collected and the solvents concentrated in vacuo. The residue was triturated with DIPE to yield final compound Co. No. 36 (2 g, 57%) as a white solid. $^1$H NMR (500 MHz, CDCl$_3$) δ ppm 1.76 (d, J=6.4 Hz, 3H) 2.58 (s, 3H) 4.01 (dd, J=13.0, 7.2 Hz, 1H) 4.30 (dd, J=13.0, 4.3 Hz, 1H) 4.79-4.87 (m, 1H) 7.25 (dd, J=8.1, 4.6 Hz, 1H) 7.32 (d, J=8.4 Hz, 1H) 7.35 (s, 1H) 7.77 (d, J=8.4 Hz, 1H) 8.24 (dt, J=8.4, 1.4 Hz, 1H) 8.32 (dd, J=4.6, 0.9 Hz, 1H) 8.34 (s, 1H) 8.81 (d, J=2.3 Hz, 1H) 12.05 (br. s., 1H).

Following a procedure analogous to that described for E-8, the following compounds were also synthesized:

| Intermediate | Reagent | Final Compound |
| --- | --- | --- |
| I-61 | 5-fluoro-2-aminopyridine | Co. No. 104 |
| I-61 | 6-methyl-2-aminopyrazine | Co. No. 123 |
| I-61 | I-93 | Co. No. 124 |
| I-61 | 3-amino-5-methylpyridine | Co. No. 8 |

-continued
| Intermediate | Reagent | Final Compound |
|---|---|---|
| I-59 | I-93 | 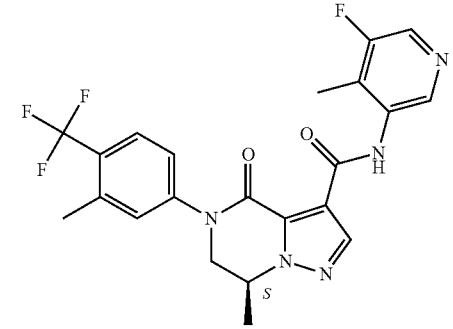<br>Co. No. 125 |
| I-58 | 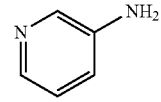 | 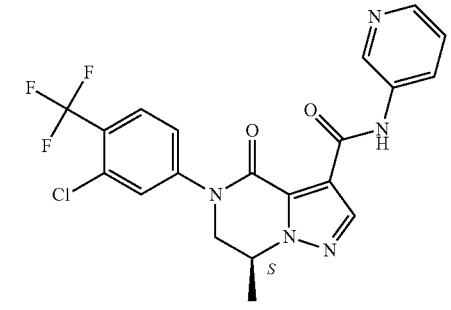<br>Co. No. 47 |
| I-58 | I-94 | 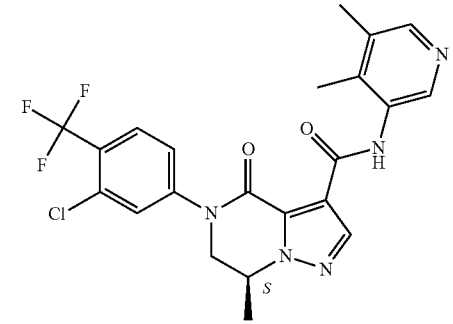<br>Co. No. 126 |
| I-58 | I-95 | 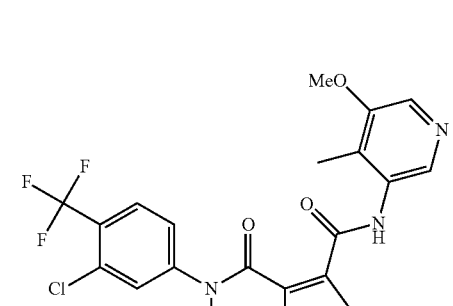<br>Co. No. 127 |

-continued

| Intermediate | Reagent | Final Compound |
|---|---|---|
| I-58 | H₂N-(3-methylisoxazol-5-yl) | Co. No. 128 |
| I-64 | 3-aminopyridine | Co. No. 41 |
| I-64 | I-93 | Co. No. 129 |
| I-60 | I-93 | Co. No. 130 |

| Intermediate | Reagent | Final Compound |
|---|---|---|
| I-57 | I-93 | 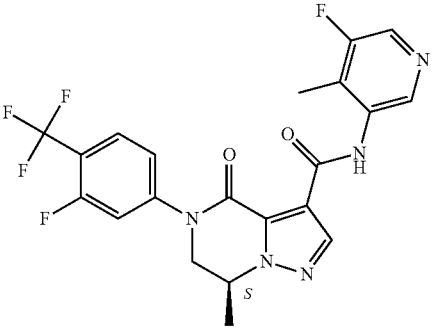<br>Co. No. 131 |
| I-94 | 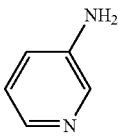 | 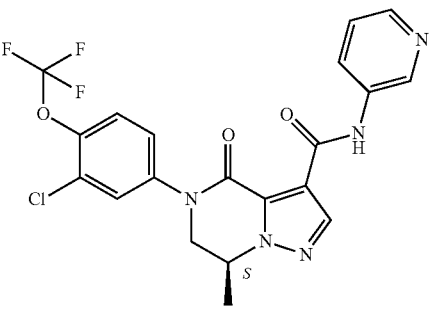<br>Co. No. 152 |

Example 9 (E-9)

(7S)—N-(5-Fluoro-4-methyl-3-pyridyl)-7-methyl-4-oxo-5-[4-(trifluoromethyl)phenyl]-6,7-dihydropyrazolo[1,5-a]pyrazine-3-carboxamide (Co. No. 124)

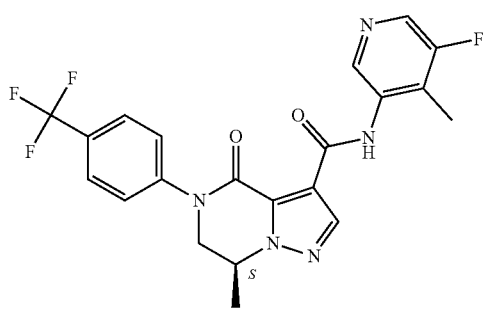

Lithium bis(trimethylsilyl)amide (1M in THF, 0.653 mL, 0.653 mmol) was added to a stirred solution of intermediate I-93 (75 mg, 0.598 mmol) in THF (5 mL) at 0° C. The mixture was stirred at 0° C. for 30 min, then was cooled to −10° C. and intermediate I-61 (200 mg, 0.544 mmol) in THF (3 mL) was added. The mixture was stirred at −10° C. for 1 h. The mixture was diluted with water and extracted with EtOAc. The organic layer was separated, dried (Na₂SO₄), filtered and the solvents concentrated in vacuo. The crude product was purified by flash column chromatography (silica; EtOAc in DCM 0/100 to 20/80 and then 7N solution of ammonia in MeOH in DCM 10/90). The desired fractions were collected and the solvents concentrated in vacuo. The residue was triturated with DIPE to yield final compound Co. No. 124 (76 mg, 31%). as a pale salmon solid. ¹H NMR (500 MHz, CDCl₃) δ ppm 1.78 (d, J=6.4 Hz, 3H) 2.25 (d, J=1.4 Hz, 3H) 4.05 (dd, J=12.9, 7.4 Hz, 1H) 4.34 (dd, J=12.9, 4.2 Hz, 1H) 4.82-4.90 (m, 1H) 7.53 (d, J=8.4 Hz, 2H) 7.78 (d, J=8.4 Hz, 2H) 8.22 (s, 1H) 8.36 (s, 1H) 8.94 (s, 1H) 11.56 (br. s, 1H).

Following a procedure analogous to that described for E-9, the following compounds were also synthesized:

| Intermediate | Reagent | Final Compound |
|---|---|---|
| I-61 | F-[5-fluoropyridin-2-amine] | Co. No. 104 |
| I-61 | I-95 | Co. No. 132 |

Example 10 (E-10)

(7S)-5-[3-chloro-4-(trifluoromethyl)phenyl]-N-(5-fluoro-4-methyl-3-pyridyl)-7-methyl-4-oxo-6,7-dihydropyrazolo[1,5-a]pyrazine-3-carboxamide (Co. No. 133)

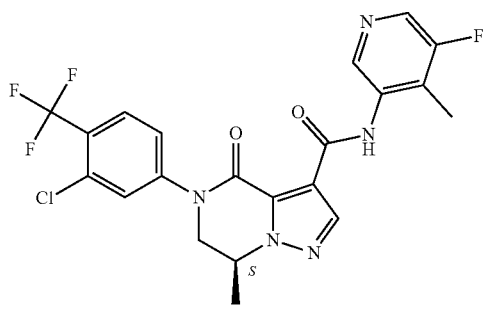

Intermediate I-93 (56 mg, 0.448 mmol) in THF (1 mL) was added to a stirred solution of ethylmagnesium bromide (1M in THF, 0.448 mL, 0.448 mmol) under nitrogen. The mixture was stirred at rt for 1 h. The resulting solution was added to a stirred solution of intermediate I-58 (150 mg, 0.373 mmol) in THF (0.84 mL) and the mixture was stirred at rt for 18 h. Water was added and the mixture was extracted with EtOAc. The organic layer was separated, dried ($Na_2SO_4$), filtered and the solvents concentrated in vacuo. The crude product was purified by flash column chromatography (silica; EtOAc in DCM 0/100 to 20/80 and then 7N solution of ammonia in MeOH in DCM 10/90). The desired fractions were collected and the solvents concentrated in vacuo. The residue was triturated with DIPE to yield final compound Co. No. 133 (65 mg, 36%). as an off-white solid. $^1$H NMR (500 MHz, $CDCl_3$) δ ppm 1.78 (d, J=6.4 Hz, 3H) 2.27 (d, J=1.4 Hz, 3H) 4.05 (dd, J=12.7, 7.5 Hz, 1H) 4.32 (dd, J=12.9, 4.2 Hz, 1H) 4.86 (quind, J=6.9, 4.3 Hz, 1H) 7.43 (dd, J=8.4, 1.4 Hz, 1H) 7.59 (d, J=2.0 Hz, 1H) 7.83 (d, J=8.4 Hz, 1H) 8.23 (br. s., 1H) 8.37 (s, 1H) 8.95 (br. s., 1H) 11.44 (s, 1H).

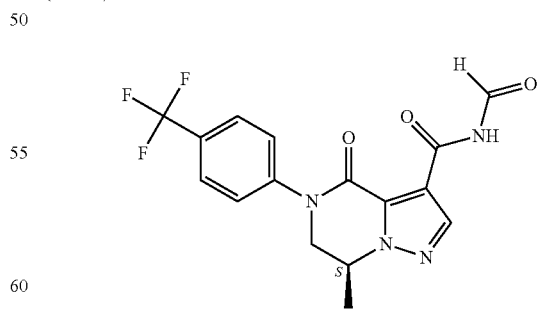

Example 11 (E-11)

To a solution of intermediate I-69 or Co. No. 73 (30 mg, 0.0887 mmol) in DCM (0.568 mL) was added N,N-dimeth-

Example 12 (E-12)

(7S)-7-Methyl-N-(2-methylpyridine-4-carbonyl)-4-oxo-5-[4-(trifluoromethyl)phenyl]-6,7-dihydropyrazolo[1,5-a]pyrazine-3-carboxamide (Co. No. 135)

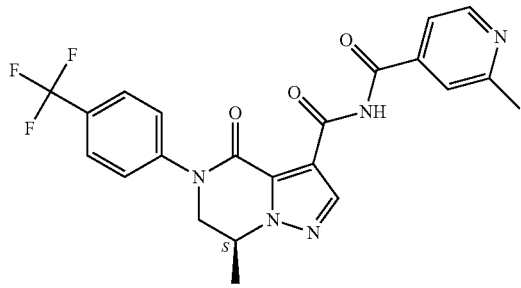

2-Methyl-4-pyridinecarbonyl chloride (80 mg, 0.514 mmol) was added to a stirred mixture of intermediate I-69 (174 mg, 0.514 mmol) in pyridine (414 μL) under nitrogen. The mixture was stirred at 50° C. for 2 h. The solvent was concentrated in vacuo and the crude product was purified by flash column chromatography (silica, 7N solution of ammonia in MeOH in DCM 0:100 to 4:96) to yield a colorless oil which was further purified by RP HPLC (Stationary phase: C18 XBridge 30×100 mm 5 μm; mobile phase: gradient from 67% 0.1% NH$_4$CO$_3$H/NH$_4$OH pH 9 solution in water, 33% MeCN to 50% 0.1% NH$_4$CO$_3$H/NH$_4$OH pH 9 solution in water, 50% MeCN) to yield final compound Co. No. 135 (11 mg, 5%). $^1$H NMR (500 MHz, CDCl$_3$) δ ppm 1.77 (d, J=6.6 Hz, 3H) 2.55 (s, 3H) 4.09 (dd, J=13.0, 7.5 Hz, 1H) 4.36 (dd, J=13.0, 4.3 Hz, 1H) 4.86 (quind, J=6.9, 4.2 Hz, 1H) 7.56 (br. d, J=8.4 Hz, 2H) 7.60 (dd, J=5.2, 1.2 Hz, 1H) 7.71 (br. s, 1H) 7.79 (br. d, J=8.4 Hz, 2H) 8.36 (s, 1H) 8.60 (d, J=5.2 Hz, 1H) 13.12 (br. s, 1H).

ylformamide dimethyl acetal (15.315 μL, 0.115 mmol) at rt. Then 5 Å molecular sieves (50 mg) were added and the mixture was stirred for at 70° C. for 40 min under microwave irradiation. The mixture was filtered through a pad of diatomaceous earth and washed with DCM. The solvent was removed in vacuo and the residue was purified by flash column chromatography (EtOAc in DCM gradient from 0:100 to 50:50). The desired fractions were collected and concentrated in vacuo to yield final compound Co. No. 134 (19 mg, 58.49%) as a white solid. $^1$H NMR (500 MHz, CDCl$_3$) δ ppm 1.77 (d, J=6.6 Hz, 3H) 4.04 (dd, J=13.0, 7.5 Hz, 1H) 4.32 (dd, J=13.0, 4.3 Hz, 1H) 4.85 (quind, J=6.8, 4.3 Hz, 1H) 7.52 (d, J=8.4 Hz, 2H) 7.76 (d, J=8.4 Hz, 2H) 8.34 (s, 1H) 9.34 (d, J=9.2 Hz, 1H) 12.35 (br. d, J=8.4 Hz, 1H).

Example 13 (E-13)

(7S)—N-[(6-Amino-3-pyridyl)methyl]-7-methyl-4-oxo-5-[4-(trifluoromethyl)phenyl]-6,7-dihydropyrazolo[1,5-a]pyrazine-3-carboxamide (Co. No. 136)

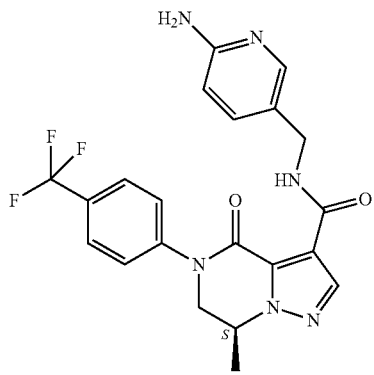

A mixture of intermediate I-89 (75 mg, 0.144 mmol), hydroxylamine hydrochloride (50 mg, 0.72 mmol) and Et$_3$N (20 μL, 0.144 mmol) in EtOH (2 mL) and water (1 mL) was stirred at reflux for 20 h. Hydroxylamine hydrochloride (50 mg, 0.72 mmol) and Et$_3$N (20 μL, 0.144 mmol) were added. The mixture was refluxed for an additional 12 h then cooled. The cooled solution was quenched with HCl, washed with Et$_2$O, and the pH was adjusted to 9-10 with 2 M NaOH. The resulting mixture was extracted several times with DCM. The combined organic phases were dried (MgSO$_4$) and the solvent was evaporated in vacuo. The crude product was purified by flash column chromatography (silica; DCM-MeOH 9/1 in DCM 5/100 to 70/30). The desired fractions were collected and the solvents evaporated in vacuo. The product was triturated with DIPE to yield final compound Co. No. 136 (43 mg, 66%) as a white solid. $^1$H NMR (300 MHz, CDCl$_3$) δ ppm 1.65 (d, J=6.6 Hz, 3H) 3.89 (dd, J=12.8, 7.1 Hz, 1H) 4.20 (dd, J=12.8, 4.3 Hz, 1H) 4.31 (br. s., 2H) 4.36 (d, J=5.8 Hz, 2H) 4.65-4.78 (m, 1H) 6.36 (d, J=8.4 Hz, 1H) 7.37-7.45 (m, 3H) 7.68 (br. d, J=8.4 Hz, 2H) 7.94 (d, J=1.5 Hz, 1H) 8.20 (s, 1H) 9.99 (br. t, J=5.1, 5.1 Hz, 1H).

Example 14 (E-14)

(7S)—N-(cyclobutanecarbonyl)-7-methyl-4-oxo-5-[4-(trifluoromethyl)phenyl]-6,7-dihydropyrazolo[1,5-a]pyrazine-3-carboxamide (Co. No. 137)

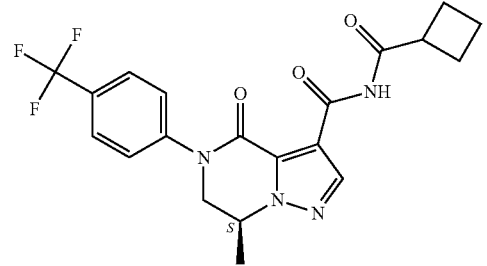

Dess-Martin periodinane (167 mg, 0.394 mmol) was added to a stirred solution of intermediate I-90 (100 mg, 0.246 mmol) in fluorobenzene (2.5 mL) and DMSO (100 µL) at rt. The resulting mixture was stirred in a sealed tube at 85° C. for 1 h. The mixture was allowed to reach rt and then it was partitioned between EtOAc and an aq. sol. of $Na_2S_2O_3$. The organic layer was dried ($MgSO_4$), filtered and the solvent concentrated in vacuo. The crude product was purified by flash column chromatography (silica; MeOH in DCM 10:90). The desired fractions were collected and the solvents concentrated in vacuo to give a residue, which was further purified by RP HPLC (Stationary phase: C18 XBridge 30×100 mm 5 µm; mobile phase: gradient from 54% 0.1% $NH_4CO_3H/NH_4OH$ pH 9 solution in Water, 46% MeCN to 64% 0.1% $NH_4CO_3H/NH_4OH$ pH 9 solution in water, 36% MeCN), to yield final compound Co. No. 137 (45 mg, 43%). $^1$H NMR (500 MHz, $CDCl_3$) δ ppm 1.74 (d, J=6.4 Hz, 3H) 1.81-1.90 (m, 1H) 1.91-2.02 (m, 1H) 2.18-2.28 (m, 2H) 2.29-2.39 (m, 2H) 3.66 (quin, J=8.5 Hz, 1H) 4.02 (dd, J=13.0, 7.2 Hz, 1H) 4.31 (dd, J=13.0, 4.3 Hz, 1H) 4.78-4.86 (m, 1H) 7.52 (d, J=8.1 Hz, 2H) 7.76 (d, J=8.4 Hz, 2H) 8.28 (s, 1H) 12.18 (br. s., 1H).

Following a procedure analogous to that described for E-14, the following compounds were also synthesized:

| Intermediate | Final compound |
|---|---|
| I-91 | 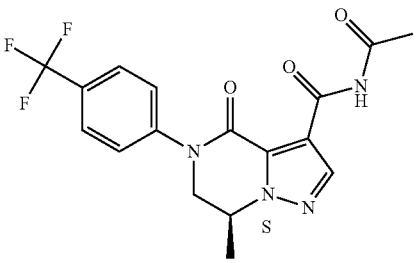 Co. No. 138 |

Example 15 (E-15)

(7S)—N-[5-(hydroxymethyl)pyridin-3-yl]-7-methyl-4-oxo-5-[4-(trifluoromethyl) phenyl]-4,5,6,7-tetrahydropyrazolo[1,5-a]pyrazine-3-carboxamide (Co. No. 148)

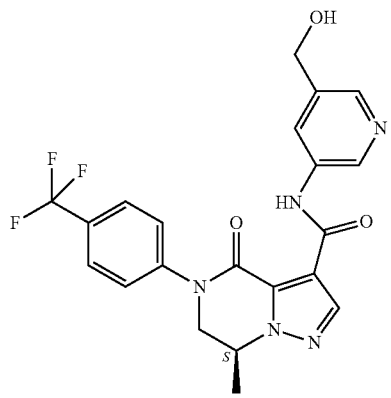

Copper(I) iodide (45.6 mg, 0.240 mmol) was added to a stirred suspension of intermediate I-69 (202.6 mg, 0.599 mmol), heteroaryl-halide [37669-64-0] (201.7 mg, 0.898 mmol) and $K_3PO_4$ (381.4 mg, 1.797 mmol) in 1,4-dioxane (8.1 mL). The mixture was nitrogen flushed for a few minutes and then (+/−)-trans-1,2-cyclohexanediamine (28.8 µL, 0.240 mmol) and TEA (0.250 mL, 1.797 mmol) were added. The mixture was stirred under nitrogen in a sealed tube at 100° C. for 18 h. Then more TEA (0.250 mL, 1.797 mmol) was added and stirred at 100° C. for 4 h. Then the mixture was diluted with $NH_4OH$/brine and extracted with EtOAc. The organic layer was separated and evaporated in vacuo. The crude product was purified by flash column chromatography (silica; EtOAc in DCM 0/100 to 100/0). The desired fractions were collected and the solvents concentrated in vacuo. The crude product was triturated with DIPE, filtered and dried to yield final compound Co. No. 148 (122 mg, 46%) as a white solid.

Following a procedure analogous to that described for E-15, the following compounds were also synthesized:

| Intermediate | Reagent | Final compound |
|---|---|---|
| I-69 | | |

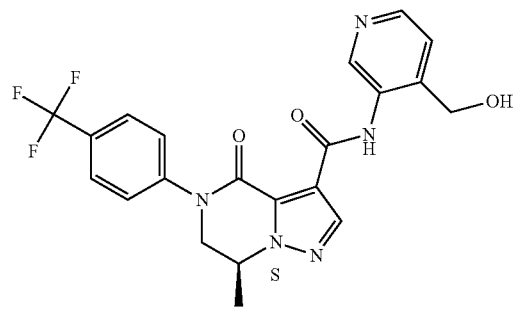

Co. No. 147

-continued

| Intermediate | Reagent | Final compound |
|---|---|---|
| I-69 | 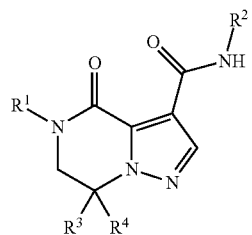 | Co. No. 149 |
| I-69 | | Co. No. 150 |

Table 1 below lists additional compounds of Formula (I).

TABLE 1

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | $R^1$ | $R^2$ | $>CR^3R^4$ | Salt Form |
|---|---|---|---|---|
| 1 | 4-CF$_3$-phenyl | 3-pyridyl | >CH(CH$_3$) (S) | |
| 2 | 4-CF$_3$-phenyl | 3-(methylsulfonyl)phenyl | >CH(CH$_3$) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 57 | 4-CF₃-phenyl | phenyl | >CH(CH₃) (S) | |
| 3 | 4-CF₃-phenyl | pyridin-4-yl | >CH(CH₃) (S) | |
| 85 | 3,4-dichlorophenyl | 2-methylpyridin-4-yl | >CH(CH₃) (S) | |
| 86 | 3-methyl-4-CF₃-phenyl | 2-methylpyridin-4-yl | >CH(CH₃) (S) | |
| 19 | 4-CF₃-phenyl | 2-aminopyridin-5-yl | >CH(CH₃) (S) | |
| 4 | 4-CF₃-phenyl | 3-fluoropyridin-4-yl | >CH(CH₃) (S) | |
| 56 | 3,4-dichlorophenyl | 6-fluoropyridazin-3-yl | >CH(CH₃) (S) | |
| 5 | 4-CF₃-phenyl | 2-methylpyridin-4-yl | >CH(CH₃) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | $R^1$ | $R^2$ | $>CR^3R^4$ | Salt Form |
|---|---|---|---|---|
| 6 | 4-$CF_3$-phenyl | 4-($CH_3SO_2$)-phenyl | $>CH(CH_3)$ (S) | |
| 87 | 3-F-4-$CF_3$-phenyl | 2-methylpyridin-4-yl | $>CH(CH_3)$ (S) | |
| 23 | 3-F-4-$CF_3$-phenyl | 4-methylpyridin-3-yl | $>CH(CH_3)$ (S) | |
| 120 | 3-$CF_3$-6-methoxypyridin-2-yl | phenyl | $>CH(CH_3)$ (S) | |
| 7 | 4-$CF_3$-phenyl | 4-F-phenyl | $>CH(CH_3)$ (S) | |
| 144 | 4-$CF_3$-phenyl | 5-methoxypyridin-3-yl | $>CH(CH_3)$ (S) | |
| 55 | 4-$CF_3$-phenyl | 6-F-pyridin-3-yl | $>CH(CH_3)$ (S) | |
| 8 | 4-$CF_3$-phenyl | 5-methylpyridin-3-yl | $>CH(CH_3)$ (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | R$^1$ | R$^2$ | >CR$^3$R$^4$ | Salt Form |
|---|---|---|---|---|
| 119 | 3-CF$_3$-2-methoxy-pyridin-6-yl | 3-methoxyphenyl | >CH(CH$_3$) (S) | |
| 88 | 5-CF$_3$-pyridin-2-yl | 2-methylpyridin-4-yl | >CH(CH$_3$) (S) | |
| 121 | 3-CF$_3$-2-methoxy-pyridin-6-yl | 4-methoxyphenyl | >CH(CH$_3$) (S) | |
| 89 | 4-chlorophenyl | 2-methylpyridin-4-yl | >CH(CH$_3$) (S) | |
| 9 | 4-CF$_3$-phenyl | pyridin-2-yl | >CH(CH$_3$) (S) | |
| 83 | 3-chloro-2-methoxy-pyridin-6-yl | phenyl | >CH(CH$_3$) (S) | |
| 90 | 2-CF$_3$-5-methoxy-phenyl | 6-methylpyridazin-3-yl | >CH(CH$_3$) (S) | |
| 58 | 4-CF$_3$-phenyl | cyclobutylmethyl | >CH(CH$_3$) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

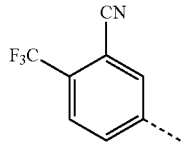

| Co. No. | $R^1$ | $R^2$ | $>CR^3R^4$ | Salt Form |
|---|---|---|---|---|
| 91 | 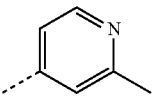 | 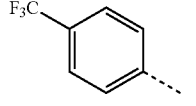 | $>CH(CH_3)$ (S) | |
| 10 | 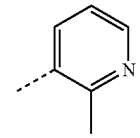 | 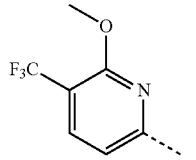 | $>CH(CH_3)$ (S) | |
| 122 | 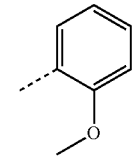 | 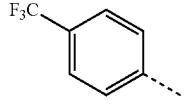 | $>CH(CH_3)$ (S) | |
| 59 | 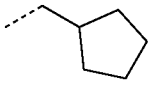 | 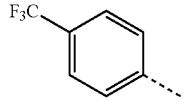 | $>CH(CH_3)$ (S) | |
| 60 | 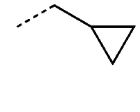 | 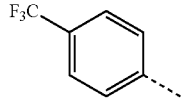 | $>CH(CH_3)$ (S) | |
| 99 | 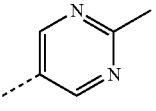 | 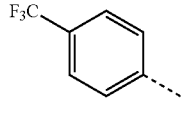 | $>CH(CH_3)$ (S) | |
| 134 | 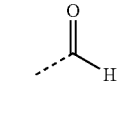 | 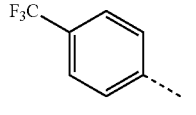 | $>CH(CH_3)$ (S) | |
| 61 | 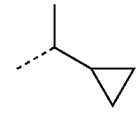 | 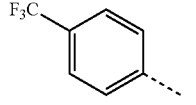 | $>CH(CH_3)$ (S) | |
| 62 | 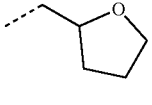 | | $>CH(CH_3)$ (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 63 | F₃C-phenyl | 2-methylpyridin-4-yl-methyl | >CH(CH₃) (S) | |
| 64 | F₃C-phenyl | tetrahydrofuran-3-yl-methyl | >CH(CH₃) (S) | |
| 65 | F₃C-phenyl | cyclohexyl-methyl | >CH(CH₃) (S) | |
| 66 | F₃C-phenyl | tetrahydropyran-4-yl-methyl | >CH(CH₃) (S) | |
| 67 | F₃C-phenyl | benzyl | >CH(CH₃) (S) | |
| 68 | F₃C-phenyl | tert-butyl | >CH(CH₃) (S) | |
| 69 | F₃C-phenyl | —CH₃ | >CH(CH₃) (S) | |
| 135 | F₃C-phenyl | (2-methylpyridin-4-yl)carbonyl | >CH(CH₃) (S) | |
| 70 | F₃C-phenyl | tetrahydropyran-4-yl-methyl | >CH(CH₃) (S) | |
| 136 | F₃C-phenyl | (6-aminopyridin-3-yl)methyl | >CH(CH₃) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | $R^1$ | $R^2$ | $>CR^3R^4$ | Salt Form |
|---|---|---|---|---|
| 20 | 2-F, 4-(F$_3$C)-phenyl (F$_3$C para, F ortho) | pyridin-2-yl | >CH(CH$_3$) (S) | |
| 100 | 4-(F$_3$C)-phenyl | pyrazin-2-yl | >CH(CH$_3$) (S) | |
| 101 | 4-(F$_3$C)-phenyl | 2,6-dimethylpyridin-4-yl | >CH(CH$_3$) (S) | |
| 46 | 2-Cl, 4-(F$_3$C)-phenyl | pyridin-2-yl | >CH(CH$_3$) (S) | |
| 94 | 4-(F$_3$C)-phenyl | 2-methylpyridin-4-yl | >CH(CH$_2$OCH$_3$) (*S) | |
| 93 | 4-(F$_3$C)-phenyl | 2-methylpyridin-4-yl | >CH(CH$_2$OCH$_3$) (*R) | |
| 71 | 4-(F$_3$C)-phenyl | cyclobutyl | >CH(CH$_3$) (S) | |
| 72 | 4-(F$_3$C)-phenyl | oxetan-3-yl | >CH(CH$_3$) (S) | |
| 35 | 2-methyl, 4-(F$_3$C)-phenyl | pyridin-2-yl | >CH(CH$_3$) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 25 | 3,4-diCl-phenyl | 2-pyridyl | >CH(CH$_3$) (S) | |
| 11 | 4-CF$_3$-phenyl | 3-methoxy-2-pyridyl | >CH(CH$_3$) (S) | |
| 12<br>12a | 4-CF$_3$-phenyl | 3-F-2-pyridyl | >CH(CH$_3$) (S) | •HCl |
| 92 | 4-CF$_3$-phenyl | 2-methyl-4-pyridyl | >CH(CH$_2$OCH$_3$) | |
| 31 | 2-methoxymethyl-4-CF$_3$-phenyl | 2-pyridyl | >CH(CH$_3$) (S) | |
| 102 | 4-CF$_3$-phenyl | 5-methoxy-2-pyridyl | >CH(CH$_3$) (S) | |
| 103 | 4-CF$_3$-phenyl | 2-pyrimidinyl | >CH(CH$_3$) (S) | |
| 104 | 4-CF$_3$-phenyl | 5-F-2-pyridyl | >CH(CH$_3$) (S) | |
| 137 | 4-CF$_3$-phenyl | cyclobutyl | >CH(CH$_3$) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | $R^1$ | $R^2$ | $>CR^3R^4$ | Salt Form |
|---|---|---|---|---|
| 95 | 2-CF$_3$, 5-(CH$_2$OCH$_3$)-phenyl | 2-methylpyridin-4-yl | $>CH(CH_3)$ (S) | |
| 105 | 4-CF$_3$-phenyl | 6-methoxypyridin-3-yl | $>CH(CH_3)$ (S) | |
| 96 | 2-Cl, 4-CHF$_2$-phenyl | 2-methylpyridin-4-yl | $>CH(CH_3)$ (S) | |
| 13, 13a | 4-CF$_3$-phenyl | 5-fluoropyridin-3-yl | $>CH(CH_3)$ (S) | •HCl |
| 14 | 4-CF$_3$-phenyl | 4-methylpyridin-3-yl | $>CH(CH_3)$ (S) | |
| 138 | 4-CF$_3$-phenyl | acetyl | $>CH(CH_3)$ (S) | |
| 84 | 3-OCHF$_2$, 4-Cl-phenyl | 2-methylpyridin-4-yl | $>CH(CH_3)$ (S) | |
| 97 | phenyl | 2-methylpyridin-4-yl | $>CH(CH_3)$ (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 139 | F₃C-phenyl | oxazol-2-yl | >CH(CH₃) (S) | |
| 53 | 2-F-CH₂, 4-F₃C-phenyl | pyridin-3-yl | >CH(CH₃) (S) | |
| 54 | 2-F-CH₂, 4-F₃C-phenyl | 2-methylpyridin-4-yl | >CH(CH₃) (S) | |
| 140 | F₃C-phenyl | thiazol-2-yl | >CH(CH₃) (S) | |
| 141 | F₃C-phenyl | pyrimidin-5-yl | >CH(CH₃) (S) | |
| 17 | F₃C-phenyl | 6-methylpyridin-2-yl | >CH(CH₃) (S) | |
| 142 | F₃C-phenyl | 1H-imidazol-2-yl | >CH(CH₃) (S) | |
| 16 | F₃C-phenyl | 3-methoxypyridin-4-yl | >CH(CH₃) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

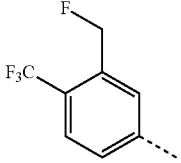

| Co. No. | $R^1$ | $R^2$ | >$CR^3R^4$ | Salt Form |
|---|---|---|---|---|
| 52 | 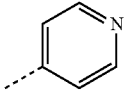 | 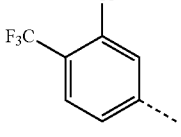 | >$CH(CH_3)$ (S) | |
| 47 | 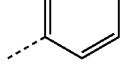 | 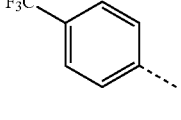 | >$CH(CH_3)$ (S) | |
| 15 | 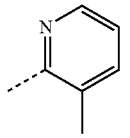 | 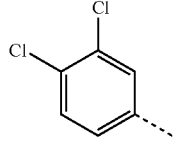 | >$CH(CH_3)$ (S) | |
| 98 | 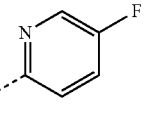 | 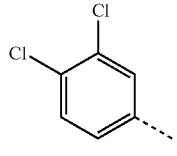 | >$CH(CH_3)$ (S) | |
| 26 | 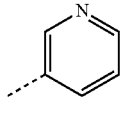 | 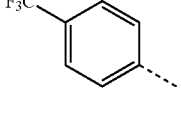 | >$CH(CH_3)$ (S) | |
| 18 | 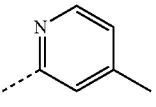 | 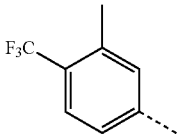 | >$CH(CH_3)$ (S) | |
| 37 | 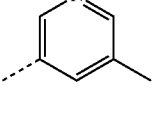 | 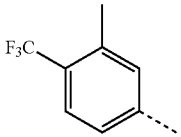 | >$CH(CH_3)$ (S) | |
| 36 | 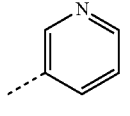 |  | >$CH(CH_3)$ (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 106 | 2-Cl-4-(F₃C)-phenyl | pyrazin-2-yl | >CH(CH₃) (S) | |
| 112 | 2-methyl-4-(F₃C)-phenyl | pyrazin-2-yl | >CH(CH₃) (S) | |
| 109 | 2-Cl-4-(F₃C)-phenyl | 2-methylpyridin-4-yl | >CH(CH₃) (S) | |
| 124 | 4-(F₃C)-phenyl | 3-fluoro-4-methylpyridin-5-yl | >CH(CH₃) (S) | |
| 133 | 2-Cl-4-(F₃C)-phenyl | 3-fluoro-4-methylpyridin-5-yl | >CH(CH₃) (S) | |
| 116 | 3,4-dichlorophenyl | pyrazin-2-yl | >CH(CH₃) (S) | |
| 118 | 3,4-dichlorophenyl | 2,6-dimethylpyridin-4-yl | >CH(CH₃) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | $R^1$ | $R^2$ | $>CR^3R^4$ | Salt Form |
|---|---|---|---|---|
| 107 | 2-Cl-4-(F$_3$C)-phenyl | 2,6-dimethylpyridin-4-yl | $>CH(CH_3)$ (S) | |
| 108 | 2-Cl-4-(F$_3$C)-phenyl | 5-fluoropyridin-2-yl | $>CH(CH_3)$ (S) | |
| 126 | 2-Cl-4-(F$_3$C)-phenyl | 4-methylpyridin-3-yl | $>CH(CH_3)$ (S) | |
| 132 | 4-(F$_3$C)-phenyl | 3-methoxy-4-methylpyridin-4-yl | $>CH(CH_3)$ (S) | |
| 127 | 2-Cl-4-(F$_3$C)-phenyl | 3-methoxy-4-methylpyridin-4-yl | $>CH(CH_3)$ (S) | |
| 111 | 2-methyl-4-(F$_3$C)-phenyl | 3,6-dimethylpyridazin-4-yl | $>CH(CH_3)$ (S) | |
| 110 | 2-methyl-4-(F$_3$C)-phenyl | 5-fluoropyridin-2-yl | $>CH(CH_3)$ (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | $R^1$ | $R^2$ | $>CR^3R^4$ | Salt Form |
|---|---|---|---|---|
| 28 | 3,4-diCl-phenyl | 5-methylpyridin-3-yl | $>CH(CH_3)$ (S) | |
| 39 | 4-CF$_3$-3-methyl-phenyl | 5-fluoropyridin-3-yl | $>CH(CH_3)$ (S) | |
| 40 | 4-CF$_3$-3-methyl-phenyl | 5-methoxypyridin-3-yl | $>CH(CH_3)$ (S) | |
| 41 | 4-Cl-phenyl | pyridin-3-yl | $>CH(CH_3)$ (S) | |
| 21 | 4-CF$_3$-3-F-phenyl | pyridin-3-yl | $>CH(CH_3)$ (S) | |
| 81 | 4-CF$_3$-3-methoxy-phenyl | 5-fluoropyridin-2-yl | $>CH(CH_3)$ (S) | |
| 29 | 3,4-diCl-phenyl | 5-methoxypyridin-3-yl | $>CH(CH_3)$ (S) | |
| 38 | 4-CF$_3$-3-methyl-phenyl | 4-methylpyridin-3-yl | $>CH(CH_3)$ (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

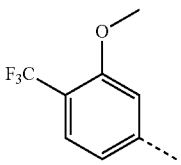

| Co. No. | $R^1$ | $R^2$ | >$CR^3R^4$ | Salt Form |
|---|---|---|---|---|
| 32 | 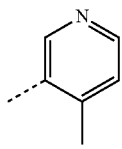 | 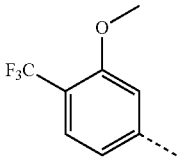 | >CH(CH$_3$) (S) | |
| 117 | 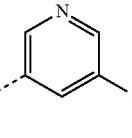 | 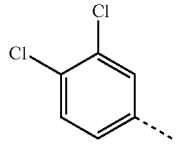 | >CH(CH$_3$) (S) | |
| 27 | 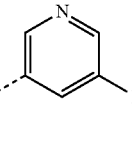 | 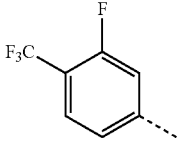 | >CH(CH$_3$) (S) | |
| 78 | 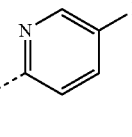 | 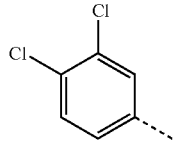 | >CH(CH$_3$) (S) | |
| 30 | 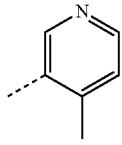 | 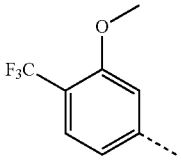 | >CH(CH$_3$) (S) | |
| 33 | 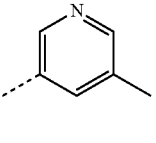 | 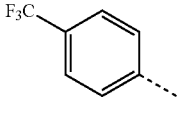 | >CH(CH$_3$) (S) | |
| 73 | F$_3$C—⟨phenyl⟩— | —H | >CH(CH$_3$) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | R$^1$ | R$^2$ | >CR$^3$R$^4$ | Salt Form |
|---|---|---|---|---|
| 75 | 2-CH$_3$-4-(F$_3$C)-phenyl | —H | >CH(CH$_3$) (S) | |
| 74 | 2-Cl-4-(F$_3$C)-phenyl | —H | >CH(CH$_3$) (S) | |
| 76 | 3-Cl-4-Cl-phenyl | —H | >CH(CH$_3$) (S) | |
| 80 | 2-OCH$_3$-4-(F$_3$C)-phenyl | —H | >CH(CH$_3$) (S) | |
| 77 | 2-F-4-(F$_3$C)-phenyl | —H | >CH(CH$_3$) (S) | |
| 82 | 4-Cl-phenyl | —H | >CH(CH$_3$) (S) | |
| 128 | 2-Cl-4-(F$_3$C)-phenyl | 3-methyl-isoxazol-5-yl | >CH(CH$_3$) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

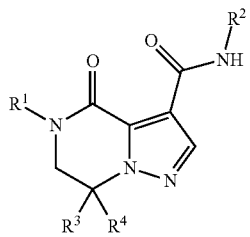

| Co. No. | $R^1$ | $R^2$ | $>CR^3R^4$ | Salt Form |
|---|---|---|---|---|
| 113 | 4-F$_3$C, 3-F phenyl | pyrazinyl | >CH(CH$_3$) (S) | |
| 34 | 4-F$_3$C, 3-OMe phenyl | 5-methoxypyridin-3-yl | >CH(CH$_3$) (S) | |
| 50 | 4-F$_3$C, 3-Cl phenyl | 5-fluoropyridin-3-yl | >CH(CH$_3$) (S) | |
| 115 | 4-F$_3$C, 3-OMe phenyl | pyrazinyl | >CH(CH$_3$) (S) | |
| 24 | 4-F$_3$C, 3-F phenyl | 5-fluoropyridin-3-yl | >CH(CH$_3$) (S) | |
| 130 | 3,4-diCl phenyl | 3-fluoro-4-methylpyridin-5-yl | >CH(CH$_3$) (S) | |
| 131 | 4-F$_3$C, 3-F phenyl | 3-fluoro-4-methylpyridin-5-yl | >CH(CH$_3$) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

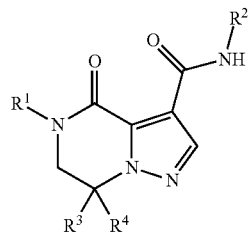

| Co. No. | R¹ | R² | >CR³R⁴ | Salt Form |
|---|---|---|---|---|
| 125 | 2-methyl-4-(trifluoromethyl)phenyl | 3-fluoropyridin-5-yl | >CH(CH₃) (S) | |
| 129 | 4-chlorophenyl | 3-fluoropyridin-5-yl | >CH(CH₃) (S) | |
| 79 | 4-chloro-3-methylphenyl | 3-fluoropyridin-5-yl | >CH(CH₃) (S) | |
| 143 | 2-methoxy-4-(trifluoromethyl)phenyl | 2,6-dimethylpyridin-4-yl | >CH(CH₃) (S) | |
| 22 | 2-fluoro-4-(trifluoromethyl)phenyl | 5-methylpyridin-3-yl | >CH(CH₃) (S) | |
| 51 | 2-chloro-4-(trifluoromethyl)phenyl | 5-methoxypyridin-3-yl | >CH(CH₃) (S) | |
| 123 | 4-(trifluoromethyl)phenyl | 6-methylpyrazin-2-yl | >CH(CH₃) (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

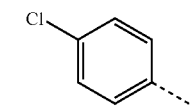

| Co. No. | $R^1$ | $R^2$ | $>CR^3R^4$ | Salt Form |
|---|---|---|---|---|
| 43 | 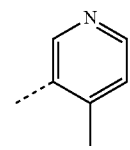 | 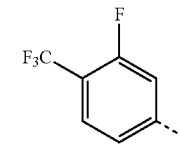 | $>CH(CH_3)$ (S) | |
| 114 | 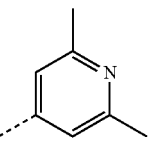 | 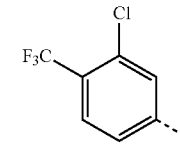 | $>CH(CH_3)$ (S) | |
| 49 | 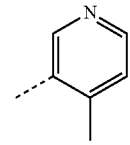 | 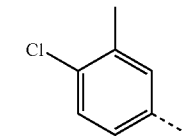 | $>CH(CH_3)$ (S) | •HCl |
| 44 | 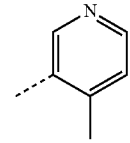 | 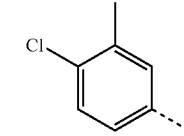 | $>CH(CH_3)$ (S) | |
| 45 | 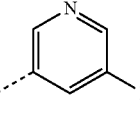 | 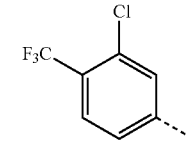 | $>CH(CH_3)$ (S) | |
| 48 | 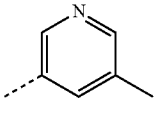 | 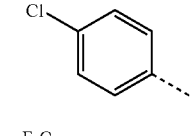 | $>CH(CH_3)$ (S) | |
| 42 | 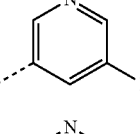 | 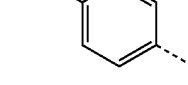 | $>CH(CH_3)$ (S) | |
| 145 | 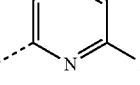 | | $>CH(CH_3)$ (S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 146 | 3,4-dichlorophenyl | 6-fluoropyrazin-2-yl | >CH(CH₃) (S) | |
| 147 | 4-(trifluoromethyl)phenyl | 4-(hydroxymethyl)pyridin-3-yl | >CH(CH₃) (S) | |
| 148 | 4-(trifluoromethyl)phenyl | 5-(hydroxymethyl)pyridin-3-yl | >CH(CH₃) (S) | |
| 149 | 4-(trifluoromethyl)phenyl | 2-(methoxymethyl)pyridin-4-yl | >CH(CH₃) (S) | |
| 150 | 4-(trifluoromethyl)phenyl | 2-(hydroxymethyl)pyridin-4-yl | >CH(CH₃) (S) | |
| 151 | 4-(trifluoromethyl)phenyl | 2-(fluoromethyl)pyridin-4-yl | >CH(CH₃) (S) | |
| 152 | 3-chloro-4-(trifluoromethoxy)phenyl | pyridin-3-yl | >CH(CH₃) (S) | |
| 153 | 4-(trifluoromethyl)phenyl | pyridin-3-yl | >CH₂ | |
| 154 | 4-(trifluoromethyl)phenyl | pyrazin-2-yl | >CH(CH₂OCH₃) (*S) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 155 | 4-CF₃-phenyl | pyrazin-2-yl | >CH(CH₂OCH₃) (*R) | |
| 156 | 3-Cl-4-CF₃-phenyl | pyridin-3-yl | >CH(CH₂OCH₃) (*S) | |
| 157 | 3-Cl-4-CF₃-phenyl | pyridin-3-yl | >CH(CH₂OCH₃) (*R) | |
| 158 | 4-CF₃-phenyl | pyridin-3-yl | >CH(CH₂OCH₃) (*S) | |
| 159 | 4-CF₃-phenyl | pyridin-3-yl | >CH(CH₂OCH₃) (*R) | |
| 160 | 4-Cl-3-methyl-phenyl | 2,6-dimethyl-pyridin-4-yl | >CH(CH₃) (S) | |
| 161 | 4-Cl-3-methyl-phenyl | pyrazin-2-yl | >CH(CH₃) (S) | |
| 162 | 4-Cl-phenyl | pyrazin-2-yl | >CH(CH₃) (S) | |
| 163 | 4-CF₃-phenyl | pyrazin-2-yl | >CH(CH₂OCH₃) (RS) | |

TABLE 1-continued

The following compounds were prepared following the methods exemplified in the Experimental Part (Ex. No.). Compounds exemplified and described in the experimental part are marked with an asterisk *. For some compounds the stereochemical configuration has been designated as *R or *S when the absolute stereochemistry is undetermined although the compound itself has been isolated as a single stereoisomer and is enantiomerically pure.

| Co. No. | $R^1$ | $R^2$ | $>CR^3R^4$ | Salt Form |
|---|---|---|---|---|
| 164 | 3-CF$_3$, 4-Cl-phenyl | pyridin-3-yl | $>CH(CH_2OCH_3)$ (RS) | |
| 165 | 4-CF$_3$-phenyl | pyridin-3-yl | $>CH(CH_2OCH_3)$ (RS) | |
| 166 | 4-Cl, 3-CH$_3$-phenyl | —H | $>CH(CH_3)$ (S) | |
| 167 | 4-CF$_3$-phenyl | 4-(fluorosulfonyl)phenyl | $>CH(CH_3)$ (S) | |

The values of salt stoichiometry or acid content in the compounds as provided herein, are those obtained experimentally and may vary when using different analytical methods. The content of hydrochloric acid reported herein was determined by $^1$H NMR integration and/or elemental analysis.

Analytical Part

Melting Points

Values are peak values, and are obtained with experimental uncertainties that are commonly associated with this analytical method.

DSC823e (A): For a number of compounds, melting points (m.p.) were determined with a DSC823e (Mettler-Toledo) apparatus. Melting points were measured with a temperature gradient of 10° C./minute. Maximum temperature was 300° C. Peak values were recorded.

Mettler Toledo MP50 (B): For a number of compounds, melting points were determined in open capillary tubes on a Mettler Toledo MP50. Melting points were measured with a temperature gradient of 10° C./minute. Maximum temperature was 300° C. The melting point data was read from a digital display and checked from a video recording system.

LCMS

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW) and/or exact mass monoisotopic molecular weight. Data acquisition was performed with appropriate software.

Compounds are described by their experimental retention times (Rt) and ions. If not specified differently in the table of data, the reported molecular ion corresponds to the [M+H]$^+$ (protonated molecule). For molecules with multiple isotopic patterns (Br, Cl), the reported value is the one obtained for the lowest isotope mass. All results were obtained with experimental uncertainties that are commonly associated with the method used.

TABLE 2

LC-MS Methods (Flow expressed in mL/min; column temperature (T) in ° C.; Run time in minutes).

| Method | Instrument | Column | Mobile phase | Gradient | Flow/Col T | Run time |
|---|---|---|---|---|---|---|
| 1 | Waters: Acquity ® UPLC ® - DAD/SQD | Waters: CSH ™ C18 (1.7 μm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | $\frac{1}{50}$ | 5 |
| 2 | Waters: Acquity ® IClass-DAD/ Xevo G2-S QTOF | Waters: CSH ™ C18 (1.7 μm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | $\frac{1}{50}$ | 5 |
| 3 | Waters: Acquity ® IClass UPLC ® - DAD/SQD | Waters: CSH ™ C18 (1.7 μm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | $\frac{1}{50}$ | 5 |
| 4 | Agilent 1100- DAD-MSD G1956A | YMC-pack ODS-AQ C18 (50 × 4.6 mm, 3 μm) | A: 0.1% HCOOH in $H_2O$ B: $CH_3CN$ | From 95% A to 5% A in 4.8 min, held for 1.0 min, to 95% A in 0.2 min. | $\frac{2.6}{35}$ | 6.0 |
| 5 | Waters: Acquity UPLC ® - DAD/Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | $\frac{0.343}{40}$ | 6.2 |
| 6 | Agilent 1290 Infinity DAD TOF-LC/MS G6224A | YMC-pack ODS-AQ C18 (50 × 4.6 mm, 3 μm) | A: 0.1% HCOOH in $H_2O$ B: $CH_3CN$ | ISET 2V10 Emulated Agilent Pump G1312A V1.0 From 94.51% A to 5% A in 4.8 min, held for 1.0 min, to 95% A in 0.2 min. | $\frac{2.6}{35}$ | 6.0 |
| 7 | Waters: Acquity ® UPLC ® - DAD/SQD | Waters: CSH ™ C18 (1.7 μm, 2.1 × 50 mm) | A: 95% $CH_3COONH_4$ 6.5 mM + 5% $CH_3CN$, B: $CH_3CN$ | From 95% A to 40% A in 1.2 min, to 5% A in 0.6 min, held for 0.2 min | $\frac{1}{50}$ | 2 |
| 8 | Agilent: HP1100-DAD, MSD G1956B | Agilent: Eclipse Plus C18 (3.5 μm, 2.1 × 30 mm) | A: 95% $CH_3COONH_4$ 6.5 mM + 5% $CH_3CN$, B: $CH_3CN$ | 95% A for 0.2 min, to 0% A in 2.8 min, held for 0.15 min, back to 95% | $\frac{1}{60}$ | 5 |

TABLE 2-continued

LC-MS Methods (Flow expressed in mL/min; column temperature (T) in ° C.; Run time in minutes).

| Method | Instrument | Column | Mobile phase | Gradient | Flow/Col T | Run time |
|---|---|---|---|---|---|---|
| 9 | Waters: Acquity ® IClass UPLC ®-DAD/ Xevo G2-S QTQF | Waters: CSH ™ C18 (1.7 μm, 2.1 × 50 mm) | A: 95% CH3COONH4 6.5 mM + 5% CH3CN, B: CH3CN | A in 0.15 min, held for 1.7 min From 95% A to 5% A in 4.6 min, held for 0.4 min | $\frac{1}{50}$ | 5 |

TABLE 3

Analytical data - melting point (M.p.) and LCMS: [M + H]$^+$ means the protonated mass of the free base of the compound, R$_t$ means retention time (in min), method refers to the method used for LCMS. For some compounds, exact mass was determined.

| Co. No. | M.p. (° C.) | [M + H]$^+$ | R$_t$ | LCMS Method |
|---|---|---|---|---|
| 1 | 167.35 (A) | 416.1333 (−0.1 mDa) | 2.15 | 2 |
| 2 | 217.7 (B) | 493 | 3.60 | 4 |
| 57 | n.d. | 415 | 4.02 | 6 |
| 3 | 160.2 (B) | 416 | 2.31 | 4 |
| 85 | 204.8 (B) | 431 | 2.40 | 6 |
| 86 | 121.8 (B) | 444 | 2.52 | 6 |
| 19 | 181.5 (B) | 431 | 2.25 | 6 |
| 4 | 189.0 (B) | 434 | 3.38 | 4 |
| 56 | 167.35 (A) | 416.1333 (−0.1 mDa) | 2.51 | 1 |
| 5 | 215.0 (B) | 430 | 2.34 | 6 |
| 6 | 198.2 (B) | 493 | 3.59 | 4 |
| 87 | 166.4 (B) | 448 | 2.38 | 4 |
| 23 | 225.0 (B) | 448 | 2.68 | 4 |
| 120 | 167.35 (A) | 416.1333 (−0.1 mDa) | 3.08 | 8 |
| 7 | 185.3 (B) | 433 | 3.90 | 6 |
| 144 | 197.8 (B) | 446 | 3.31 | 4 |
| 55 | n.d. | 434 | 2.37 | 1 |
| 8 | 167.35 (A) | 416.1333 (−0.1 mDa) | 2.31 | 2 |
| 119 | 194.51 (A) | 476 | 2.95 | 2 |
| 88 | 244.9 (B) | 431 | 2.27 | 4 |
| 121 | 212.39 (A) | 476 | 3 | 2 |
| 89 | 171.4 (B) | 396 | 2.20 | 6 |
| 9 | 246.7 (B) | 416 | 3.41 | 6 |
| 83 | 203.08 (A) | 412 | 2.7 | 1 |
| 90 | 176.4 (B) | 460 | 2.43 | 4 |
| 58 | 204.6 (B) | 407 | 3.66 | 6 |
| 91 | 224.9 (B) | 455 | 2.29 | 4 |
| 10 | 171.6 (B) | 430 | 2.53 | 4 |
| 122 | 192.95 (A) | 476 | 2.91 | 2 |
| 59 | 159.8 (B) | 421 | 3.89 | 6 |
| 60 | 161.4 (B) | 393 | 3.45 | 6 |
| 99 | 223.3 (B) | 431 | 3.16 | 6 |
| 134 | n.d. | 367 | 1.93 | 1 |
| 61 | 186.7 (B) | 407 | 3.77 | 4 |
| 62 | 231.4 (B) | 423 | 3.36 | 4 |
| 63 | 148.8 (B) | 444 | 2.19 | 6 |
| 64 | 68.3 (B) | 423 | 3.23 | 4 |
| 65 | 209.8 (B) | 421 | 4.00 | 6 |
| 66 | n.d. | 423 | 3.20 | 6 |
| 67 | n.d. | 429 | 3.81 | 6 |
| 68 | n.d. | 395 | 3.82 | 6 |
| 69 | n.d. | 353 | 3.15 | 6 |
| 135 | n.d. | 458 | 1.97 | 1 |
| 70 | 128.8 (B) | 437 | 3.33 | 4 |
| 136 | 104.2 (B) | 445 | 2.15 | 6 |
| 20 | 199.2 (B) | 434 | 3.69 | 4 |
| 100 | 225 (B) | 417 | 3.50 | 4 |
| 101 | 214.9 (B) | 444 | 2.41 | 4 |
| 46 | 223 (B) | 450 | 3.84 | 4 |
| 94 | n.d. | 460 | 2.82 | 5 |
| 93 | n.d. | 460 | 2.82 | 5 |
| 71 | 208.2 (B) | 393 | 3.65 | 4 |
| 72 | 108.6 (B) | 395 | 3.02 | 4 |
| 35 | 227.3 (B) | 430 | 3.79 | 4 |
| 25 | 258.4 (B) | 416 | 3.69 | 4 |
| 11 | 164.7 (B) | 446 | 2.62 | 4 |
| 12 | n.d. | 434 | 3.39 | 4 |
| 92 | >300 | 460 | 2.35 | 4 |
| 31 | 160.4 (B) | 460 | 3.68 | 4 |
| 102 | n.d. | 446 | 3.72 | 4 |
| 103 | 248.3 (B) | 417 | 3.11 | 4 |
| 104 | 184.48 (A) | 434.1237 (−0.3 mDa) | 2.63 | 2 |
| 137 | 237.74 (A) | 421.1492 (+0.5 mDa) | 2.41 | 2 |
| 95 | n.d. | 474 | 2.42 | 4 |
| 105 | n.d. | 446 | 3.98 | 4 |
| 96 | 175.2 (B) | 446 | 2.25 | 6 |
| 13 | 196.7 (B) | 434 | 3.70 | 4 |
| 13a | 146.4 (B) | 434 | 3.70 | 4 |
| 14 | 249.5 (B) | 430 | 2.44 | 6 |
| 138 | 212.65 (A) | 381.1179 (+0.5 mDa) | 1.91 | 2 |
| 84 | 196.7 (B) | 462 | 2.41 | 4 |
| 97 | 94.5 (B) | 362 | 1.98 | 4 |
| 139 | 204.9 (B) | 406 | 3.22 | 4 |
| 53 | 145.5 (B) | 448 | 2.89 | 4 |
| 54 | 141.3 (B) | 462 | 2.46 | 4 |
| 140 | 246.7 (B) | 422 | 3.69 | 4 |
| 141 | 224.9 (B) | 417 | 3.41 | 4 |
| 17 | 211.9 (B) | 430 | 3.73 | 4 |
| 142 | 257.9 (B) | 405 | 2.18 | 4 |
| 16 | 200.8 (B) | 446 | 2.46 | 4 |
| 52 | 197.4 (B) | 448 | 2.40 | 4 |
| 47 | 120.57 and 140.43 (A) (*) | 450.0959 (+1.5 mDa) | 2.39 | 2 |
| 15 | 136.3 (B) | 430 | 2.62 | 4 |
| 98 | 179.56 (A) | 434.0589 (+0.2 mDa) | 2.72 | 2 |
| 26 | 197.4 (B) | 416 | 2.88 | 4 |
| 18 | n.d. | 430 | 3.43 | 4 |
| 37 | 202.8 (B) | 444 | 2.99 | 4 |
| 36 | 156.85 (A) | 430.1508 (+1.7 mDa) | 2.32 | 2 |
| 106 | n.d. | 451.0906 (+0.9 mDa) | 2.44 | 2 |
| 112 | n.d. | 431.1448 (+0.5 mDa) | 2.41 | 2 |
| 109 | 153.31 (A) | 464.1101 (0.0 mDa) | 2.5 | 2 |
| 124 | 194.50 (A) | 448 | 2.39 | 3 |
| 133 | 167.78 (A) | 482 | 2.62 | 3 |
| 116 | 213.63 (A) | 417 | 2.24 | 3 |
| 118 | 201.71 (A) | 444 | 2.39 | 3 |
| 107 | 189.26 A | 478 | 2.5 | 3 |
| 108 | 212.88 (A) | 468 | 2.76 | 3 |
| 126 | 229.17 (A) | 478 | 2.5 | 3 |
| 132 | 224.82 (A) | 460.1598 (+0.2 mDa) | 2.35 | 2 |

TABLE 3-continued

Analytical data - melting point (M.p.) and LCMS:
[M + H]+ means the protonated mass of the free base of the compound,
R$_t$ means retention time (in min), method refers to the method
used for LCMS. For some compounds, exact mass was determined.

| Co. No. | M.p. (° C.) | [M + H]+ | R$_t$ | LCMS Method |
|---|---|---|---|---|
| 127 | 185.94 (A) | 494.1207 (0.0 mDa) | 2.55 | 2 |
| 111 | 161.92 (A) | 458.1803 (−0.1 mDa) | 2.53 | 2 |
| 110 | 221.63 (A) | 448.1395 (−0.1 mDa) | 2.78 | 2 |
| 28 | 233.4 (B) | 430 | 2.87 | 4 |
| 39 | 144.6 (B) | 448 | 3.90 | 4 |
| 40 | 194.8 (B) | 460 | 3.45 | 4 |
| 41 | 180.0 (B) | 382 | 2.56 | 4 |
| 21 | 179.0 (B) | 434 | 2.94 | 4 |
| 81 | 186.35 (A) | 466.1309 (+0.6 mDa) | 2.53 | 2 |
| 29 | 210.8 (B) | 447 | 3.34 | 4 |
| 38 | 186.5 (B) | 444 | 2.70 | 4 |
| 32 | 243.4 (B) | 460 | 2.66 | 4 |
| 117 | 259.0 (B) | 464 | 3.72 | 4 |
| 27 | 174.0 (B) | 434 | 3.80 | 4 |
| 78 | 183.36 (A) | 452.1147 (+0.1 mDa) | 2.69 | 2 |
| 30 | 225.0 (B) | 430 | 2.60 | 4 |
| 33 | 216.6 | 460 | 2.87 | 4 |
| 73 | 275 (B) | 339 | 2.92 | 4 |
| 75 | n.d. | 353.1225 (0.0 mDa) | 1.87 | 2 |
| 74 | n.d. | 373.0685 (+0.6 mDa) | 1.94 | 2 |
| 76 | n.d. | 339 | 1.01 | 7 |
| 80 | 233.33 (A) | 369 | 1.72 | 3 |
| 77 | 261.95 (A) | 415.1032 (+0.3 mDa) [M + CH3COO]− (**) | 1.79 | 2 |
| 82 | n.d. | 305 | 2.67 | 4 |
| 128 | 213.44 (A) | 454 | 2.55 | 3 |
| 113 | 181.5 (B) | 435 | 3.559 | 4 |
| 34 | 191.5 (B) | 476 | 3.317 | 4 |
| 50 | 168.1 (B) | 468 | 3.91 | 4 |
| 115 | 193.3 (B) | 447 | 3.519 | 4 |
| 24 | 204.0 (B) | 452 | 3.766 | 4 |
| 130 | 211.11 (A) | 448.0744 (+0.1 mDa) | 2.66 | 2 |
| 131 | 186.35 (A) | 466.1309 (+0.6 mDa) | 2.53 | 2 |
| 125 | 156.83 (A) | 462.1553 (0.0 mDa) | 2.66 | 2 |
| 129 | 189.99 (A) | 414.1133 (0.0 mDa) | 2.34 | 2 |
| 79 | 182.00 (A) | 428.1291 (+0.2 mDa) | 2.56 | 2 |
| 143 | 201.6 (B) | 474 | 2.59 | 4 |
| 22 | 246.7 (B) | 448 | 2.92 | 4 |
| 51 | 214.9 (B) | 480 | 3.52 | 4 |
| 123 | 251.93 (A) | 431 | 2.3 | 3 |
| 43 | 223.3 (B) | 396 | 2.43 | 4 |
| 114 | 175.3 (B) | 462 | 2.61 | 4 |
| 49 | 252.5 (B) | 464 | 2.82 | 4 |
| 44 | 210.9 (B) | 410 | 2.63 | 4 |
| 45 | 165.9 (B) | 414 | 3.79 | 4 |
| 48 | 216.6 (B) | 464 | 3.08 | 4 |
| 42 | 186.5 (B) | 400 | 3.54 | 4 |
| 145 | 209.5 (A) | 435.1194 (+0.2 mDa) | 2.52 | 2 |
| 146 | 172.9 (A) | 435.0545 (+0.6 mDa) | 2.59 | 2 |
| 147 | 212.57 (A) | 446.1439 (−0.1 mDa) | 1.75 | 2 |
| 148 | 150.83 (A) | 446.1439 (−0.1 mDa) | 1.83 | 2 |
| 149 | 121.94 (A) | 460.1600 (+0.4 mDa) | 2.27 | 2 |
| 150 | 169.28 (A) | 446.1437 (−0.3 mDa) | 1.91 | 2 |
| 151 | 152.64 (A) (*) | 448.1402 (+0.6 mDa) | 2.35 | 2 |
| 152 | 145.36 (A) | 466.0898 (+0.4 mDa) | 2.43 | 2 |
| 153 | 229.9 (B) | 402 | 2.56 | 4 |
| 154 | 184.10 (A) | 447.1393 (+0.1 mDa) | 2.23 | 2 |
| 155 | 184.37 (A) | 447.1398 (+0.6 mDa) | 2.23 | 2 |
| 156 | 105.42 (A) | 480.1048 (−0.2 mDa) | 2.41 | 2 |
| 157 | n.d. | 480.1054 (+0.4 mDa) | 2.41 | 2 |
| 158 | n.d. | 446 | 1.2 | 7 |
| 159 | n.d. | 446 | 2.15 | 1 |
| 160 | 178.1 (B) | 424 | 2.53 | 4 |
| 161 | 233.4 (B) | 397 | 3.54 | 4 |
| 162 | 250.1 (B) | 383 | 3.31 | 4 |
| 163 | n.d. | 447 | 3.48 | 4 |
| 164 | n.d. | 480.1063 (+1.3 mDa) | 2.41 | 2 |
| 165 | n.d. | 446.1436 (−0.4 mDa) | 2.18 | 2 |
| 166 | n.d. | 319 | 2.93 | 4 |
| 167 | 205.04 (A) (*) | 495.0746 (−0.4 mDa)(***) [M − H]− | 2.98 | 9 | n.d. = not determined
(*) Multiple crystalline forms detected. MP related to the main/highest peak
(**) The compound was not directly ionizable. The type of adduct is specified: [M + CH$_3$COO]−.
(***)The reported molecular ion corresponds to the [M − H]−(deprotonated molecule).

Optical Rotations

Optical rotations were measured on a Perkin-Elmer 341 polarimeter with a sodium lamp and reported as follows: [α]° (λ, c g/100 ml, solvent, T° C.). $[α]_λ^T=(100α)/(l×c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 4

Optical Rotation data.

| Co. No. | α$_D$ (°) | Wavelength (nm) | Concentration w/v % | Solvent | Temp. (° C.) |
|---|---|---|---|---|---|
| 128 | +11.4 | 589 | 0.47 | DMF | 20 |
| 80 | +16.2 | 589 | 0.57 | DMF | 20 |
| 125 | +8.6 | 589 | 0.53 | DMF | 20 |
| 130 | +10.5 | 589 | 0.59 | DMF | 20 |
| 79 | +8.4 | 589 | 0.62 | DMF | 20 |
| 123 | +9.4 | 589 | 1 | DMF | 20 |
| 55 | +12.0 | 589 | 0.59 | DMF | 20 |
| 5 | +8.4 | 589 | 0.66 | DMF | 20 |
| 56 | +9.2 | 589 | 0.45 | DMF | 20 |
| 122 | −1.0 | 589 | 0.5 | DMF | 20 |
| 119 | +3.6 | 589 | 0.58 | DMF | 20 |
| 83 | −1.1 | 589 | 0.49 | DMF | 20 |
| 104 | +10.5 | 589 | 0.57 | DMF | 20 |
| 138 | +12.6 | 589 | 0.42 | DMF | 20 |
| 47 | +8.9 | 589 | 0.83 | DMF | 20 |
| 98 | +7.2 | 589 | 0.53 | DMF | 20 |
| 36 | +5.9 | 589 | 0.65 | DMF | 20 |
| 124 | +7.9 | 589 | 0.58 | DMF | 20 |
| 133 | +8.4 | 589 | 0.5 | DMF | 20 |
| 116 | +6.3 | 589 | 0.57 | DMF | 20 |
| 126 | +9.1 | 589 | 0.66 | DMF | 20 |
| 132 | +7.2 | 589 | 0.53 | DMF | 20 |
| 127 | +6.4 | 589 | 0.5 | DMF | 20 |
| 81 | +9.4 | 589 | 0.55 | DMF | 20 |
| 129 | +10.6 | 589 | 0.51 | DMF | 20 |
| 118 | +7.2 | 589 | 0.55 | DMF | 20 |
| 78 | +10.5 | 589 | 0.51 | DMF | 20 |
| 77 | +18.1 | 589 | 0.57 | DMF | 20 |
| 145 | +37.8 | 589 | 0.55 | DMF | 20 |
| 146 | +35.2 | 589 | 0.55 | DMF | 20 |
| 147 | +4.6 | 589 | 0.50 | DMF | 20 |
| 148 | +8.5 | 589 | 0.56 | DMF | 20 |
| 149 | +9.8 | 589 | 1.10 | DMF | 20 |
| 150 | +9.7 | 589 | 0.52 | DMF | 20 |
| 151 | +10.4 | 589 | 0.53 | DMF | 20 |
| 152 | +9.1 | 589 | 0.58 | DMF | 20 |
| 154 | −25.4 | 589 | 0.49 | DMF | 20 |
| 155 | +26.8 | 589 | 0.49 | DMF | 20 |

TABLE 4-continued

Optical Rotation data.

| Co. No. | $\alpha_D$ (°) | Wavelength (nm) | Concentration w/v % | Solvent | Temp. (° C.) |
|---|---|---|---|---|---|
| 156 | −32.7 | 589 | 0.51 | DMF | 20 |
| 157 | +27.6 | 589 | 0.49 | DMF | 20 |
| 158 | −23.9 | 589 | 1.30 | DMF | 20 |
| 159 | +25.5 | 589 | 0.96 | DMF | 20 |
| 167 | −22.5 | 589 | 0.50 | DMF | 20 |

SFC-MS
General Procedure

The SFC measurement was performed using Analytical system from Berger instrument comprising a FCM-1200 dual pump fluid control module for delivering carbon dioxide ($CO_2$) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 µa, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

TABLE 5

Analytical SFC-MS Methods (Flow expressed in mL/min; column temperature (T) in ° C.; Pressure in Mpa).

| Method | Column | Mobile Phase | Flow | T | Pressure |
|---|---|---|---|---|---|
| 1 | Chiralpak IC 150 mm × 4.6 mm Daicel | $CO_2$/EtOH (0.3% $IPrNH_2$) 70/30 | 3 | 35 | 100 |
| 2 | Chiralcel OD-H 150 mm × 4.6 mm 5 µm Daicel | $CO_2$/iPrOH(0.3% $IPrNH_2$) 75/25 | 3 | 35 | 100 |
| 3 | Chiralpak IC 150 mm × 4.6 mm 5 µm Daicel | $CO_2$/EtOH(0.3% $IPrNH_2$) 60/40 | 3 | 35 | 100 |

TABLE 6

Analytical SFC data - $R_t$ means retention time (in minutes), $[M + H]^+$ means the protonated mass of the compound, method refers to the method used for SFC/MS analysis of enantiomerically pure compounds. The measurement was compared against the mixture.

| Co. No. | $R_t$ | $[M + H]^+$ | UV Area % | Isomer Elution Order* | Method |
|---|---|---|---|---|---|
| 93 | 2.55 | 460 | 100 | A | 1 |
| 94 | 4.8 | 460 | 100 | B | 1 |
| 155 | 2.96 | 447 | 100 | A | 2 |
| 154 | 4.07 | 447 | 100 | B | 2 |
| 157 | 2.76 | 480 | 100 | A | 3 |
| 156 | 4.85 | 480 | 100 | B | 3 |
| 159 | 2.5 | 446 | 100 | A | 3 |
| 158 | 3.6 | 446 | 100 | B | 3 |

*A means the first isomer that elutes. B means the second isomer that elutes.

Pharmacological Examples

The compounds provided in the present invention are negative allosteric modulators of mGluR2. These compounds appear to inhibit glutamate responses by binding to an allosteric site other than the glutamate binding site. The response of mGluR2 to a concentration of glutamate is decreased when compounds of Formula (I) are present. Compounds of Formula (I) are expected to have their effect substantially at mGluR2 by virtue of their ability to reduce the function of the receptor. The effects of negative allosteric modulators tested at mGluR2 using the [$^{35}$S]GTPγS binding assay method described below and which is suitable for the identification of such compounds, and more particularly the compounds according to Formula (I), are shown in Table 7.

A) In Vitro Pharmacology

1) [$^{35}$S]GTPγS Binding Assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein α subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the antagonist can be determined. mGlu2 receptors are shown to be preferentially coupled to Gαi-protein, a preferential coupling for this method, and hence it is widely used to study receptor activation of mGlu2 receptors both in recombinant cell lines and in tissues. Here we describe the use of the [$^{35}$S]GTPγS binding assay using membranes from cells transfected with the human mGlu2 receptor and adapted from Schaffhauser et al. (Molecular Pharmacology, 2003, 4:798-810) for the detection of the negative allosteric modulation (NAM) properties of the compounds of this invention.

Membrane Preparation

CHO-cells were cultured to pre-confluence and stimulated with 5 mM butyrate for 24 h. Cells were then collected by scraping in PBS and cell suspension was centrifuged (10 min at 4000 RPM in benchtop centrifuge). Supernatant was discarded and pellet gently resuspended in 50 mM Tris-HCl, pH 7.4 by mixing with an Ultra Turrax homogenizer. The suspension was centrifuged at 12,400 RPM (Sorvall F14S-6x250Y) for 10 minutes and the supernatant discarded. The pellet was homogenized in 5 mM Tris-HCl, pH 7.4 using an Ultra Turrax homogenizer and centrifuged again (13,000 RPM, 20 min, 4° C.). The final pellet was resuspended in 50 mM Tris-HCl, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 negative allosteric modulatory activity of test compounds was performed as follows. Test compounds and glutamate were diluted in assay buffer containing 10 mM HEPES acid, 10 mM HEPES salt, pH 7.4, 100 mM NaCl, 3 mM $MgCl_2$ and 10 µM GDP. Human mGlu2 receptor-containing membranes were thawed on ice and diluted in assay buffer supplemented with 18 µg/ml saponin. Membranes were pre-incubated with compound together with a predefined (~$EC_{80}$) concentration of glutamate (60 µM) for 30 min at 30° C. After addition of [$^{35}$S]GTPγS (f.c. 0.1 nM), assay mixtures were shaken briefly and further incubated to allow [$^{35}$S]GTPγS incorporation on activation (30 minutes, 30° C.). Final assay mixtures contained 7 µg of membrane protein in 10 mM HEPES acid, 10 mM HEPES salt, pH 7.4, 100 mM NaCl, 3 mM MgCl$_2$, 10 µM GDP and 10 µg/ml saponin. Total reaction volume was 200µ Reactions were terminated by rapid filtration through Unifilter-96 GF/B plates (Perkin Elmer, Massachusetts, USA) using a 96-well filtermate universal harvester. Filters were washed 6 times with ice-cold 10 mM NaH$_2$PO$_4$/10 mM Na$_2$HPO$_4$, pH 7.4. Filters were then air-dried, and 30 µl of liquid scintillation cocktail (Microscint-O) was added to each well. Membrane-bound radioactivity was counted in a Topcount.

Data Analysis

The concentration-response curves of representative compounds of the present invention were generated using the Lexis software interface (developed at J&J). Data were calculated as % of the control glutamate response, defined as the response that is generated upon addition of an EC$_{80}$-equivalent concentration of glutamate. Sigmoid concentration-response curves plotting these percentages versus the log concentration of the test compound were analyzed using non-linear regression analysis. The concentration producing half-maximal inhibition was calculated as the IC$_{50}$. The pIC$_{50}$ values were calculated as the –log IC$_{50}$, when the IC$_{50}$ is expressed in M. E$_{max}$ is defined as the relative maximal effect (i.e. maximal % inhibition relative to the control glutamate response).

TABLE 7

Pharmacological data for compounds according to the invention.

| Co. No. | GTPγS-hmGluR2 anGT pIC$_{50}$ | GTPγS-hmGluR2 anGT Emax |
|---|---|---|
| 73 | 5.87 | 95 |
| 55 | 8.25 | 101 |
| 19 | 8.58 | 104 |
| 134 | 7.2 | 103 |
| 5 | 8.52 | 105 |
| 135 | 6.16 | 111 |
| 69 | 6.34 | 103 |
| 66 | 6.73 | 103 |
| 57 | 8.77 | 102 |
| 68 | 6.58 | 102 |
| 65 | 6.75 | 107 |
| 67 | 6.7 | 104 |
| 136 | 5.81 | 104 |
| 7 | 8.33 | 103 |
| 59 | 7.45 | 103 |
| 9 | 7.95 | 103 |
| 99 | 7.34 | 100 |
| 63 | 6.93 | 99 |
| 60 | 7.36 | 103 |
| 56 | 8.53 | 104 |
| 2 | 8.77 | 103 |
| 6 | 8.51 | 107 |
| 61 | 7.15 | 104 |
| 85 | 8.66 | 106 |
| 89 | 7.98 | 107 |
| 86 | 8.64 | 105 |
| 91 | 7.73 | 103 |
| 90 | 7.8 | 106 |
| 88 | 8.07 | 106 |
| 87 | 8.46 | 112 |
| 58 | 7.74 | 113 |
| 62 | 7.11 | 104 |
| 70 | 6.09 | 106 |
| 122 | 7.67 | 113 |
| 83 | 7.81 | 111 |
| 119 | 8.11 | 111 |
| 120 | 8.4 | 107 |
| 121 | 8.01 | 109 |
| 64 | 6.77 | 107 |
| 3 | 8.68 | 116 |

TABLE 7-continued

Pharmacological data for compounds according to the invention.

| Co. No. | GTPγS-hmGluR2 anGT pIC$_{50}$ | GTPγS-hmGluR2 anGT Emax |
|---|---|---|
| 144 | 8.32 | 114 |
| 1 | 8.72 | 111 |
| 10 | 7.7 | 113 |
| 4 | 8.52 | 117 |
| 8 | 8.36 | 123 |
| 14 | 8.61 | 109 |
| 95 | 8.26 | 112 |
| 13 | 8.65 | 110 |
| 13a | 8.96 | 106 |
| 96 | 8.53 | 113 |
| 105 | 8.21 | 108 |
| 137 | 7.39 | 107 |
| 104 | 8.09 | 108 |
| 103 | 6.99 | 104 |
| 102 | 7.67 | 112 |
| 31 | 7.64 | 109 |
| 92 | 7.32 | 117 |
| 12 | 7.32 | 110 |
| 11 | 6.62 | 109 |
| 25 | 8.51 | 112 |
| 35 | 8.4 | 114 |
| 72 | 6.56 | 111 |
| 71 | 7.15 | 111 |
| 93 | 5.27 | 95 |
| 94 | 7.7 | 115 |
| 46 | 8.56 | 113 |
| 101 | 8.57 | 118 |
| 100 | 8.53 | 119 |
| 20 | 7.97 | 113 |
| 138 | 6.78 | 114 |
| 84 | 8.13 | 112 |
| 97 | 6.83 | 114 |
| 139 | 7.59 | 109 |
| 53 | 8.61 | 114 |
| 54 | 8.28 | 118 |
| 140 | 8.03 | 111 |
| 141 | 8.08 | 113 |
| 17 | 7.39 | 107 |
| 142 | 6.67 | 110 |
| 16 | 7.86 | 115 |
| 52 | 8.59 | 118 |
| 47 | 8.97 | 109 |
| 15 | 6.62 | 106 |
| 98 | 8.44 | 107 |
| 26 | 9.08 | 107 |
| 18 | 7.95 | 107 |
| 37 | 9.14 | 108 |
| 36 | 9.07 | 111 |
| 106 | 8.94 | 111 |
| 112 | 8.95 | 106 |
| 109 | 8.91 | 109 |
| 124 | 8.65 | 107 |
| 133 | 9.04 | 105 |
| 116 | 8.87 | 109 |
| 118 | 8.8 | 105 |
| 107 | 8.83 | 107 |
| 108 | 8.55 | 104 |
| 126 | 8.93 | 108 |
| 132 | 7.91 | 105 |
| 127 | 8.39 | 108 |
| 111 | 8.84 | 109 |
| 110 | 8.3 | 107 |
| 28 | 9.06 | 107 |
| 39 | 9.03 | 112 |
| 40 | 8.67 | 111 |
| 41 | 8.21 | 106 |
| 21 | 8.72 | 108 |
| 81 | 7.71 | 106 |
| 29 | 8.75 | 107 |
| 38 | 8.94 | 108 |
| 32 | 8.46 | 111 |
| 117 | 8.43 | 105 |
| 27 | 9.09 | 108 |

TABLE 7-continued

Pharmacological data for compounds according to the invention.

| Co. No. | GTPγS-hmGluR2 anGT pIC$_{50}$ | GTPγS-hmGluR2 anGT Emax |
|---|---|---|
| 78 | 7.87 | 106 |
| 30 | 8.96 | 111 |
| 33 | 8.43 | 111 |
| 128 | 8.54 | 106 |
| 34 | 7.98 | 107 |
| 113 | 8.5 | 107 |
| 50 | 8.76 | 108 |
| 115 | 8.16 | 108 |
| 24 | 8.49 | 107 |
| 131 | 8.53 | 110 |
| 125 | 8.63 | 110 |
| 130 | 9.07 | 110 |
| 129 | 8.21 | 110 |
| 79 | 8.78 | 112 |
| 143 | 8.09 | 116 |
| 22 | 8.45 | 109 |
| 51 | 8.85 | 113 |
| 145 | 8.91 | 126 |
| 146 | 9.02 | 128 |
| 147 | 7.27 | 103 |
| 148 | 7.73 | 105 |
| 149 | 7.69 | 104 |
| 150 | 8.09 | 107 |
| 151 | 8.57 | 115 |
| 152 | 8.98 | 108 |
| 153 | 6.91 | 111 |
| 154 | 8.31 | 113 |
| 155 | 6.48 | 106 |
| 156 | 8.77 | 107 |
| 157 | 6.55 | 104 |
| 158 | 8.48 | 108 |
| 159 | 6.10 | 108 |
| 160 | 8.45 | 112 |
| 161 | 8.55 | 108 |
| 162 | 8.17 | 109 |
| 163 | 7.99 | 107 |
| 164 | 8.72 | 108 |
| 165 | 8.03 | 106 |
| 166 | no data | |
| 167 | 7.37 | 107 |

B) In Vivo Pharmacology

1) Reversal of LY-404039-Induced Decrease of Palpebral Opening in Apomorphine-Challenged Rats.

Male Wiga Wistar rats (Crl:WI; Charles River Germany; 220±40 g) were housed under standard laboratory conditions (21±2° C.; 50-65% relative humidity; light-dark cycle set at 12 h; lights on at 6.00 h) and fasted overnight prior to the start of the experiments (tap water remained available ad libitum). During the test period, they were housed in individual cages. Palpebral opening was scored every 5 min over the first hour after injection of apomorphine (1.0 mg/kg, i.v.) in animals either pretreated or not pretreated with LY-404039 (2.5 mg/kg, s.c.) at 1 h prior to the apomorphine injection. The animals were also pretreated with test compound or solvent at a predefined interval before apomorphine challenge. The score system was: (5) exophthalmos, (4) wide open, (3) open for three-quarters, (2) half open, (1) open for one-quarter, (0) closed. The scores for palpebral opening were cumulated over the 60-min observation period. A cumulative palpebral opening score >26 was selected for drug-induced reversal of the LY-404039-induced decrease of palpebral opening (occurrence in 3.2% of control animals pretreated with LY-404039 (n=154) versus in 99.5% of control rats not pretreated with LY-404039 (n=6335)).

Table 8 shows the palpebral opening score in control animals receiving apomorphine alone and in animals receiving apomorphine and LY-404039. In animals receiving apomorphine alone the median palpebral opening is 43 whereas in animals receiving apomorphine and LY-404039, the median palpebral opening is 17. In animals treated with apomorphine alone, the palpebral opening score is almost always (in 95.5% of the rats) greater than 34, whereas in animals treated with the combination (apomorphine+LY-404039) only 3.2% of the animals show a palpebral opening greater than 26.

TABLE 8

Palpebral opening score in control animals.

| Measurement | Apomorphine alone (n = 6335) | Apomorphine + LY-404039 (n = 154) |
|---|---|---|
| Palpebral opening score | | |
| Median score: | 43 | 17 |
| Occurrence score > 26 (%): | 99.5 | 3.2 |
| Occurrence score > 34 (%): | 95.9 | 0.0 |

2) Reversal of the Effect of the mGluR2 PAM JNJ-42153605-Induced Inhibition of Scopolamine-Induced Hyperlocomotion Apparatus Motor activity was measured in microprocessor-based motor activity arenas (closed gray PVC cylinders with a height of 39 cm and a diameter of 31 cm). Each arena was placed on an infrared LED (8×8 LEDs) lit box (white PVC squared box; 40×40 cm$^2$; height 12.5 cm. An infrared-sensitive tube camera and a white light source were mounted to the ceiling above the observation chamber to track the animal. The total distance traveled (cm) was recorded and analyzed using the Noldus Ethovision XT Video Tracking System (Version 7.0.418; Noldus, Wageningen, The Netherlands). The intensity of the light within the activity cages (measured in the centre at the level of the floor) ranged between 4 and 8 LUX.

General Procedure

The rats were pretreated with test compound or vehicle at 60 min before the start of the activity recordings and placed into individual cages. The rats were challenged with JNJ-42153605 (3-(cyclopropylmethyl)-7-(4-phenylpiperidin-1-yl)-8-(trifluoromethyl)[1,2,4]triazolo[4,3-a]pyridine; WO2010/130424; Cid et al. *J. Med. Chem.* 2012, 55, 8770-8789) (20 mg/kg, i.v.) 30 min before the start of the activity recording combined with scopolamine (0.16 mg/kg, i.v.) just before the start of the activity measurements. Immediately after the injection of scopolamine, the rats were placed into the activity monitors and total distance traveled over the first 30 min was measured.

Solvent-Pretreated Control Rats.

Frequency distributions obtained in a historical series of solvent-pretreated control rats are given in Table 9 below. Animals receiving the combination of JNJ-42153605 and scopolamine (n=433) almost always traveled a distance of less than 1500 cm (<1500 cm) (only 2.5% of the control rats traveled a distance of more than 1500 cm (>1500 cm)). On the other hand, animals challenged with scopolamine alone (n=215) always traveled a total distance of more than 1500 cm (>1500 cm) and almost always (in 95.8% of the rats) a distance of more than 4400 cm (>4400 cm). Rats that did not receive any challenge traveled almost always a distance of more than 1500 cm (>1500 cm) (in 93.3% of the rats) and less than 4400 cm (<4400 cm) (in 98.9% of the rats). For reversal of the inhibitory effect of JNJ-42153605 on the scopolamine-induced hyperlocomotion, the following all-or-none criteria were adopted: (1) reversal: total distance >1500 cm.

TABLE 9

Frequency distributions obtained in historical series of solvent-pretreated control rats. $N_{tested}$ means number of animals tested.

|  | Median (cm) | >1500 cm (%) | >4400 cm (%) | $N_{tested}$ |
|---|---|---|---|---|
| Combination | 480 | 2.5 | 0.0 | 433 |
| No challenge | 2618 | 93.3 | 1.1 | 638 |
| Scopolamine | 7246 | 100 | 95.8 | 215 |

3) Induction of Mydriasis

The pupil diameter of Wiga rats was measured with a microscopic micrometer (1 unit=1/24 mm). Criteria for drug-induced effects: pupil diameter >25 units for mydriasis (in controls: 1.9%) 1 h post-administration of the test compound (test 1) or 1, 2 or 3 h post-administration of the test compound (test 2, wherein the maximum pupil diameter over the full 3 h period is reported).

Table 10 below provides the data obtained in the tests 1)-3) described above:

TABLE 10

Summary of data in tests 1)-3). In the table: SCOP JNJ-42153605 means Reversal of the effect of JNJ 42153605 on scopolamine-induced hyperlocomotion, APO LY-404039 means Reversal of LY-404039-induced decrease of palpebral opening in apomorphine challenged rats, MYD means Induction of mydriasis, $ED_{50}$ means median effective dose; PO means oral route; SC means subcutaneous route.

| | | $ED_{50}$ (mg/kg) | | | |
|---|---|---|---|---|---|
| Co. | | SCOP JNJ- | APO LY- | MYD | |
| No. | Route | 42153605 | 404039 | Test 1 | Test 2 |
| 19 | PO | 0.79 | | | |
| 5 | PO | 1.27 | 0.32 | >10 | |
| 7 | PO | >2.5 | | | |
| 9 | PO | 0.32 | >2.5 | | >10 |
| 85 | PO | 1.26 | | | |
| 89 | PO | >2.5 | | | |
| 86 | PO | 1.26 | | | |
| 88 | | | >2.5 | | |
| 87 | PO | >2.5 | | | |
| 3 | PO | 0.08 | | | |
| 144 | PO | 1.01 | 1.99 | | |
| 1 | PO | 0.20 | 0.39 | | >40 |
| 4 | PO | 1.01 | | | |
| 8 | PO | 1.26 | 0.2 | | >10 |
| 14 | PO | 0.13 | 0.13 | | |
| 95 | PO | >2.5 | | | |
| 13 | PO | 0.32 | 0.32 | | |
| 96 | PO | 1.99 | | | |
| 105 | PO | >2.5 | | | |
| 104 | PO | >0.63 | | | |
| 25 | PO | >2.5 | >10 | | |
| 35 | PO | >2.5 | >10 | | |
| 46 | PO | >2.5 | 1.99 | | |
| 101 | PO | 0.5 | 0.79 | | >10 |
| 100 | PO | 0.2 | 0.32 | | |
| 20 | PO | >2.5 | >2.5 | | |
| 84 | | | >2.5 | | |
| 140 | PO | >2.5 | | | |
| 141 | PO | >2.5 | | | |
| 47 | PO | 0.5 | | | 32 |
| 98 | PO | >0.63 | | | |
| 26 | PO | 0.32 | | | 5 |
| 18 | PO | >0.63 | | | |
| 37 | PO | >0.63 | >0.63 | | |

TABLE 10-continued

Summary of data in tests 1)-3). In the table: SCOP JNJ-42153605 means Reversal of the effect of JNJ 42153605 on scopolamine-induced hyperlocomotion, APO LY-404039 means Reversal of LY-404039-induced decrease of palpebral opening in apomorphine challenged rats, MYD means Induction of mydriasis, $ED_{50}$ means median effective dose; PO means oral route; SC means subcutaneous route.

| | | $ED_{50}$ (mg/kg) | | | |
|---|---|---|---|---|---|
| Co. | | SCOP JNJ- | APO LY- | MYD | |
| No. | Route | 42153605 | 404039 | Test 1 | Test 2 |
| 36 | PO | 0.2 | | | 20 |
| 106 | PO | 0.32 | | | |
| 112 | PO | 0.2 | | | |
| 109 | PO | 0.32 | | | 32 |
| 124 | PO | 0.2 | | | >40 |
| 133 | PO | >0.63 | | | |
| 116 | PO | 0.05 | | | 5 |
| 118 | PO | >0.63 | >0.63 | | 1.3 |
| 107 | PO | >0.63 | >0.63 | | |
| 108 | PO | >0.63 | | | |
| 126 | PO | >0.63 | >0.63 | | |
| 132 | PO | >0.63 | | | |
| 127 | PO | >0.63 | | | |
| 111 | PO | 0.32 | | | |
| 110 | PO | >0.63 | | | |
| 28 | PO | >0.63 | | | |
| 39 | PO | 0.32 | | | 5 |
| 40 | PO | >0.63 | >0.63 | | |
| 41 | PO | >0.63 | 0.32 | | |
| 21 | PO | 0.32 | | | 7.9 |
| 29 | PO | >0.63 | | | |
| 38 | PO | 0.20 | | | 2 |
| 32 | PO | >0.63 | | | |
| 117 | PO | 0.51 | | | >10 |
| 27 | PO | 0.32 | | | >10 |
| 78 | PO | >0.63 | | | |
| 30 | PO | 0.51 | | | 3.1 |
| 33 | PO | >0.63 | | | |
| 147 | PO | >0.63 | | | |
| 151 | PO | >0.63 | | | |
| 152 | PO | 0.08 | | | |
| 154 | PO | 0.63 | | | |
| 156 | PO | 0.20 | | | |
| 158 | PO | >0.63 | | | |
| 160 | PO | >0.63 | | | |
| 161 | PO | >0.63 | | | |
| 162 | PO | 0.13 | | | >10 |

Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

We claim:

1. A method of treating a depressive disorder comprising administering a compound of Formula (I) to a patient in need thereof

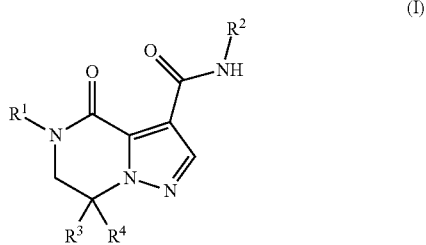

or a stereoisomeric form thereof, wherein $R^1$ is phenyl or 2-pyridinyl, each optionally substituted with one or more substituents each independently selected from the group consisting of halo, $C_{1-4}$alkyl, monohalo-$C_{1-4}$alkyl, polyhalo-$C_{1-4}$alkyl, —CN, $C_{3-7}$cycloalkyl, monohalo-$C_{1-4}$alkyloxy, polyhalo-$C_{1-4}$alkyloxy, $SF_5$, $C_{1-4}$alkylthio, monohalo-$C_{1-4}$alkylthio and polyhalo-$C_{1-4}$alkylthio;

$R^2$ is selected from the group consisting of hydrogen; $C_{1-4}$alkyl; $C_{3-7}$cycloalkyl; Het$^1$; Aryl; —C(O)R$^5$; —C(O)Het$^2$; Het$^2$; and $C_{1-4}$alkyl substituted with one or more substituents each independently selected from the group consisting of halo, C3-7cycloalkyl, Aryl, Het$^1$ and Het$^2$;

$R^5$ is selected from the group consisting of hydrogen, $C_{1-4}$alkyl and $C_{3-7}$cycloalkyl;

Aryl is phenyl optionally substituted with one or more substituents each independently selected from the group consisting of halo, $C_{1-4}$alkyl, monohalo-$C_{1-4}$alkyl, polyhalo-$C_{1-4}$alkyl, —CN, —OH, —$C_{1-4}$alkyl-O—$C_{1-4}$alkyl, —NR'R", —NHC(O)$C_{1-4}$alkyl, —C(O)NR'R", —C(O)NH[C(O)$C_{1-4}$alkyl], —S(O)$_2$NR'R", —S(O)$_2$NH[C(O)$C_{1-4}$alkyl] and —S(O)$_2$—$C_{1-4}$alkyl;

Het$^1$ is selected from the group consisting of oxetanyl, tetrahydrofuranyl and tetrahydropyranyl;

Het$^2$ is (a) a 6-membered aromatic heterocyclyl substituent selected from the group consisting of pyridinyl, pyrimidinyl, pyrazinyl and pyridazinyl, each of which may be optionally substituted with one or more substituents each independently selected from the group consisting of halo, $C_{1-4}$alkyl, —$C_{1-4}$alkyl-OH, monohalo-$C_{1-4}$alkyl, polyhalo-$C_{1-4}$alkyl, —CN, —O—$C_{1-4}$alkyl, —OH, —$C_{1-4}$alkyl-O—$C_{1-4}$alkyl, —NR'R", —NHC(O)$C_{1-4}$alkyl, —C(O)NR'R", —C(O)NH[C(O)$C_{1-4}$alkyl], —S(O)$_2$NR'R", —S(O)$_2$NH[C(O)$C_{1-4}$alkyl] and —S(O)$_2$—$C_{1-4}$alkyl; or (b) a 5-membered aromatic heterocyclyl selected from the group consisting of thiazolyl, oxazolyl, 1H-pyrazolyl and 1H-imidazolyl, each of which may be optionally substituted with one or more substituents each independently selected from the group consisting of halo, $C_{1-4}$alkyl, —$C_{1-4}$alkyl-OH, monohalo-$C_{1-4}$alkyl, polyhalo-$C_{1-4}$alkyl, —CN, —O—$C_{1-4}$alkyl, —OH, —$C_{1-4}$alkyl-O—$C_{1-4}$alkyl, —NR'R", —NHC(O)$C_{1-4}$alkyl, —C(O)NR'R", —C(O)NH[C(O)$C_{1-4}$alkyl], —S(O)$_2$NR'R", —S(O)$_2$NH[C(O)$C_{1-4}$alkyl] and —S(O)$_2$—$C_{1-4}$alkyl;

R' and R" are each independently selected from the group consisting of hydrogen and $C_{1-4}$alkyl;

$R^3$ is selected from the group consisting of hydrogen and $C_{1-4}$alkyl; and $R^4$ is selected from the group consisting of hydrogen, $C_{1-4}$alkyl, monohalo-$C_{1-4}$alkyl, polyhalo-$C_{1-4}$alkyl, —$C_{1-4}$alkyl-O—$C_{1-4}$alkyl and —$C_{1-4}$alkyl-OH;

or a N-oxide, or a pharmaceutically acceptable salt thereof.

2. The method of claim 1, wherein $R^1$ is phenyl or 2-pyridinyl, each optionally substituted with one or two substituents each independently selected from the group consisting of halo, $C_{1-4}$alkyl, monohalo-$C_{1-4}$alkyl, polyhalo-$C_{1-4}$alkyl, —CN, —$C_{1-4}$ alkyl-O—$C_{1-4}$alkyl, —O—$C_{1-4}$alkyl, monohalo-$C_{1-4}$ alkyloxy and polyhalo-$C_{1-4}$alkyloxy;

$R^2$ is selected from the group consisting of hydrogen; $C_{1-4}$alkyl; $C_{3-7}$cycloalkyl; Het$^1$; Aryl; —C(O)R$^5$; —C(O)Het$^2$; Het$^2$; and $C_{1-4}$alkyl substituted with one or more substituents each independently selected from the group consisting of $C_{3-7}$cycloalkyl, Aryl, Het$^1$ and Het$^2$;

Aryl is phenyl optionally substituted with a substituent selected from the group consisting of halo, $C_{1-4}$alkyl, —O—$C_{1-4}$alkyl and —S(O)$_2$—$C_{1-4}$alkyl;

Het$^2$ is (a) a 6-membered aromatic heterocyclyl substituent selected from the group consisting of pyridinyl, pyrimidinyl and pyrazinyl, each of which may be optionally substituted with one or two substituents each independently selected from the group consisting of halo, $C_{1-4}$alkyl, —O—$C_{1-4}$alkyl and —NR'R"; or (b) a 5-membered aromatic heterocyclyl selected from the group consisting of thiazolyl, oxazolyl and 1H-imidazolyl, each of which may be optionally substituted with a $C_{1-4}$alkyl substituent;

R' and R" are each independently selected from the group consisting of hydrogen and $C_{1-4}$alkyl;

$R^3$ is hydrogen; and $R^4$ is selected from the group consisting of hydrogen, $C_{1-4}$alkyl and —$C_{1-4}$alkyl-O—$C_{1-4}$alkyl;

or a N-oxide, or a pharmaceutically acceptable salt or a solvate thereof.

3. The method of claim 1, wherein
R[1] is phenyl or 2-pyridinyl, each optionally substituted with one or two substituents each independently selected from the group consisting of halo, $C_{1-4}$alkyl, polyhalo-$C_{1-4}$alkyl, —$C_{1-4}$alkyl-O—$C_{1-4}$alkyl, —O—$C_{1-4}$alkyl and polyhalo-$C_{1-4}$alkyloxy;
R[2] is selected from the group consisting of Aryl; and Het[2];
Aryl is phenyl optionally substituted with a halo substituent;
Het[2] is (a) a 6-membered aromatic heterocyclyl substituent selected from the group consisting of pyridinyl, pyrimidinyl and pyrazinyl, each of which may be optionally substituted with one or two substituents each independently selected from the group consisting of halo, $C_{1-4}$alkyl, —O—$C_{1-4}$alkyl and NR'R"; or (b) a 5-membered aromatic heterocyclyl selected from the group consisting of thiazolyl, 1,2-oxazolyl, 1,3-oxazolyl and 1H-imidazolyl, each of which may be optionally substituted with a $C_{1-4}$alkyl substituent;
R' and R" are each independently hydrogen;
R[3] is hydrogen; and
R[4] is selected from the group consisting of hydrogen, $C_{1-4}$alkyl and —$C_{1-4}$alkyl-O—$C_{1-4}$alkyl;
or a N-oxide, or a pharmaceutically acceptable salt thereof.

4. The method of claim 1, wherein
R[1] is phenyl or 2-pyridinyl, each optionally substituted with one or two substituents each independently selected from the group consisting of halo, $C_{1-4}$alkyl, polyhalo-$C_{1-4}$alkyl, —O—$C_{1-4}$alkyl and polyhalo-$C_{1-4}$ alkyloxy;
R[2] is selected from the group consisting of Aryl; and Het[2];
Aryl is phenyl optionally substituted with a halo substituent;
Het[2] is (a) pyridinyl or pyrazinyl, each of which may be optionally substituted with one or two substituents each independently selected from the group consisting of halo, $C_{1-4}$alkyl, —O—$C_{1-4}$alkyl and NR'R"; or (b) & thiazolyl;
R' and R" are each independently hydrogen; and
R[3] is hydrogen; and
R[4] is selected from the group consisting of $CH_3$ and $CH_2OCH_3$;
or a N-oxide, or a pharmaceutically acceptable salt thereof.

5. The method of claim 1, wherein the compound is of Formula (I')

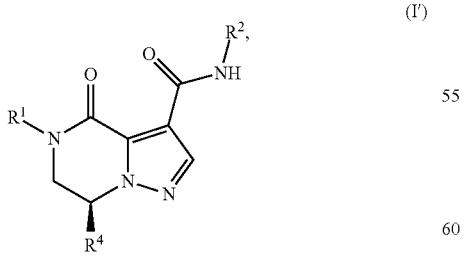

(I')

wherein R[4] is selected from the group consisting of $C_{1-4}$alkyl, monohalo-$C_{1-4}$alkyl, polyhalo-$C_{1-4}$alkyl, —$C_{1-4}$alkyl-O—$C_{1-4}$alkyl and —$C_{1-4}$alkyl-OH
or a N-oxide, or a pharmaceutically acceptable salt thereof.

6. The method of claim 1, wherein the compound is

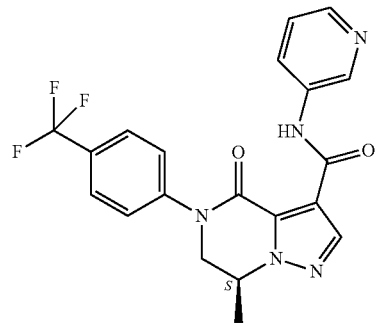

or a pharmaceutically acceptable salt or a solvate thereof.

7. The method of claim 1, wherein the compound is

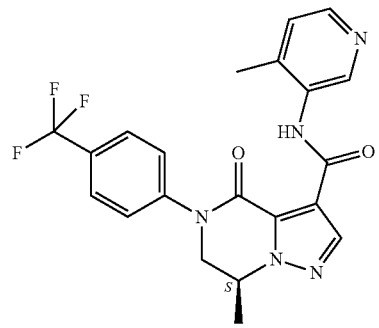

or a pharmaceutically acceptable salt or a solvate thereof.

8. The method of claim 1, wherein the compound is

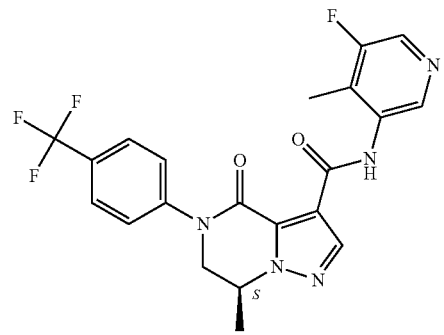

or a pharmaceutically acceptable salt or a solvate thereof.

9. The method of claim 1 wherein the depressive disorder is selected from the group consisting of major depressive disorder, persistent depressive disorder (dysthymia) and substance-medication-induced depressive disorder.

* * * * *